United States Patent
Borthwick et al.

(10) Patent No.: US 7,179,835 B2
(45) Date of Patent: Feb. 20, 2007

(54) 2-(3-SULFONYLAMINO-2-OXOPYRROLIDIN-1-YL)PROPANAMIDES AS FACTOR XA INHIBITORS

(75) Inventors: Alan David Borthwick, Stevenage (GB); Matthew Campbell, Stevenage (GB); Chuen Chan, Stevenage (GB); Henry Anderson Kelly, Stevenage (GB); Nigel Paul King, Stevenage (GB); Savvas Kleanthous, Stevenage (GB); Andrew McMurtrie Mason, Stevenage (GB); Stefan Senger, Stevenage (GB); Paul William Smith, Harlow (GB); Nigel Stephen Watson, Stevenage (GB); Robert John Young, Stevenage (GB)

(73) Assignee: Glaxo Group Limited, Greenford (GB)

( * ) Notice: Subject to any disclaimer, the term of this patent is extended or adjusted under 35 U.S.C. 154(b) by 0 days.

(21) Appl. No.: 10/495,586

(22) PCT Filed: Nov. 13, 2002

(86) PCT No.: PCT/GB02/05134

§ 371 (c)(1),
(2), (4) Date: May 14, 2004

(87) PCT Pub. No.: WO03/043981

PCT Pub. Date: May 30, 2003

(65) Prior Publication Data

US 2005/0004119 A1    Jan. 6, 2005

(30) Foreign Application Priority Data

Nov. 16, 2001    (GB) ................. 0127568.4

(51) Int. Cl.
*A61K 31/4025* (2006.01)
*A61K 31/55* (2006.01)
*C07D 207/22* (2006.01)
*C07D 403/12* (2006.01)
*C07D 413/12* (2006.01)

(52) U.S. Cl. ............. 514/423; 514/217.08; 514/237.2; 514/326; 514/343; 514/406; 514/422; 540/602; 544/141; 546/208; 546/278.4; 548/364.1; 548/527; 548/530

(58) Field of Classification Search ................. 548/550; 546/278.4, 208; 540/602; 544/141
See application file for complete search history.

(56) References Cited

U.S. PATENT DOCUMENTS

| 5,703,208 | A | 12/1997 | Semple et al. |
| 5,719,296 | A * | 2/1998 | Acton et al. ............. 548/550 |
| 5,932,733 | A | 8/1999 | Semple et al. |
| 6,034,215 | A | 3/2000 | Semple et al. |
| 6,187,797 | B1 | 2/2001 | Pruitt et al. |
| 6,281,227 | B1 | 8/2001 | Choi-Sledeski et al. |

FOREIGN PATENT DOCUMENTS

| DE | 41 21 947 | | 1/1993 |
| EP | 365992 | | 5/1990 |
| EP | 1 031 563 | | 8/2000 |
| WO | WO 93/01208 | * | 1/1993 |
| WO | WO-9535311 | | 11/1995 |
| WO | 95/35313 | | 12/1995 |
| WO | WO-9716425 A | | 5/1997 |
| WO | 98/16523 | | 4/1998 |
| WO | 98/25611 | | 6/1998 |
| WO | WO-9918074 A | | 4/1999 |
| WO | 99/62904 | | 12/1999 |
| WO | 00/47563 | | 8/2000 |
| WO | WO-0107407 | | 2/2001 |
| WO | 01/19795 | | 3/2001 |
| WO | 01/39759 | | 6/2001 |
| WO | 01/79261 | | 10/2001 |

OTHER PUBLICATIONS

Acton et al., STN International (2005) HCAPLUS Database, Accession No. 1998:146592, Reg. No. 190377-96-9.*
Acton et al., STN International (2005) HCAPLUS Database, Columbus, OH, Accession No. 1998:146592, Reg. No. 190377-96-9.*
Semple, J.E., "Design, sytnehsis, and evolution of a novel, selective, and orally bioavailable class of thrombin inhibitors: P1-argininal derivatives incorporating P3-4 lactam sulfonamide moieties," *Journal of Medicinal Chemistry*, vol. 39, No. 23, 1996, pp. 4531-4536.

(Continued)

*Primary Examiner*—Kamal A. Saeed
*Assistant Examiner*—Andrew B. Freistein
(74) *Attorney, Agent, or Firm*—Amy H. Fix

(57) ABSTRACT

The invention relates to compounds of formula (I) pharmaceutical compositions containing the same as well as methods of treating patients suffering from a condition susceptible to amelioration by a Factor Xa inhibitor using the same.

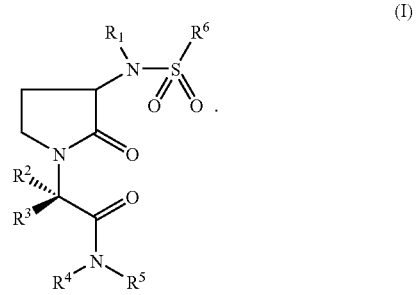

(I)

10 Claims, No Drawings

OTHER PUBLICATIONS

Semple, J.E. et al., "Rational design and synthesis of a novel, selective class of thrombin inhibitors: P1-argininal derivatives incorporating P3-P4, quaternary lactam dipeptide surrogates," *Bioorganic & Medicinal Chemistry Letters*, vol. 7, No. 18,997, pp. 2421-2426.

J. Med. Chem.; 1996; 4531-4536; 39(23).

Pept. 1996, Proc. Eur. Pept. Symp., 24th; 1996; 71-74.

Young et al., "Structure-and property-based design of factor Xa inhibitors: Pyrrolidin-2-ones with acyclic alanyl amides as P4 motifs," *Bioorganic & Medicinal Chemistry Letters*, 2006, doi:10.1016/j.bmcl.2006.09.0001.

* cited by examiner

2-(3-SULFONYLAMINO-2-OXOPYRROLIDIN-1-YL)PROPANAMIDES AS FACTOR XA INHIBITORS

This application is filed pursuant to 35 U.S.C. § 371 as a United States National Phase Application of International Application No. PCT/GB02/05134 filed Nov. 13, 2002, which claims priority from GB 0127568.4 filed Nov. 16, 2001.

FIELD OF THE INVENTION

The present invention relates to a novel class of chemical compounds, to processes for their preparation, to pharmaceutical compositions containing them and to their use in medicine, particularly use in the amelioration of a clinical condition for which a Factor Xa inhibitor is indicated.

BACKGROUND OF THE INVENTION

Factor Xa is a member of the trypsin-like serine protease class of enzymes. It is a key enzyme in the coagulation cascade. A one-to-one binding of Factors Xa and Va with calcium ions and phospholipid converts prothrombin into thrombin. Thrombin plays a central role in the mechanism of blood coagulation by converting the soluble plasma protein, fibrinogen, into insoluble fibrin. The insoluble fibrin matrix is required for the stabilisation of the primary hemostatic plug. Many significant disease states are related to abnormal hemostasis. With respect to the coronary arterial vasculature, abnormal thrombus formation due to the rupture of an established atherosclerotic plaque is the major cause of acute myocardial infarction and unstable angina. Both treatment of an occlusive coronary thrombus by thrombolytic therapy and percutaneous transluminal coronary angioplasty (PTCA) are often accompanied by an acute thrombotic reclosure of the affected vessel which requires immediate resolution. With respect to the venous vasculature, a high percentage of patients undergoing major surgery in the lower extremities or the abdominal area suffer from thrombus formation in the venous vasculature which can result in reduced blood flow to the affected extremity and a predisposition to pulmonary embolism. Disseminated intravascular coagulopathy commonly occurs within both vascular systems during septic shock, certain viral infections and cancer and is characterised by the rapid consumption of coagulation factors and systemic coagulation which results in the formation of life-threatening thrombi occurring throughout the vasculature leading to widespread organ failure.

Beyond its direct role in the formation of fibrin rich blood clots, thrombin has been reported to have profound bioregulatory effects on a number of cellular components within the vasculature and blood, (Shuman, M. A., Ann. NY Acad. Sci., 405: 349 (1986)).

A Factor Xa inhibitor may be useful in the treatment of acute vascular diseases such as coronary thrombosis (for example myocardial infarction and unstable angina), thromboembolism, acute vessel closure associated with thrombolytic therapy and percutaneous transluminal coronary angioplasty, transient ischemic attacks, pulmonary embolism, deep vein thrombosis, peripheral arterial occlusion, prevention of vessel luminal narrowing (restenosis), and the prevention of thromboembolic events associated with atrial fibrillation, e.g. stroke. They may also have utility as anticoagulant agents both in-vivo and ex-vivo, and in oedema and inflammation. Thrombin has been reported to contribute to lung fibroblast proliferation, thus, Factor Xa inhibitors could be useful for the treatment of some pulmonary fibrotic diseases. Factor Xa inhibitors could also be useful in the treatment of tumour metastasis, preventing the fibrin deposition and metastasis caused by the inappropriate activation of Factor Xa by cysteine proteinases produced by certain tumour cells. Thrombin can induce neurite retraction and thus Factor Xa inhibitors may have potential in neurogenerative diseases such as Parkinson's and Alzheimer's disease. They have also been reported for use in conjunction with thrombolytic agents, thus permitting the use of a lower dose of thrombolytic agent.

DESCRIPTION OF THE INVENTION

The present invention provides compounds of formula (I):

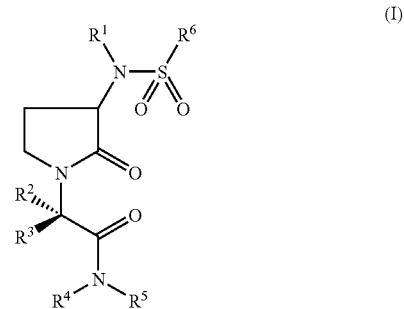

(I)

wherein:

$R^1$ represents hydrogen or —$C_{1-3}$alkylCONR$^a$R$^b$;

One of $R^2$ and $R^3$ represents —$C_{1-3}$alkyl and the other represents hydrogen;

$R^4$ represents hydrogen, —$C_{1-4}$alkyl, —$C_{3-4}$alkenyl, —$C_{2-4}$alkylOH, —$C_{2-4}$allkylOC$_{1-4}$alkyl, —$C_{1-4}$alkylCN or —$C_{0-4}$alkylC$_{3-6}$cycloalkyl;

$R^5$ represents —$C_{2-4}$alkylOH, —$C_{1-4}$alkyl, —$C_{2-4}$alkylOC$_{1-4}$ alkyl, —$C_{1-4}$alkylCN, —$C_{1-4}$alkylCONR$^c$R$^d$, —$C_{2-4}$alkylNR$^a$R$^b$, —$C_{2-4}$alkylNHCOC$_{1-3}$alkyl, —$C_{2-4}$alkylNHCONR$^a$R$^b$, —$C_{2-4}$alkylNHSO$_2$R$^e$, —$C_{2-4}$alkylSO$_2$NR$^a$R$^b$, —$C_{2-4}$alkylNHCO$_2$C$_{1-4}$alkyl, —$C_{2-4}$alkylNHC(NH$_2$)=NR$^f$, or a group X—Y;

X represents —$C_{1-4}$alkylene- optionally substituted by —OH, or a direct link, with the proviso that when X is substituted by —OH, X represents $C_{2-4}$alkylene and the —OH group is not alpha with respect to the amide N atom to which the group X is attached;

Y represents —$C_{3-6}$cycloalkyl, phenyl, or an aromatic or non-aromatic 5-, 6- or 7-membered heterocyclic group containing at least one heteroatom selected from O, N or S and optionally substituted at C and/or N atoms by —$C_{1-3}$alkyl, $C_{1-3}$alkoxy, $C_{1-3}$alkylOH, halogen, —CN, —CF$_3$, —NH$_2$, —CO$_2$H and —OH;

$R^a$ and $R^b$ independently represent hydrogen or —$C_{1-4}$alkyl;

$R^c$ and $R^d$ independently represent hydrogen or —$C_{1-4}$alkyl or together with the N atom to which they are attached form a non-aromatic 5-, 6- or 7-membered heterocyclic group optionally substituted by a heteroatom selected from O, N or S;

$R^e$ represents —$C_{1-4}$alkyl or —CF$_3$;

$R^f$ represents NO$_2$ or CN;

$R^6$ represents a group selected from:

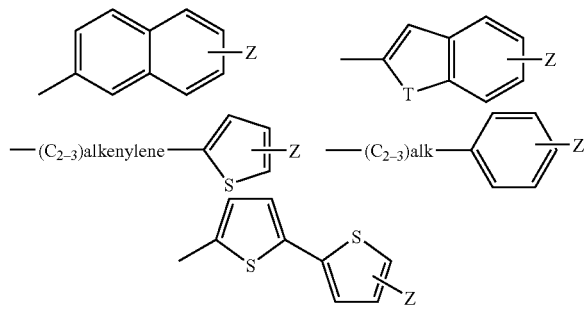

Z represents an optional substituent halogen,
alk represents alkylene or alkenylene,
T represents a heteroatom selected from S or N;

and pharmaceutically acceptable derivatives thereof.

Further aspects of the invention are:
A pharmaceutical composition comprising a compound of the invention together with a pharmaceutical carrier and/or excipient.
A compound of the invention for use in therapy.
Use of a compound of the invention for the manufacture of a medicament for the treatment of a patient suffering from a condition susceptible to amelioration by a Factor Xa inhibitor.
A method of treating a patient suffering from a condition susceptible to amelioration by a Factor Xa inhibitor comprising administering a therapeutically effective amount of a compound of the invention.

The compounds of formula (I) contain chiral (asymmetric) centres. The individual stereoisomers (enantiomers and diastereoisomers) and mixtures of these are within the scope of the present invention.

The present invention also provides certain compounds of formula (I) which are represented by formula (IA):

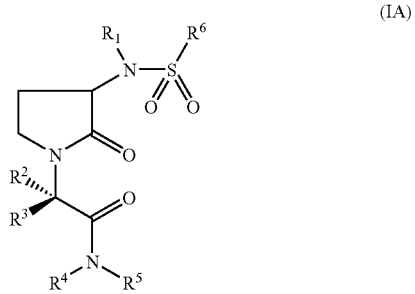

wherein:
$R^1$ represents hydrogen or —$C_{1-3}$alkylCONR$^a$R$^b$;
One of $R^2$ and $R^3$ represents —$C_{1-3}$alkyl and the other represents hydrogen;
$R^4$ represents —$C_{1-4}$alkyl, —$C_{2-4}$alkylOH, —$C_{1-4}$alkylCN, —$C_{3-6}$cycloalkyl;
$R^5$ represents —$C_{2-4}$alkylOH, —$C_{1-4}$alkyl, —$C_{2-4}$alkylOC$_{1-3}$ alkyl, —$C_{1-4}$alkylCN, —$C_{1-4}$alkylCONR$^a$R$^b$, —$C_{2-4}$alkylNR$^a$R$^b$, —$C_{2-4}$alkylNHCOC$_{1-3}$alkyl, —$C_{2-4}$alkylNHCONR$^a$R$^b$, —$C_{2-4}$alkylNHSO$_2$R$^a$, —$C_{1-4}$alkylSO$_2$NR$^a$R$^b$, or a group X—Y;
X represents —$C_{1-4}$alkylene- or a direct link;
Y represents —$C_{3-6}$cycloalkyl, phenyl, or an aromatic or non-aromatic 5-, 6- or 7-membered heterocyclic group containing one or two O, N or S atoms and optionally substituted at C and/or N atoms by —$C_{1-3}$alkyl;
$R^a$ and $R^b$ independently represent hydrogen or —$C_{1-3}$alkyl;
$R^6$ represents a group selected from:

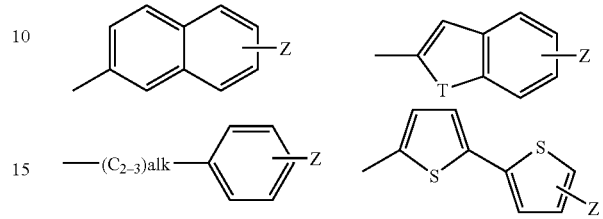

Z represents an optional substituent halogen,
alk represents alkylene or alkenylene,
T represents a heteroatom selected from S or N;

and pharmaceutically acceptable salts and solvates thereof.

Preferably $R^1$ represents hydrogen or —$C_{1-3}$alkyl-CONH$_2$. More preferably $R^1$ represents hydrogen or —CH$_2$CONH$_2$.

Preferably, one of $R^2$ and $R^3$ represents methyl and the other represents hydrogen.

Preferably, $R^4$ represents —$C_{1-4}$alkyl, —$C_{3-4}$alkenyl, —$C_{2-4}$alkylOH, —$C_{2-4}$alkylOC$_{1-4}$alkyl, —$C_{1-4}$alkylCN or —$C_{0-4}$alkylC$_{3-6}$cycloalkyl. More preferably, $R^4$ represents —$C_{1-3}$alkyl, —$C_{1-3}$alkylCN or —$C_{0-4}$alkylC$_{3-6}$cycloalkyl. Even more preferably, $R^4$ represents —$C_{1-3}$alkyl, —CH$_2$CH$_2$CN, —CH$_2$cyclopropyl or —$C_{3-5}$cycloalkyl.

In another preferred aspect, $R^4$ represents —$C_{1-4}$alkyl, —$C_{2-4}$alkylOH or —$C_{1-4}$alkylCN.

Preferably $R^5$ represents —$C_{2-4}$alkylOH, —$C_{1-4}$alkyl, —$C_{2-4}$alkylOC$_{1-4}$alkyl, —$C_{1-4}$alkylCN, —$C_{1-4}$alkylCONR$^c$R$^d$, —$C_{2-4}$alkylNR$^a$R$^b$, —$C_{2-4}$alkylNHCOC$_{1-3}$alkyl, —$C_{2-4}$alkylNHCONR$^a$R$^b$, —$C_{2-4}$alkylNHSO$_2$R$^e$, —$C_{2-4}$alkylSO$_2$NR$^a$R$^b$, —$C_{2-4}$alkylNHCO$_2$C$_{1-4}$alkyl, —$C_{2-4}$alkylNHC(NH$_2$)=NR$^f$, or a group X—Y.

X represents —$C_{1-4}$alkylene- optionally substituted by —OH, or a direct link, with the proviso that when X is substituted by —OH, X represents $C_{2-4}$alkylene and the —OH group is not alpha with respect to the amide N atom to which the group X is attached;

Y represents phenyl, or an aromatic or non-aromatic 5-, 6- or 7-membered heterocyclic group containing one or two heteroatoms selected from O, N or S atoms and optionally substituted at C and/or N atoms by —$C_{1-3}$alkyl.

More preferably, $R^5$ represents —$C_{2-4}$alkylOH, —$C_{1-4}$alkyl, —$C_{2-4}$alkylOC$_{1-3}$alkyl, —$C_{1-4}$alkylCN, —$C_{1-4}$alkylCONR$^c$R$^d$, —$C_{2-4}$alkylNR$^a$R$^b$, —$C_{2-4}$alkylNHCOC$_{1-3}$alkyl, —$C_{2-4}$alkylNHCONR$^a$R$^b$, —$C_{2-4}$alkylNHSO$_2$R$^e$, —$C_{2-4}$alkylSO$_2$NR$^a$R$^b$, —$C_{2-4}$alkylNHCO$_2$C$_{1-4}$alkyl, —$C_{2-4}$alkylNHC(NH$_2$)=NR$^f$, or a group X—Y;

X represents —$C_{1-3}$alkylene-;

Y represents phenyl, or an aromatic or non-aromatic 5-, 6- or 7-membered heterocyclic group containing one or two heteroatoms selected from O, N or S atoms and optionally substituted at C and/or N atoms by —$C_{1-3}$alkyl.

Even more preferably, $R^5$ represents —$C_{2-4}$alkylOH, —$C_{1-4}$alkyl, —$C_{2-4}$alkylOC$_{1-3}$alkyl, —$C_{1-3}$alkylCN, —$C_{1-4}$alkylCONR$^c$R$^d$, —$C_{2-4}$alkylNR$^a$R$^b$, —$C_{2-4}$alkylNHCOC$_{1-3}$alkyl, —$C_{2-3}$alkylNHCONR$^a$R$^b$, —$C_{2-3}$alkylNHSO$_2$R$^e$, —$C_{2-4}$alkylSO$_2$NR$^a$R$^b$, —$C_{2-4}$alkylNHCO$_2$C$_{1-4}$alkyl, —$C_{2-4}$alkylNHC(NH$_2$)=NR$^f$, or a group X—Y;

X represents —$C_{1-3}$alkylene-;

Y represents phenyl, or a heterocyclic group selected from thiophene, tetrahydrofuran, pyrrolidine, imidazole, pyridine, piperidine, morpholine, piperazine, pyrazole or hexamethyleneimine.

Most preferably, R$^5$ represents —$C_{1-3}$alkyl, —$C_{2-3}$alkylOH, —$C_{1-2}$alkylCN, —$C_{2-3}$alkylOCH$_3$, —$C_{2-3}$alkylNR$^a$R$^b$, —$C_{1-2}$alkylCONH$_2$, —CH$_2$CH$_2$NHCOCH$_3$, —$C_{2-3}$alkylNHSO$_2$CH$_3$, —CH$_2$CH$_2$SO$_2$NH$_2$, —$C_{2-3}$alkylNHCONH$_2$, —$C_{2-3}$alkylNHCO$_2$C$_4$alkyl, —$C_{2-3}$alkylNHC(NH$_2$)=NNO$_2$, or —$C_{1-3}$alkylW wherein W represents thiophene, pyridine, piperidine, morpholine, piperazine, pyrazole or hexamethyleneimine.

In another preferred aspect, R$^5$ represents —$C_{2-4}$alkylOH, —$C_{1-4}$alkyl, —$C_{2-4}$alkylOC$_{1-3}$alkyl, —$C_{1-4}$alkylCN, —$C_{1-4}$alkylCONR$^a$R$^b$, —$C_{2-4}$alkylNR$^a$R$^b$, —$C_{2-4}$alkylNHCOC$_{1-3}$alkyl, —$C_{2-4}$alkylNHCONR$^a$R$^b$, $C_{2-4}$alkylNHSO$_2$R$^a$, —$C_{1-4}$alkylSO$_2$NR$^a$R$^b$, or a group X—Y;

X represents —$C_{1-3}$alkylene- or a direct link;

Y represents —$C_{3-6}$cycloalkyl, phenyl, or a heterocyclic group selected from thiophene, tetrahydrofuran, pyrrolidine, imidazole, pyridine, piperidine, morpholine or hexamethyleneimine and optionally substituted at C and/or N atoms by —$C_{1-3}$alkyl.

When Y is a heterocycle selected from thiophene, tetrahydrofuran or pyridine, the heterocyclic ring is C-linked to X. When Y represents a heterocycle selected from imidazole, pyrrolidine, piperidine, morpholine, piperazine, pyrazole or hexamethyleneimine, the heterocyclic ring is C-linked or N-linked to X. Preferably, when Y represents a heterocyclic ring selected from pyrrolidine, piperazine, morpholine or hexamethyleneimine, the heterocyclic ring is N-linked to X.

Preferably, R$^6$ represents a group selected from: chloronaphthylene, chlorobenzothiophene, chlorobithiophene, chlorophenylethene or (chlorothienyl)ethene. More preferably, R$^6$ represents 6-chloronaphthylene, 5'-chloro-2,2'-bithiophene, (4-chlorophenyl)ethene, or 5'-(chlorothienyl)ethene. Most preferably, R$^6$ represents 6-chloro-1-benzothiophene, 6-chloronaphthylene, 5'-chloro-2,2'-bithiophene or (4-chlorophenyl)ethene.

Preferably, R$^a$ and R$^b$ independently represent hydrogen or methyl.

Preferably, R$^c$ and R$^d$ independently represent hydrogen or —$C_{1-3}$alkyl;

Preferably, R$^f$ represents NO$_2$.

It is to be understood that the present invention covers all combinations of preferred, more preferred, even more preferred and most preferred groups described herein above.

The present invention also provides compounds of formula (I) wherein:

R$_1$ represents H or $C_{1-3}$alkylCONR$^a$R$^b$;

One of R$^2$ and R$^3$ represents —$C_{1-3}$alkyl and the other represents hydrogen;

R$^4$ represents $C_{1-4}$alkyl, $C_{2-4}$alkylOH or $C_{1-4}$alkylCN;

R$^5$ represents —$C_{2-4}$alkylOH, —$C_{1-4}$alkyl, —$C_{2-4}$alkylOC$_{1-3}$ alkyl, —$C_{1-4}$alkylCN, —$C_{1-4}$alkylCONR$^a$R$^b$, —$C_{2-4}$alkylNR$^a$R$^b$, —$C_{2-4}$alkylNHCOC$_{1-3}$alkyl, —$C_{2-4}$alkylNHCONR$^a$R$^b$, $C_{2-4}$alkylNHSO$_2$R$^a$, —$C_{1-4}$alkylSO$_2$NR$^a$R$^b$, or a group X—Y;

X represents —$C_{1-3}$alkylene- or a direct link;

Y represents —$C_{3-6}$cycloalkyl, phenyl, or a heterocyclic group selected from thiophene, tetrahydrofuran, pyrrolidine, imidazole, pyridine, piperidine, morpholine or hexamethyleneimine and optionally substituted at C and/or N atoms by —$C_{1-3}$alkyl;

R$^a$ and R$^b$ independently represent hydrogen or $C_{1-3}$alkyl;

R$^6$ represents 6-chloronaphthylene, 5'-chloro-2,2'-bithiophene, (4-chlorophenyl)ethene, 5chloro-1-benzothiophene, 6-chloro-1-benzothiophene;

and pharmaceutically acceptable salts and solvates thereof.

The present invention also provides compounds of formula (I) wherein:

R$^1$ represents H or $C_{1-3}$alkylCONR$^a$R$^b$;

One of R$^2$ and R$^3$ represents —$C_{1-3}$alkyl and the other represents hydrogen;

R$^4$ represents $C_{1-4}$alkyl, $C_{2-4}$alkylOH or $C_{1-4}$alkylCN;

R$^5$ represents —$C_{2-4}$alkylOH, —$C_{1-4}$alkyl, —$C_{2-4}$alkylOC$_{1-3}$ alkyl, —$C_{1-4}$alkylCN, —$C_{1-4}$alkylCONR$^a$R$^b$, —$C_{2-4}$alkylNR$^a$R$^b$, —$C_{2-4}$alkylNHCOC$_{1-3}$alkyl, —$C_{2-4}$alkylNHCONR$^a$R$^b$, $C_{2-4}$alkylNHSO$_2$R$^a$, —$C_{1-4}$alkylSO$_2$NR$^a$R$^b$, or a group X—Y;

X represents —$C_{1-3}$alkylene- or a direct link;

Y represents —$C_{3-6}$cycloalkyl, phenyl, or a heterocyclic group selected from thiophene, tetrahydrofuran, pyrrolidine, imidazole, pyridine, piperidine, morpholine or hexamethyleneimine and optionally substituted at C and/or N atoms by —$C_{1-3}$alkyl;

R$^a$ and R$^b$ independently represent hydrogen or $C_{1-3}$alkyl;

R$^6$ represents 6-chloronaphthylene;

and pharmaceutically acceptable salts and solvates thereof.

The present invention also provides compounds of formula (I) wherein:

R$^1$ represents H or $C_{1-3}$alkylCONR$^a$R$^b$;

One of R$^2$ and R$^3$ represents —$C_{1-3}$alkyl and the other represents hydrogen;

R$^4$ represents $C_{1-4}$alkyl, $C_{2-4}$alkylOH or $C_{1-4}$alkylCN;

R$^5$ represents —$C_{2-3}$alkylOH, —$C_{1-4}$alkyl, —$C_{2-3}$alkylOCH$_3$, —$C_{1-3}$alkylCN, —$C_{1-3}$alkylCONH$_2$, —$C_{2-3}$alkylN(CH$_3$)(CH$_3$), —$C_{2-3}$alkylNHCOCH$_3$, —$C_{2-3}$alkylNHCONR$^a$R$^b$, —$C_{2-3}$alkylNHSO$_2$R$^a$, —$C_{1-3}$alkylSO$_2$NR$^a$R$^b$, or a group X—Y;

X represents —$C_{1-3}$alkylene- or a direct link;

Y represents —$C_{3-6}$cycloalkyl, phenyl, or a heterocyclic group selected from thiophene, pyrrolidine, pyridine, piperidine or hexamethyleneimine;

R$^a$ and R$^b$ independently represent hydrogen or $C_{1-3}$alkyl;

R$^6$ represents 6-chloronaphthylene, 5'-chloro-2,2'-bithiophene, (4-chlorophenyl)ethene, 5-chloro-1-benzothiophene, 6-chloro-1-benzothiophene;

and pharmaceutically acceptable salts and solvates thereof.

The present invention also provides compounds of formula (I) wherein:

R$^1$ represents H or $C_{1-3}$alkylCONR$^a$R$^b$;

One of R$^2$ and R$^3$ represents —$C_{1-3}$alkyl and the other represents hydrogen;

R$^4$ represents $C_{1-4}$alkyl, $C_{2-4}$alkylOH or $C_{1-4}$alkylCN;

R$^5$ represents —$C_{2-3}$alkylOH, —$C_{1-4}$alkyl, —$C_{2-3}$alkylOCH$_3$, —$C_{1-3}$alkylCN, —$C_{1-3}$alkylCONH$_2$, —$C_{2-3}$alkylN(CH$_3$)(CH$_3$), —$C_{2-3}$alkylNHCOCH$_3$, —$C_{2-3}$alkylNHCONR$^a$R$^b$, —$C_{2-3}$alkylNHSO$_2$R$^a$, —$C_{1-3}$alkylSO$_2$NR$^a$R$^b$, or a group X—Y;

X represents —$C_{1-3}$alkylene- or a direct link;

Y represents —$C_{3-6}$cycloalkyl, phenyl, or a heterocyclic group selected from thiophene, pyrrolidine, pyridine, piperidine or hexamethyleneimine;

R$^a$ and R$^b$ independently represent hydrogen or $C_{1-3}$alkyl;

R$^6$ represents 6-chloronaphthylene;

and pharmaceutically acceptable salts and solvates thereof.

The present invention also provides compounds of formula (I) wherein:

$R^1$ represents H or $CH_2CONH_2$;

One of $R^2$ and $R^3$ represents —$C_{1-3}$alkyl and the other represents hydrogen;

$R^4$ represents $C_{1-4}$alkyl, $C_{2-4}$alkylOH or $C_{1-4}$alkylCN;

$R^5$ represents —$C_{2-4}$alkylOH, —$C_{1-4}$alkyl, —$C_{2-4}$alkylOC$_{1-3}$ alkyl, —$C_{1-4}$alkylCN, —$C_{1-4}$alkylCONR$^a$R$^b$, —$C_{2-4}$alkylNR$^a$R$^b$, —$C_{2-4}$alkylNHCOC$_{1-3}$alkyl, —$C_{2-4}$alkylNHCONR$^a$R$^b$, —$C_{2-4}$alkylNHSO$_2$R$^a$, —$C_{1-4}$alkylSO$_2$NR$^a$R$^b$, or a group X—Y;

X represents —$C_{1-3}$alkylene- or a direct link;

Y represents —$C_{3-6}$cycloalkyl, phenyl, or a heterocyclic group selected from thiophene, tetrahydrofuran, pyrrolidine, imidazole, pyridine, piperidine, morpholine or hexamethyleneimine and optionally substituted at C and/or N atoms by —$C_{1-3}$alkyl;

$R^a$ and $R^b$ independently represent hydrogen or $C_{1-3}$alkyl;

$R^6$ represents 6-chloronaphthylene, 5'-chloro-2,2'-bithiophene, (4-chlorophenyl)ethene, 5-chloro-1-benzothiophene, 6-chloro-1-benzothiophene;

and pharmaceutically acceptable salts and solvates thereof.

The present invention also provides compounds of formula (I) wherein:

$R^1$ represents H or $CH_2CONH_2$;

One of $R^2$ and $R^3$ represents —$C_{1-3}$alkyl and the other represents hydrogen;

$R^4$ represents $C_{1-4}$alkyl, $C_{2-4}$alkylOH or $C_{1-4}$alkylCN;

$R^5$ represents —$C_{2-4}$alkylOH, —$C_{1-4}$alkyl, —$C_{2-4}$alkylOC$_{1-3}$ alkyl, —$C_{1-4}$alkylCN, —$C_{1-4}$alkylCONR$^a$R$^b$, —$C_{2-4}$alkylNR$^a$R$^b$, —$C_{2-4}$alkylNHCOC$_{1-3}$alkyl, —$C_{2-4}$alkylNHCONR$^a$R$^b$, —$C_{2-4}$alkylNHSO$_2$R$^a$, —$C_{1-4}$alkylSO$_2$NR$^a$R$^b$, or a group X—Y;

X represents —$C_{1-3}$alkylene- or a direct link;

Y represents —$C_{3-6}$cycloalkyl, phenyl, or a heterocyclic group selected from thiophene, tetrahydrofuran, pyrrolidine, imidazole, pyridine, piperidine, morpholine or hexamethyleneimine and optionally substituted at C and/or N atoms by —$C_{1-3}$alkyl;

$R^a$ and $R^b$ independently represent hydrogen or $C_{1-3}$alkyl;

$R^6$ represents 6-chloronaphthylene;

and pharmaceutically acceptable salts and solvates thereof.

The present invention also provides compounds of formula (I) wherein:

$R^1$ represents H or $CH_2CONH_2$;

One of $R^2$ and $R^3$ represents —$C_{1-3}$alkyl and the other represents hydrogen;

$R^4$ represents $C_{1-4}$alkyl, $C_{2-4}$alkylOH or $C_{1-4}$alkylCN;

$R^5$ represents —$C_{2-3}$alkylOH, —$C_{1-4}$alkyl, —$C_{2-3}$alkylOCH$_3$, —$C_{1-3}$alkylCN, —$C_{1-3}$alkylCONH$_2$, —$C_{2-3}$alkylN(CH$_3$)(CH$_3$), —$C_{2-3}$alkylNHCOCH$_3$, —$C_{2-3}$alkylNHCONR$^a$R$^b$, —$C_{2-3}$alkylNHSO$_2$R$^a$, —$C_{1-3}$alkylSO$_2$NR$^a$R$^b$, or a group X—Y;

X represents —$C_{1-3}$alkylene- or a direct link;

Y represents —$C_{3-6}$cycloalkyl, phenyl, or a heterocyclic group selected from thiophene, pyrrolidine, pyridine, piperidine or hexamethyleneimine;

$R^a$ and $R^b$ independently represent hydrogen or $C_{1-3}$alkyl;

$R^6$ represents 6-chloronaphthylene;

and pharmaceutically acceptable salts and solvates thereof.

As used herein, the terms "alkyl" and "alkoxy" mean both straight and branched chain saturated hydrocarbon groups. Examples of alkyl groups include methyl (—CH$_3$), ethyl (—C$_2$H$_5$), propyl (—C$_3$H$_7$) and butyl (—C$_4$H$_9$). Examples of alkoxy groups include methoxy (—OCH$_3$) and ethoxy (—OC$_2$H$_5$).

As used herein, the term "alkylene" means both straight and branched chain saturated hydrocarbon linker groups. Examples of alkylene groups include methylene (—CH$_2$—), ethylene (—CH$_2$CH$_2$—) and propylene (—CH$_2$CH$_2$CH$_2$—).

As used herein, the term "alkenylene" means both straight and branched chain unsaturated hydrocarbon linker groups, wherein the unsaturation is present only as double bonds. Examples of alkenylene groups includes ethenylene (—CH=CH—) and propenylene (—CH$_2$—CH=CH—).

As used herein, the term "halogen" includes fluorine, chlorine, bromine and iodine.

As used herein, the term "cycloalkyl group" means an aliphatic ring. Examples of cycloalkyl groups include cyclopropyl, cyclobutyl, cyclopentyl and cyclohexyl.

As used herein, the term "heterocyclic group" means rings containing one or more heteroatoms selected from: nitrogen, sulphur and oxygen atoms. The heterocycle may be aromatic or non-aromatic, i.e., may be saturated, partially or fully unsaturated. Examples of 5-membered groups include thienyl, furanyl, pyrrolidinyl and imidazolyl. Examples of 6-membered groups include pyridyl, piperidinyl, morpholinyl, piperazinyl, pyrazinyl. Examples of 7-membered groups include hexamethyleneiminyl.

As used herein, the term "pharmaceutically acceptable" means a compound which is suitable for pharmaceutical use.

As used herein, the term "pharmaceutically acceptable derivative", means any pharmaceutically acceptable salt, solvate, or prodrug e.g. ester or carbamate, or salt or solvate of such a prodrug, of a compound of formula (I), which upon administration to the recipient is capable of providing (directly or indirectly) a compound of formula (I), or an active metabolite or residue thereof. Preferred pharmaceutically acceptable derivatives are salts, solvates, esters, carbamates and phosphate esters. Particularly preferred pharmaceutically acceptable derivatives are salts, solvates and esters. Most preferred pharmaceutically acceptable derivatives are salts and solvates.

Suitable salts according to the invention include those formed with both organic and inorganic acids and bases. Pharmaceutically acceptable acid addition salts include those (2S)-2-((3S)-3-{[(6-Chloro-2-naphthyl)sulfonyl]amino}-2-oxopyrrolidin-1-yl)-N-(2-cyanoethyl)-N-isobutylpropanamide (2S)-2-((3S)-3-{[(6-Chloro-2-naphthyl)sulfonyl]amino}-2-oxopyrrolidin-1-yl)-N,N-dimethylpropanamide (2S)-2-((3S)-3-{[(6-Chloro-2-naphthyl)sulfonyl]amino}-2-oxopyrrolidin-1-yl)-N-isopropyl-N-methylpropanamide (2S)-2-((3S)-3-{[(6-Chloro-2-naphthyl)sulfonyl]amino}-2-oxopyrrolidin-1-yl)-N-(2-hydroxyethyl)-N-methylpropanamide (2S)-2-((3S)-3-{[(6-Chloro-2-naphthyl)sulfonyl]amino}-2-oxopyrrolidin-1-yl)-N-(2-cyanoethyl)-N-methylpropanamide (2S)-N-(2-Amino-2-oxoethyl)-2-((3S)-3-{[(6-chloro-2-naphthyl)sulfonyl]amino}-2-oxopyrrolidin-1-yl)-N-methylpropanamide (2S)-2-((3S)-3-{[(6-Chloro-2-naphthyl)sulfonyl]amino}-2-oxopyrrolidin-1-yl)-N-[2-(dimethylamino)-2-oxoethyl]-N-methylpropanamide (2S)-2-((3S)-3-{[(6-Chloro-2-naphthyl)sulfonyl]amino}-2-oxopyrrolidin-1-yl)-N-ethyl-N-(3-hydroxypropyl)propanamide (2S)-2-((3S)-3-{[(6-Chloro-2-naphthyl)sulfonyl]amino}-2-oxopyrrolidin-1-yl)-N-methyl-N-(2-pyrrolidin-1-ylethyl)propanamide formate (2S)-2-((3S)-3-{[(6-Chloro-2-naphthyl)sulfonyl]amino}-2-oxopyrrolidin-1-yl)-N-methyl-N-(2-morpholin-4-ylethyl)propanamide formate (2S)-2-((3S)-3-{[(6-Chloro-2-naphthyl)sulfonyl]amino}-2-oxopyrrolidin-1-yl)-N-ethyl-N-(2-morpholin-4-ylethyl)propanamide formate (2S)-2-((3S)-3-{[(6-Chloro-2-naphthyl)sulfonyl]amino}-2-oxopyrrolidin-1-yl)-N-[2-(dimethylamino)ethyl]-N-ethylpropanamide formate (2S)-2-((3S)-3-{[(6-Chloro-2-naphthyl)sulfonyl]amino}-2-oxopyrrolidin-1-yl)-N-isopropyl-N-(pyridin-2-ylmethyl)propanamide (2S)-2-((3S)-3-{[(6-Chloro-2-naphthyl)sulfonyl]amino}-2-oxopyrrolidin-1-yl)-N-ethyl-N-(2-pyridin-2-ylethyl)propanamide (2S)-2-((3S)-3-{[(6-Chloro-2-naphthyl)sulfonyl]amino}-2-oxopyrrolidin-1-yl)-N-methyl-N-(pyridin-2-ylmethyl)propanamide (2S)-2-((3S)-3-{[(6-Chloro-2-naphthyl)sulfonyl]amino}-2-oxopyrrolidin-1-yl)-N-methyl-N-(2-pyridin-4-ylethyl)propanamide (2S)-2-((3S)-3-{[(6-Chloro-2-naphthyl)sulfonyl]amino}-2-oxopyrrolidin-1-yl)-N-methyl-N-(pyridin-4-ylmethyl)propanamide (2S)-2-((3S)-3-{[(6-Chloro-2-naphthyl)sulfonyl]amino}-2-oxopyrrolidin-1-yl)-N-[2-(1H-imidazol-4-yl)ethyl]-N-methylpropanamide formate (2S)-2-((3S)-3-{[(6-Chloro-2-naphthyl)sulfonyl]amino}-2-oxopyrrolidin-1-yl)-N-(2-cyanoethyl)-N-(pyridin-3-ylmethyl)propanamide (2S)-2-((3S)-3-{[(6-Chloro-2-naphthyl)sulfonyl]amino}-2-oxopyrrolidin-1-yl)-N-ethyl-N-(2-hydroxyethyl)propanamide (2S)-2-((3S)-3-{[(6-Chloro-2-naphthyl)sulfonyl]amino}-2-oxopyrrolidin-1-yl)-N-(2-methoxyethyl)-N-methylpropanamide (2S)-2-((3S)-3-{[(6-Chloro-2-naphthyl)sulfonyl]amino}-2-oxopyrrolidin-1-yl)-N-ethyl-N-(2-piperidin-1-ylethyl)propanamide formate (2S)-2-((3S)-3-{[(6-Chloro-2-naphthyl)sulfonyl]amino}-2-oxopyrrolidin-1-yl)-N-isopropyl-N-(2-pyridin-2-ylethyl)propanamide (2S)-2-((3S)-3-{[(6-Chloro-2-naphthyl)sulfonyl]amino}-2-oxopyrrolidin-1-yl)-N-(2-hydroxypropyl)-N-isopropylpropanamide (2S)-2-((3S)-3-{[(6-Chloro-2-naphthyl)sulfonyl]amino}-2-oxopyrrolidin-1-yl)-N-(cyanomethyl)-N-isopropylpropanamide formate (2S)-2-((3S)-3-{[(6-Chloro-2-naphthyl)sulfonyl]amino}-2-oxopyrrolidin-1-yl)-N-isopropyl-N-(3-methoxypropyl)propanamide (2S)-2-((3S)-3-{[(6-Chloro-2-naphthyl)sulfonyl]amino}-2-oxopyrrolidin-1-yl)-N-isopropyl-N-(2-methoxyethyl)propanamide (2S)-N-[2-(Acetylamino)ethyl]-2-((3S)-3-{[(6-chloro-2-naphthyl)sulfonyl]amino}-2-oxopyrtolidin-1-yl)-N-isopropylpropanamide (2S)-N-Benzyl-2-((3S)-3-{[(6-chloro-2-naphthyl)sulfonyl]amino}-2-oxopyrrolidin-1-yl)-N-isopropylpropanamide (2S)-2-((3S)-3-{[(6-Chloro-2-naphthyl)sulfonyl]amino}-2-oxopyrrolidin-1-yl)-N-isopropyl-N-(thien-2-ylmethyl)propanamide (2S)-2-((3S)-3-{[(6-Chloro-2-naphthyl)sulfonyl]amino}-2-oxopyrrolidin-1-yl)-N-(3-hydroxypropyl)-N-isopropylpropanamide (2S)-2-((3S)-3-{[(6-Chloro-2-naphthyl)sulfonyl]amino}-2-oxopyrrolidin-1-yl)-N-(2-hydroxyethyl)-N-isopropylpropanamide (2S)-2-((3S)-3-{[(6-Chloro-2-naphthyl)sulfonyl]amino}-2-oxopyrrolidin-1-yl)-N-(3-hydroxypropyl)-N-(pyridin-4-ylmethyl)propanamide (2S)-2-((3S)-3-{[(6-Chloro-2-naphthyl)sulfonyl]amino}-2-oxopyrrolidin-1-yl)-N-(3-hydroxypropyl)-N-(pyridin-3-ylmethyl)propanamide (2S)-2-((3S)-3-{[(6-Chloro-2-naphthyl)sulfonyl]amino}-2-oxopyrrolidin-1-yl)-N-(3-hydroxypropyl)-N-(pyridin-2-ylmethyl)propanamide (2S)-2-((3S)-3-{[(6-Chloro-2-naphthyl)sulfonyl]amino}-2-oxopyrrolidin-1-yl)-N-(3-cyanoethyl)-N(tetrahydrofuran-2-ylmethyl)propanamide (2S)-2-((3S)-3-{[(6-Chloro-2-naphthyl)sulfonyl]amino}-2-oxopyrrolidin-1-yl)-N-(2-cyanoethyl)-N-(cyclopropylmethyl)propanamide (2S)-2-((3S)-3-{[(6-Chloro-2-naphthyl)sulfonyl]amino}-2-oxopyrrolidin-1-yl)-N-(2-cyanoethyl)-N-(2-pyridin-2-ylethyl)propanamide (2S)-2-((3S)-3-{[(6-Chloro-2-naphthyl)sulfonyl]amino}-2-oxopyrrolidin-1-yl)-N-(2-cyanoethyl)-N-isobutylpropanamide (2S)-2-((3S)-3-{(2-Amino-2-oxoethyl)[(6-chloro-2-naphthyl)sulfonyl]amino}-2-oxopyrrolidin-1-yl)-N-ethyl-N-(pyridin-4-ylmethyl)propanamide (2S)-2-((3S)-3-{(2-Amino-2-oxoethyl)[(6-chloro-2-naphthyl)sulfonyl]amino}-2-oxopyrrolidin-1-yl)-N-ethyl-N-(2-pyridin-2-ylethyl)propanamide (2S)-2-((3S)-3-{(2-amino-2-oxoethyl)[(6-chloro-2-naphthyl)sulfonyl]amino}-2-oxopyrrolidin-1-yl)-N-ethyl-N-(2-hydroxyethyl)propanamide (2S)-2-((3S)-3-{(2-Amino-2-oxoethyl)[(6-chloro-2-naphthyl)sulfonyl]amino}-2-oxopyrrolidin-1-yl)-N-isopropyl-N-(pyridin-2-ylmethyl)propanamide (2S)-2-((3S)-3-{(2-Amino-2-oxoethyl)[(6-chloro-2-naphthyl)sulfonyl]amino}-2-oxopyrrolidin-1-yl)-N-methyl-N-(pyridin-2-ylmethyl)propanamide (2S)-2-((3S)-3-{(2-Amino-2-oxoethyl)[(6-chloro-2-naphthyl)sulfonyl]amino}-2-oxopyrrolidin-1-yl)-N-methyl-N-(pyridin-3-ylmethyl)propanamide (2S)-2-((3S)-3-{(2-Amino-2-oxoethyl)[(6-chloro-2-naphthyl)sulfonyl]amino}-2-oxopyrrolidin-1-yl)-N-methyl-N-(2-pyridin-4-ylethyl)propanamide (2S)-2-((3S)-3-{(2-Amino-2-oxoethyl)[(6-chloro-2-naphthyl)sulfonyl]amino}-2-oxopyrrolidin-1-yl)-N-methyl-N-(pyridin-4-ylmethyl)propanamide
(2S)-2-((3S)-3-{(2-Amino-2-oxoethyl)[(6-chloro-2-naphthyl)sulfonyl]amino}-2-oxopyrrolidin-1-yl)-N-[2-(H-imidazol-4-yl)ethyl]-N-methylpropanamide formate
(2S)-2-((3S)-3-{(2-Amino-2-oxoethyl)[(6-chloro-2-naphthyl)sulfonyl]amino}-2-oxopyrrolidin-1-yl)-N-methyl-N-(2-pyridin-2-ylethyl)propanamide
(2S)-2-((3S)-3-{(2-Amino-2-oxoethyl)[(6-chloro-2-naphthyl)sulfonyl]amino}-2-oxopyrrolidin-1-yl)-N-methyl-N-(2-phenylethyl)propanamide
(2S)-2-((3S)-3-{(2-Amino-2-oxoethyl)[(6-chloro-2-naphthyl)sulfonyl]amino}-2-oxopyrrolidin-1-yl)-N-ethyl-N-(2-phenylethyl)propanamide
(2S)-2-((3S)-3-{(2-Amino-2-oxoethyl)[(6-chloro-2-naphthyl)sulfonyl]amino}-2-oxopyrrolidin-1-yl)-N,N-dimethylpropanamide
(2S)-2-((3S)-3-{(2-Amino-2-oxoethyl)[(6-chloro-2-naphthyl)sulfonyl]amino}-2-oxopyrrolidin-1-yl)-N-isopropyl-N-methylpropanamide
(2S)-2-((3S)-3-{(2-Amino-2-oxoethyl)[(6-chloro-2-naphthyl)sulfonyl]amino}-2-oxopyrrolidin-1-yl)-N-(2-hydroxyethyl)-N-methylpropanamide
(2S)-2-((3S)-3-{(2-Amino-2-oxoethyl)[(6-chloro-2-naphthyl)sulfonyl]amino}-2-oxopyrrolidin-1-yl)-N-(2-hydroxyethyl)-N-isopropylpropanamide
(2S)-2-((3S)-3-{(2-Amino-2-oxoethyl)[(6-chloro-2-naphthyl)sulfonyl]amino}-2-oxopyrrolidin-1-yl)-N-(2-cyanoethyl)-N-methylpropanamide
(2S)-N-(2-Amino-2-oxoethyl)-2-((3S)-3-{(2-amino-2-oxoethyl)[(6-chloro-2-naphthyl)sulfonyl]amino}-2-oxopyrrolidin-1-yl)-N-methylpropanamide
(2S)-2-((3S)-3-{(2-Amino-2-oxoethyl)[(6-chloro-2-naphthyl)sulfonyl]amino}-2-oxopyrrolidin-1-yl)-N-[2-(dimethylamino)-2-oxoethyl]-N-methylpropanamide
(2S)-2-((3S)-3-{(2-Amino-2-oxoethyl)[(6-chloro-2-naphthyl)sulfonyl]amino}-2-oxopyrrolidin-1-yl)-N-ethyl-N-(3-hydroxypropyl)propanamide
(2S)-2-((3S)-3-{(2-Amino-2-oxoethyl)[(6-chloro-2-naphthyl)sulfonyl]amino}-2-oxopyrrolidin-1-yl)-N-methyl-N-(2-pyrrolidin-1-ylethyl)propanamide formate
(2S)-2-((3S)-3-{(2-Amino-2-oxoethyl)[(6-chloro-2-naphthyl)sulfonyl]amino}-2-oxopyrrolidin-1-yl)-N-methyl-N-(2-morpholin-4-ylethyl)propanamide formate
(2S)-2-((3S)-3-{(2-Amino-2-oxoethyl)[(6-chloro-2-naphthyl)sulfonyl]amino}-2-oxopyrrolidin-1-yl)-N-ethyl-N-(2-morpholin-4-ylethyl)propanamide formate
(2S)-2-((3S)-3-{(2-Amino-2-oxoethyl)[(6-chloro-2-naphthyl)sulfonyl]amino}-2-oxopyrrolidin-1-yl)-N-[2-(dimethylamino)ethyl]-N-ethylpropanamide formate
(2S)-2-((3S)-3-{(2-Amino-2-oxoethyl)[(6-chloro-2-naphthyl)sulfonyl]amino}-2-oxopyrrolidin-1-yl)-N-(2-cyanoethyl)-N-(pyridin-3-ylmethyl)propanamide
(2S)-2-((3S)-3-{(2-Amino-2-oxoethyl)[(6-chloro-2-naphthyl)sulfonyl]amino}-2-oxopyrrolidin-1-yl)-N-ethyl-N-(2-hydroxyethyl)propanamide
(2S)-2-((3S)-3-{(2-Amino-2-oxoethyl)[(6-chloro-2-naphthyl)sulfonyl]amino}-2-oxopyrrolidin-1-yl)-N-(2-methoxyethyl)-N-methylpropanamide
(2S)-2-((3S)-3-{(2-Amino-2-oxoethyl)[(6-chloro-2-naphthyl)sulfonyl]amino}-2-oxopyrrolidin-1-yl)-N-ethyl-N-(2-piperidin-1-ylethyl)propanamide formate
(2S)-2-((3S)-3-{(2-Amino-2-oxoethyl)[(6-chloro-2-naphthyl)sulfonyl]amino}-2-oxopyrrolidin-1-yl)-N-(2-hydroxyethyl)-N-(2-morpholin-4-ylethyl)propanamide formate
(2S)-2-((3S)-3-{(2-Amino-2-oxoethyl)[(6-chloronaphthyl-2-yl)sulfonyl]amino}-2-oxopyrrolidin-1-yl)-N-ethyl-N-methylpropanamide
(2S)-2-((3S)-3-{(2-Amino-2-oxoethyl)[(6-chloronaphth-2-yl)sulfonyl]amino}-2-oxopyrrolidin-1-yl)-N,N-diethylpropanamide
(2S)-2-((3S)-3-{(2-Amino-2-oxoethyl)[(6-chloronaphth-2-yl)sulfonyl]amino}-2-oxopyrrolidin-1-yl)-N,N-dipropylpropanamide
(2S)-2-((3S)-3-{(2-Amino-2-oxoethyl)[(6-chloronaphth-2-yl)sulfonyl]amino}-2-oxopyrrolidin-1-yl)-N-ethyl-N-isopropylpropanamide
(2S)-2-((3S)-3-{(2-Amino-2-oxoethyl)[(6-chloronaphth-2-yl)sulfonyl]amino}-2-oxopyrrolidin-1-yl)-N-isopropyl-N-(pyrid-4-ylmethyl)propanamide
(2S)-2-((3S)-3-{(2-Amino-2-oxoethyl)[(6-chloronaphth-2-yl)sulfonyl]amino}-2-oxopyrrolidin-1-yl)-N-(2-cyanoethyl)-N-isopropylpropanamide
(2S)-2-((3S)-3-{(2-Amino-2-oxoethyl)[(6-chloronaphth-2-yl)sulfonyl]amino}-2-oxopyrrolidin-1-yl)-N-(2-azepan-1-ylethyl)-N-isopropylpropanamide formate
(2S)-N-[2-(Acetylamino)ethyl]-2-((3S)-3-{(2-amino-2-oxoethyl)[(6-chloronaphth-2-yl)sulfonyl]amino}-2-oxopyrrolidin-1-yl)-N-isopropylpropanamide
(2S)-2-((3S)-3-{[(6-Chloro-2-naphthyl)sulfonyl]amino}-2-oxopyrrolidin-1-yl)-N-cyclopentyl-N-methylpropanamide
(2S)-2-((3S)-3-{[(6-Chloro-2-naphthyl)sulfonyl]amino}-2-oxopyrrolidin-1-yl)-N-cyclohexyl-N-ethylpropanamide
(2S)-2-((3S)-3-{[(6-Chloro-2-naphthyl)sulfonyl]amino}-2-oxopyrrolidin-1-yl)-N-cyclohexyl-N-methylpropanamide
(2S)-2-((3S)-3-{[(6-Chloro-2-naphthyl)sulfonyl]amino}-2-oxopyrrolidin-1-yl)-N-(2-cyanoethyl)-N-cyclopentylpropanamide
(2S)-2-((3S)-3-{[(6-Chloro-2-naphthyl)sulfonyl]amino}-2-oxopyrrolidin-1-yl)-N-(2-cyanoethyl)-N-cyclopropylpropanamide
(2S)-2-((3S)-3-{(2-Amino-2-oxoethyl)[(6-chloro-2-naphthyl)sulfonyl]amino}-2-oxopyrrolidin-1-yl)-N-methyl-N-(1-methylpiperidin-4-yl)propanamide formate
(2S)-2-((3S)-3-{[(6-Chloro-2-naphthyl)sulfonyl]amino}-2-oxopyrrolidin-1-yl)-N-ethyl-N-phenylpropanamide
(2S)-2-((3S)-3-{(2-Amino-2-oxoethyl)[(6-chloro-2-naphthyl)sulfonyl]amino}-2-oxopyrrolidin-1-yl)-N-(2-cyanoethyl)-N-cyclopentylpropanamide
(2S)-2-((3S)-3-{[(6-Chloro-2-naphthyl)sulfonyl]amino}-2-oxopyrrolidin-1-yl)-N-(2-cyanoethyl)-N-cyclohexylpropanamide
(2S)-2-((3S)-3-{(2-Amino-2-oxoethyl)[(6-chloro-2-naphthyl)sulfonyl]amino}-2-oxopyrrolidin-1-yl)-N-cyclohexyl-N-methylpropanamide
(2S)-2-((3S)-3-{(2-Amino-2-oxoethyl)[(6-chloro-2-naphthyl)sulfonyl]amino}-2-oxopyrrolidin-1-yl)-N-(2-cyanoethyl)-N-cyclopropylpropanamide
(2S)-2-((3S)-3-{[(6-Chloro-2-naphthyl)sulfonyl]amino}-2-oxopyrrolidin-1-yl)-N-cyanoethyl-N-cyclobutylpropanamide
(2S)-2-((3S)-3-{[(6-Chloro-2-naphthyl)sulfonyl]amino}-2-oxopyrrolidin-1-yl)-N-cyclopropyl-N-(pyridin-4-ylmethyl)propanamide
(2S)-2-((3S)-3-{(2-Amino-2-oxoethyl)[(6-chloro-2-naphthyl)sulfonyl]amino}-2-oxopyrrolidin-1-yl)-N-cyclopropyl-N-(pyridin-4-ylmethyl)propanamide
(2S)-N-[2-(Aminosulfonyl)ethyl]-2-((3S)-3-{[(6-chloro-2-naphthyl)sulfonyl]amino}-2-oxopyrrolidin-1-yl)-N-isopropylpropanamide (2S)-2-((3S)-3-{(2-Amino-2-oxoethyl)[(6-chloro-2-naphthyl)sulfonyl]amino}-2-oxopyrrolidin-1-yl)-N-isopropyl-N-(2-piperidin-1-ylethyl)propanamide
(2S)-2-((3S)-3-{(2-Amino-2-oxoethyl)[(6-chloro-2-naphthyl)sulfonyl]amino}-2-oxopyrrolidin-1-yl)-N-isopropyl-N-(2-morpholin-4-ylethyl)propanamide
(2S)-2-((3S)-3-{[(6-Chloro-2-naphthyl)sulfonyl]amino}-2-oxopyrrolidin-1-yl)-N-isopropyl-N-(2-piperidin-1-ylethyl)propanamide
(2S)-2-((3S)-3-{[(6-Chloro-2-naphthyl)sulfonyl]amino}-2-oxopyrrolidin-1-yl)-N-isopropyl-N-(2-morpholin-4-ylethyl)propanamide
(2S)-2-((3S)-3-{(2-Amino-2-oxoethyl)[(6-chloro-2-naphthyl)sulfonyl]amino}-2-oxopyrrolidin-1-yl)-N-cyclohexyl-N-ethylpropanamide
(2S)-2-((3S)-3-{(2-Amino-2-oxoethyl)[(6-chloro-2-naphthyl)sulfonyl]amino}-2-oxopyrrolidin-1-yl)-N-(2-hydroxy-2-phenylethyl)-N-methylpropanamide
(2S)-2-((3S)-3-{(2-Amino-2-oxoethyl)[(6-chloro-2-naphthyl)sulfonyl]amino}-2-oxopyrrolidin-1-yl)-N-ethyl-N-phenylpropanamide
(2S)-2-((3S)-3-{[(6-Chloro-2-naphthyl)sulfonyl]amino}-2-oxopyrrolidin-1-yl)-N-(2-hydroxy-2-phenylethyl)-N-methylpropanamide
(2S)-2-((3S)-3-{[(6-Chloro-2-naphthyl)sulfonyl]amino}-2-oxopyrrolidin-1-yl)-N,N-bis(2-hydroxyethyl)propanamide
(2S)-2-((3S)-3-{[(6-Chloro-2-naphthyl)sulfonyl]amino}-2-oxopyrrolidin-1-yl-isopropyl-N-(1H-pyrazol-3-ylmethyl)propanamide
(2S)-N-Allyl-2-((3S)-3-{[(6-chloro-2-naphthyl)sulfonyl]amino}-2-oxopyrrolidin-1-yl)-N-(pyridin-4-ylmethyl)propanamide
(2S)-2-((3S)-3-{[(6-Chloro-2-naphthyl)sulfonyl]amino}-2-oxopyrrolidin-1-yl)-N-isopropyl-N-[3-(4-methylpiperazin-1-yl)propyl]propanamide formate
tert-Butyl 2-[[(2S)-2-((3S)-3-{(2-amino-2-oxoethyl)[(6-chloro-2-naphthyl)sulfonyl]amino}-2-oxopyrrolidin-1-yl)propanoyl](isopropyl)amino]ethylcarbamate
tert-Butyl 3-[[(2S)-2-((3S)-3-{[(6-chloro-2-naphthyl)sulfonyl]amino}-2-oxopyrrolidin-1-yl)propanoyl](isopropyl)amino]propylcarbamate
tert-Butyl 2-[[(2S)-2-((3S)-3-{[(6-chloro-2-naphthyl)sulfonyl]amino}-2-oxopyrrolidin-1-yl)propanoyl](cyclopropylmethyl)amino]ethylcarbamate
(2S)-2-((3S)-3-{(2-Amino-2-oxoethyl)[(6-chloro-2-naphthyl)sulfonyl]amino}-2-oxopyrrolidin-1-yl)-N-isopropylpropanamide
(2S)-N-(2-tert-Butoxyethyl)-2-((3S)-3-{[(6-chloro-2-naphthyl)sulfonyl]amino}-2-oxopyrrolidin-1-yl)-N-(pyridin-4-ylmethyl)propanamide
(2S)-2-((3S)-3-{[(6-Chloro-2-naphthyl)sulfonyl]amino}-2-oxopyrrolidin-1-yl)-N-(2-hydroxyethyl)-N-(pyridin-4-ylmethyl)propanamide formate
(2S)-N-(2-Aminoethyl)-2-((3S)-3-{(2-amino-2-oxoethyl)[(6-chloro-2-naphthyl)sulfonyl]amino}-2-oxopyrrolidin-1-yl)-N-isopropylpropanamide hydrochloride
(2S)-N-(3-Aminopropyl)-2-((3S)-3-{[(6-chloro-2-naphthyl)sulfonyl]amino}-2-oxopyrrolidin-1-yl)-N-isopropylpropanamide hydrochloride
(2S)-N-(2-Aminoethyl)-2-((3S)-3-{[(6-chloro-2-naphthyl)sulfonyl]amino}-2-oxopyrrolidin-1-yl)-N-(cyclopropylmethyl)propanamide hydrochloride
(2S)-N-(2-Aminoethyl)-2-((3S)-3-{[(6-chloro-2-naphthyl)sulfonyl]amino}-2-oxopyrrolidin-1-yl)-N-isopropylpropanamide
(2S)-N-(2-Amino-2-oxoethyl)-2-((3S)-3-{[(6-chloro-2-naphthyl)sulfonyl]amino}-2-oxopyrrolidin-1-yl)-N-isopropylpropanamide
(2S)-2-((3S)-3-{[(6-Chloro-2-naphthyl)sulfonyl]amino}-2-oxopyrrolidin-1-yl)-N-isopropyl-N-{2-[(methylsulfonyl)amino]ethyl}propanamide
(2S)-2-((3S)-3-{(2-Amino-2-oxoethyl)[(6-chloro-2-naphthyl)sulfonyl]amino}-2-oxopyrrolidin-1-yl)-N-isopropyl-N-{2-[(methylsulfonyl)amino]ethyl}propanamide
(2S)-2-((3S)-3-{[(6-Chloro-2-naphthyl)sulfonyl]amino}-2-oxopyrrolidin-1-yl)-N-isopropyl-N-{3-[(methylsulfonyl)amino]propyl}propanamide
(2S)-2-((3S)-3-{[(6-Chloro-2-naphthyl)sulfonyl]amino}-2-oxopyrrolidin-1-yl)-N-(cyclopropylmethyl)-N-{2-[(methylsulfonyl)amino]ethyl}propanamide
(2S)-N-[2-({(E)-Amino[oxido(oxo)hydrazono]methyl}amino)ethyl]-2-((3S)-3-{[(6-chloro-2-naphthyl)sulfonyl]amino}-2-oxopyrrolidin-1-yl)-N-isopropylpropanamide
(2S)-N-[2-({(E)-Amino[oxido(oxo)hydrazono]methyl}amino)ethyl]-2-((3S)-3-{(2-amino-2-oxoethyl)[(6-chloro-2-naphthyl)sulfonyl]amino}-2-oxopyrrolidin-1-yl)-N-isopropylpropanamide
(2S)-N-[3-({(E)-Amino[oxido(oxo)hydrazono]methyl}amino)propyl]-2-((3S)-3-{[(6-chloro-2-naphthyl)sulfonyl]amino}-2-oxopyrrolidin-1-yl)-N-isopropylpropanamirde
(2S)-2-((3S)-3-{[(6-Chloro-2-naphthyl)sulfonyl]amino}-2-oxopyrrolidin-1-yl)-N-isopropyl-N-[2-(methylamino)ethyl]propanamide
(2S)-2-((3S)-3-{[(6-Chloro-2-naphthyl)sulfonyl]amino}-2-oxopyrrolidin-1-yl)-N-[2-(dimethylamino)ethyl]-N-isopropylpropanamide
(2S)-N-{2-[(Aminocarbonyl)amino]ethyl}-2-((3S)-3-{[(6-chloro-2-naphthyl)sulfonyl]amino}-2-oxopyrrolidin-1-yl)-N-isopropylpropanamide
(2S)-N-{2-[(Aminocarbonyl)amino]ethyl}-2-((3S)-3-{(2-amino-2-oxoethyl)[(6-chloro-2-naphthyl)sulfonyl]amino}-2-oxopyrrolidin-1-yl)-N-isopropylpropanamide
(2S)-N-{2-[(Aminocarbonyl)amino]ethyl}-2-((3S)-3-{[(6-chloro-2-naphthyl)sulfonyl]amino}-2-oxopyrrolidin-1-yl)-N-(cyclopropylmethyl)propanamide
(2S)-N-{3-[(Aminocarbonyl)amino]propyl}-2-((3S)-3-{[(6-chloro-2-naphthyl)sulfonyl]amino}-2-oxopyrrolidin-1-yl)-N-isopropylpropanamide
(2S)-2-((3S)-3-{[(6-Chloro-2-naphthyl)sulfonyl]amino}-2-oxopyrrolidin-1-yl)-N-(cyclopropylmethyl)-N-(2-hydroxyethyl)propanamide
(2S)-2-((3S)-3-{[(5'-Chloro-2,2'-bithien-5-yl)sulfonyl]amino}-2-oxopyrrolidin-1-yl)-N-ethyl-N-isopropylpropanamide
(2S)-2-((3S)-3-{[(6-Chloro-1-benzothien-2-yl)sulfonyl]amino}-2-oxopyrrolidin-1-yl)-N-ethyl-N-isopropylpropanamide
(2S)-2-[(3S)-3-({[(E)-2-(5-Chlorothien-2-yl)ethenyl]sulfonyl}amino)-2-oxopyrrolidin-1-yl]-N-ethyl-N-isopropylpropanamide
(2S)-2-[(3S)-3-({[(E)-2-(4-Chlorobenyl)ethenyl]sulfonyl}amino)-2-oxopyrrolidin-1-yl]-N-ethyl-N-isopropylpropanamide
tert-Butyl 2-{[(2S)-2-((3S)-3-{[(6-chloro-2-naphthyl)sulfonyl]amino}-2-oxopyrrolidin-1-yl)propanoyl]amino}ethylcarbamate
(2S)-2-((3S)-3-{[(6-Chloro-2-naphthyl)sulfonyl]amino}-2-oxopyrrolidin-1-yl)-N-(2-piperidin-1-ylethyl)propanamide (2S)-N-(2-Aminoethyl)-2-((3S)-3-{[(6-chloro-2-naphthyl)sulfonyl]amino}-2-oxopyrrolidin-1-yl)propanamide hydrochloride (2S)-2-((3S)-{(2-Amino-2-oxoethyl)-3-({[(E)-2-(5-chlorothien-2-yl)ethenyl]sulfonyl}amino)-2-oxopyrrolidin-1-yl)-N-ethyl-N-isopropylpropanamide (2S)-2-((3S)-{(2-Amino-2-oxoethyl)-3-({[(6-chloro-1-benzothien-2-yl)sulfonyl]amino)-2-oxopyrrolidin-1-yl)-N-ethyl-N-isopropylpropanamide.

More preferred compounds of the invention include:

(2S)-2-((3S)-3-{[(6-Chloro-2-naphthyl)sulfonyl]amino}-2-oxopyrrolidin-1-yl)-N,N-diethylpropanamide (2S)-2-((3S)-3-{[(6-Chloro-2-naphthyl)sulfonyl]amino}-2-oxopyrrolidin-1-yl)-N-ethyl-N-(pyridin-4-ylmethyl)propanamide (2S)-2-((3S)-3-{[(6-Chloro-2-naphthyl)sulfonyl]amino}-2-oxopyrrolidin-1-yl)-N-ethyl-N-methylpropanamide (2S)-2-((3S)-3-{[(6-Chloro-2-naphthyl)sulfonyl]amino}-2-oxopyrrolidin-1-yl)-N-methyl-N-(2-phenylethyl)propanamide (2S)-2-((3S)-3-{[(6-Chloro-2-naphthyl)sulfonyl]amino}-2-oxopyrrolidin-1-yl)-N-ethyl-N-(2-phenylethyl)propanamide (2S)-2-((3S)-3-{[(6-Chloro-2-naphthyl)sulfonyl]amino}-2-oxopyrrolidin-1-yl)-N,N-dipropylpropanamide (2S)-2-((3S)-3-{[(6-Chloro-2-naphthyl)sulfonyl]amino}-2-oxopyrrolidin-1-yl)-N-ethyl-N-isopropylpropanamide (2S)-2-((3S)-3-{[(6-chloro-2-naphthyl)sulfonyl]amino}-2-oxopyrrolidin-1-yl)-N-methyl-N-(2-pyridin-2-ylethyl)propanamide (2S)-2-((3S)-3-{[(6-Chloro-2-naphthyl)sulfonyl]amino}-2-oxopyrrolidin-1-yl)-N-methyl-N-(pyridin-3-ylmethyl)propanamide (2S)-2-((3S)-3-{[(6-chloro-2-naphthyl)sulfonyl]amino}-2-oxopyrrolidin-1-yl)-N-isopropyl-N-(pyridin-4-ylmethyl)propanamide (2S)-2-((3S)-3-{[(6-Chloro-2-naphthyl)sulfonyl]amino}-2-oxopyrrolidin-1-yl)-N-isobutyl-N-(pyridin-2-ylmethyl)propanamide (2S)-2-((3S)-3-{[(6-chloro-2-naphthyl)sulfonyl]amino}-2-oxopyrrolidin-1-yl)-N-propyl-N-(pyridin-2-ylmethyl)propanamide (2S)-2-((3S)-3-{[(6-Chloro-2-naphthyl)sulfonyl]amino}-2-oxopyrrolidin-1-yl)-N-isopropyl-N-(pyridin-3-ylmethyl)propanamide (2S)-N-(2-Azepan-1-ylethyl)-2-((3S)-3-{[(6-chloro-2-naphthyl)sulfonyl]amino}-2-oxopyrrolidin-1-yl)-N-isopropylpropanamide formate (2S)-2-((3S)-3-{[(6-Chloro-2-naphthyl)sulfonyl]amino}-2-oxopyrrolidin-1-yl)-N-(2-cyanoethyl)-N-isopropylpropanamide (2S)-2-((3S)-3-{[(6-Chloro-2-naphthyl)sulfonyl]amino}-2-oxopyrrolidin-1-yl)propanoyl)-N-isopropyl-beta-alainamide (2S)-2-((3S)-3-{[(6-Chloro-2-naphthyl)sulfonyl]amino}-2-oxopyrrolidin-1-yl)-N-(2-hydroxyethyl)-N-isopropylpropanamide (2S)-2-((3S)-3-{[(6-Chloro-2-naphthyl)sulfonyl]amino}-2-oxopyrrolidin-1-yl)-N-(2-cyanoethyl)-N-(cyclopropylmethyl)propanamide (2S)-2-((3S)-3-{[(6-Chloro-2-naphthyl)sulfonyl]amino}-2-oxopyrrolidin-1-yl)-N-(2-cyanoethyl)-N-isobutylpropanamide (2S)-2-((3S)-3-{[(6-Chloro-2-naphthyl)sulfonyl]amino}-2-oxopyrrolidin-1-yl)-N-isopropyl-N-methylpropanamide (2S)-2-((3S)-3-{[(6-Chloro-2-naphthyl)sulfonyl]amino}-2-oxopyrrolidin-1-yl)-N-ethyl-N-(3-hydroxypropyl)propanamide (2S)-2-((3S)-3-{[(6-Chloro-2-naphthyl)sulfonyl]amino}-2-oxopyrrolidin-1-yl)-N-methyl-N-(2-pyrrolidin-1-ylethyl)propanamide formate (2S)-2-((3S)-3-{[(6-Chloro-2-naphthyl)sulfonyl]amino}-2-oxopyrrolidin-1-yl)-N-ethyl-N-(2-morpholin-4-ylethyl)propanamide formate (2S)-2-((3S)-3-{[(6-Chloro-2-naphthyl)sulfonyl]amino}-2-oxopyrrolidin-1-yl)-N-[2-(dimethylamino)ethyl]-N-ethylpropanamide formate (2S)-2-((3S)-3-{[(6-Chloro-2-naphthyl)sulfonyl]amino}-2-oxopyrrolidin-1-yl)-N-isopropyl-N-(pyridin-2-ylmethyl)propanamide (2S)-2-((3S)-3-{[(6-Chloro-2-naphthyl)sulfonyl]amino}-2-oxopyrrolidin-1-yl)-N-ethyl-N-(2-pyridin-2-ylethyl)propanamide (2S)-2-((3S)-3-{[(6-Chloro-2-naphthyl)sulfonyl]amino}-2-oxopyrrolidin-1-yl)-N-methyl-N-(pyridin-2-ylmethyl)propanamide (2S)-2-((3S)-3-{[(6-Chloro-2-naphthyl)sulfonyl]amino}-2-oxopyrrolidin-1-yl)-N-methyl-N-(2-pyridin-4-ylethyl)propanamide (2S)-2-((3S)-3-{[(6-Chloro-2-naphthyl)sulfonyl]amino}-2-oxopyrrolidin-1-yl)-N-methyl-N-(pyridin-4-ylmethyl)propanamide (2S)-2-((3S)-3-{[(6-Chloro-2-naphthyl)sulfonyl]amino}-2-oxopyrrolidin-1-yl)-N-[2-(1H-imidazol-4-yl)ethyl]-N-methylpropanamide formate (2S)-2-((3S)-3-{[(6-Chloro-2-naphthyl)sulfonyl]amino}-2-oxopyrrolidin-1-yl)-N-(2-cyanoethyl)-N-(pyridin-3-ylmethyl)propanamide (2S)-2-((3S)-3-{[(6-Chloro-2-naphthyl)sulfonyl]amino}-2-oxopyrrolidin-1-yl)-N-ethyl-N-(2-hydroxyethyl)propanamide (2S)-2-((3S)-3-{[(6-Chloro-2-naphthyl)sulfonyl]amino}-2-oxopyrrolidin-1-yl)-N-(2-methoxyethyl)-N-methylpropanamide (2S)-2-((3S)-3-{[(6-Chloro-2-naphthyl)sulfonyl]amino}-2-oxopyrrolidin-1-yl)-N-ethyl-N-(2-piperidin-1-ylethyl)propanamide formate (2S)-2-((3S)-3-{[(6-Chloro-2-naphthyl)sulfonyl]amino}-2-oxopyrrolidin-1-yl)-N-isopropyl-N-(2-pyridin-2-ylethyl)propanamide (2S)-2-((3S)-3-{[(6-Chloro-2-naphthyl)sulfonyl]amino}-2-oxopyrrolidin-1-yl)-N-(2-hydroxypropyl)-N-isopropylpropanamide (2S)-2-((3S)-3-{[(6-Chloro-2-naphthyl)sulfonyl]amino}-2-oxopyrrolidin-1-yl)-N-(cyanomethyl)-N-isopropylpropanamide formate (2S)-2-((3S)-3-{[(6-Chloro-2-naphthyl)sulfonyl]amino}-2-oxopyrrolidin-1-yl)-N-isopropyl-N-(3-methoxypropyl)propanamide (2S)-2-((3S)-3-{[(6-Chloro-2-naphthyl)sulfonyl]amino}-2-oxopyrrolidin-1-yl)-N-isopropyl-N-(2-methoxyethyl)propanamide (2S)-N-[2-(Acetylamino)ethyl]-2-((3S)-3-{[(6-chloro-2-naphthyl)sulfonyl]amino}-2-oxopyrrolidin-1-yl)-N-isopropylpropanamide (2S)-N-Benzyl-2-((3S)-3-{[(6-chloro-2-naphthyl)sulfonyl]amino}-2-oxopyrrolidin-1-yl)-N-isopropylpropanamide (2S)-2-((3S)-3-{[(6-Chloro-2-naphthyl)sulfonyl]amino}-2-oxopyrrolidin-1-yl)-N-isopropyl-N-(thien-2-ylmethyl)propanamide (2S)-2-((3S)-3-{[(6-Chloro-2-naphthyl)sulfonyl]amino}-2-oxopyrrolidin-1-yl)-N-(3-hydroxypropyl)-N-isopropylpropanamide (2S)-2-((3S)-3-{[(6-Chloro-2-naphthyl)sulfonyl]amino}-2-oxopyrrolidin-1-yl)-N-(2-hydroxyethyl)-N-isopropylpropanamide (2S)-2-((3S)-3-{[(6-Chloro-2-naphthyl)sulfonyl]amino}-2-oxopyrrolidin-1-yl)-N-(3-hydroxypropyl)-N-(pyridin-4-ylmethyl)propanamide (2S)-2-((3S)-3-{[(6-Chloro-2-naphthyl)sulfonyl]amino}-2-oxopyrrolidin-1-yl)-N-(3-hydroxypropyl)-N-(pyridin-3-ylmethyl)propanamide (2S)-2-((3S)-3-{[(6-Chloro-2-naphthyl)sulfonyl]amino}-2-oxopyrrolidin-1-yl)-N-(3-hydroxypropyl)-N-(pyridin-2-ylmethyl)propanamide (2S)-2-((3S)-3-{[(6-Chloro-2-naphthyl)sulfonyl]amino}-2-oxopyrrolidin-1-yl)-N-(2-cyanoethyl)-N-(tetrahydrofuran-2-ylmethyl)propanamide (2S)-2-((3S)-3-{[(6-Chloro-2-naphthyl)sulfonyl]amino}-2-oxopyrrolidin-1-yl)-N-(2-cyanoethyl)-N-(cyclopropylmethyl)propanamide (2S)-2-((3S)-3-{[(6-Chloro-2-naphthyl)sulfonyl]amino}-2-oxopyrrolidin-1-yl)-N-(2-cyanoethyl)-N-(2-pyridin-2-ylethyl)propanamide (2S)-2-((3S)-3-{[(6-Chloro-2-naphthyl)sulfonyl]amino}-2-oxopyrrolidin-1-yl)-N-(2-cyanoethyl)-N-isobutylpropanamide (2S)-2-((3S)-3-{(2-Amino-2-oxoethyl)[(6-chloro-2-naphthyl)sulfonyl]amino}-2-oxopyrrolidin-1-yl)-N-ethyl-N-(pyridin-4-ylmethyl)propanamide (2S)-2-((3S)-3-{(2-Amino-2-oxoethyl)[(6-chloro-2-naphthyl)sulfonyl]amino}-2-oxopyrrolidin-1-yl)-N-ethyl-N-(2-pyridin-2-ylethyl)propanamide (2S)-2-((3S)-3-{(2-amino-2-oxoethyl)[(6-chloro-2-naphthyl)sulfonyl]amino}-2-oxopyrrolidin-1-yl)-N-ethyl-N-(2-hydroxyethyl)propanamide (2S)-2-((3S)-3-{(2-Amino-2-oxoethyl)[(6-chloro-2-naphthyl)sulfonyl]amino}-2-oxopyrrolidin-1-yl)-N-isopropyl-N-(pyridin-2-ylmethyl)propanamide (2S)-2-((3S)-3-{(2-Amino-2-oxoethyl)[(6-chloro-2-naphthyl)sulfonyl]amino}-2-oxopyrrolidin-1-yl)-N-methyl-N-(pyridin-2-ylmethyl)propanamide (2S)-2-((3S)-3-{(2-Amino-2-oxoethyl)[(6-chloro-2-naphthyl)sulfonyl]amino}-2-oxopyrrolidin-1-yl)-N-methyl-N-(pyridin-3-ylmethyl)propanamide (2S)-2-((3S)-3-{(2-Amino-2-oxoethyl)[(6-chloro-2-naphthyl)sulfonyl]amino}-2-oxopyrrolidin-1-yl)-N-methyl-N-(2-pyridin-4-ylethyl)propanamide (2S)-2-((3S)-3-{(2-Amino-2-oxoethyl)[(6-chloro-2-naphthyl)sulfonyl]amino}-2-oxopyrrolidin-1-yl)-N-methyl-N-(pyridin-4-ylmethyl)propanamide (2S)-2-((3S)-3-{(2-Amino-2-oxoethyl)[(6-chloro-2-naphthyl)sulfonyl]amino}-2-oxopyrrolidin-1-yl)-N-[2-(1H-imidazol-4-yl)ethyl]-N-methylpropanamide formate (2S)-2-((3S)-3-{(2-Amino-2-oxoethyl)[(6-chloro-2-naphthyl)sulfonyl]amino}-2-oxopyrrolidin-1-yl)-N-methyl-N-(2-pyridin-2-ylethyl)propanamide (2S)-2-((3S)-3-{(2-Amino-2-oxoethyl)[(6-chloro-2-naphthyl)sulfonyl]amino}-2-oxopyrrolidin-1-yl)-N-methyl-N-(2-phenylethyl)propanamide (2S)-2-((3S)-3-{(2-Amino-2-oxoethyl)[(6-chloro-2-naphthyl)sulfonyl]amino}-2-oxopyrrolidin-1-yl)-N-ethyl-N-(2-phenylethyl)propanamide (2S)-2-((3S)-3-{(2-Amino-2-oxoethyl)[(6-chloro-2-naphthyl)sulfonyl]amino}-2-oxopyrrolidin-1-yl)-N,N-dimethylpropanamide (2S)-2-((3S)-3-{(2-Amino-2-oxoethyl)[(6-chloro-2-naphthyl)sulfonyl]amino}-2-oxopyrrolidin-1-yl)-N-isopropyl-N-methylpropanamide (2S)-2-((3S)-3-{(2-Amino-2-oxoethyl)[(6-chloro-2-naphthyl)sulfonyl]amino}-2-oxopyrrolidin-1-yl)-N-(2-hydroxyethyl)-N-methylpropanamide (2S)-2-((3S)-3-{(2-Amino-2-oxoethyl)[(6-chloro-2-naphthyl)sulfonyl]amino}-2-oxopyrrolidin-1-yl)-N-(2-hydroxyethyl)-N-isopropylpropanamide (2S)-2-((3S)-3-{(2-Amino-2-oxoethyl)[(6-chloro-2-naphthyl)sulfonyl]amino}-2-oxopyrrolidin-1-yl)-N-(2-cyanoethyl)-N-methylpropanamide (2S)-N-(2-Amino-2-oxoethyl)-2-((3S)-3-{(2-amino-2-oxoethyl)[(6-chloro-2-naphthyl)sulfonyl]amino}-2-oxopyrrolidin-1-yl)-N-methylpropanamide (2S)-2-((3S)-3-{(2-Amino-2-oxoethyl)[(6-chloro-2-naphthyl)sulfonyl]amino}-2-oxopyrrolidin-1-yl)-N-ethyl-N-(3-hydroxypropyl)propanamide (2S)-2-((3S)-3-{(2-Amino-2-oxoethyl)[(6-chloro-2-naphthyl)sulfonyl]amino}-2-oxopyrrolidin-1-yl)-N-methyl-N-(2-pyrrolidin-1-ylethyl)propanamide formate (2S)-2-((3S)-3-{(2-Amino-2-oxoethyl)[(6-chloro-2-naphthyl)sulfonyl]amino}-2-oxopyrrolidin-1-yl)-N-methyl-N-(2-morpholin-4-ylethyl)propanamide formate (2S)-2-((3S)-3-{(2-Amino-2-oxoethyl)[(6-chloro-2-naphthyl)sulfonyl]amino}-2-oxopyrrolidin-1-yl)-N-ethyl-N-(2-morpholin-4-ylethyl)propanamide formate (2S)-2-((3S)-3-{(2-Amino-2-oxoethyl)[(6-chloro-2-naphthyl)sulfonyl]amino}-2-oxopyrrolidin-1-yl)-N-[2-(dimethylamino)ethyl]-N-ethylpropanamide formate (2S)-2-((3S)-3-{(2-Amino-2-oxoethyl)[(6-chloro-2-naphthyl)sulfonyl]amino}-2-oxopyrrolidin-1-y)-N-(2-cyanoethyl)-N-(pyridin-3-ylmethyl)propanamide (2S)-2-((3S)-3-{(2-Amino-2-oxoethyl)[(6-chloro-2-naphthyl)sulfonyl]amino}-2-oxopyrrolidin-1-yl)-N-ethyl-N-(2-hydroxyethyl)propanamide (2S)-2-((3S)-3-{(2-Amino-2-oxoethyl)[(6-chloro-2-naphthyl)sulfonyl]amino}-2-oxopyrrolidin-1-yl)-N-(2-methoxyethyl)-N-methylpropanamide (2S)-2-((3S)-3-{(2-Amino-2-oxoethyl)[(6-chloro-2-naphthyl)sulfonyl]amino}-2-oxopyrrolidin-1-yl)-N-ethyl-N-(2-piperidin-1-ylethyl)propanamide formate (2S)-2-((3S)-3-{(2-Amino-2-oxoethyl)[(6-chloro-2-naphthyl)sulfonyl]amino}-2-oxopyrrolidin-1-yl)-N-(2-hydroxyethyl)-N-(2-morpholin-4-ylethyl)propanamide formate (2S)-2-((3S)-3-{(2-Amino-2-oxoethyl)[(6-chloronaphth-2-yl)sulfonyl]amino}-2-oxopyrrolidin-1-yl)-N-ethyl-N-methylpropanamide (2S)-2-((3S)-3-{(2-Amino-2-oxoethyl)[(6-chloronaphth-2-yl)sulfonyl]amino}-2-oxopyrrolidin-1-yl)-N,N-diethylpropanamide (2S)-2-((3S)-3-{(2-Amino-2-oxoethyl)[(6-chloronaphth-2-yl)sulfonyl]amino}-2-oxopyrrolidin-1-yl)-N,N-dipropylpropanamide (2S)-2-((3S)-3-{(2-Amino-2-oxoethyl)[(6-chloronaphth-2-yl)sulfonyl]amino}-2-oxopyrrolidin-1-yl)-N-ethyl-N-isopropylpropanamide (2S)-2-((3S)-3-{(2-Amino-2-oxoethyl)[(6-chloronaphth-2-yl)sulfonyl]amino}-2-oxopyrrolidin-1-yl)-N-isopropyl-N-(pyrid-4-ylmethyl)propanamide (2S)-2-((3S)-3-{(2-Amino-2-oxoethyl)[(6-chloronaphth-2-yl)sulfonyl]amino}-2-oxopyrrolidin-1-yl)-N-(2-cyanoethyl)-N-isopropylpropanamide (2S)-2-((3S)-3-{(2-Amino-2-oxoethyl)[(6-chloronaphth-2-yl)sulfonyl]amino}-2-oxopyrrolidin-1-yl)-N-(2-azepan-1-ylethyl)-N-isopropylpropanamide formate (2S)-N-[2-(Acetylamino)ethyl]-2-((3S)-3-{(2-amino-2-oxoethyl)[(6-chloronaphth-2-yl)sulfonyl]amino}-2-oxopyrrolidin-1-yl)-N-isopropylpropanamide (2S)-2-((3S)-3-{[(6-Chloro-2-naphthyl)sulfonyl]amino}-2-oxopyrrolidin-1-yl)-N-cyclopentyl-N-methylpropanamide (2S)-2-((3S)-3-{[(6-Chloro-2-naphthyl)sulfonyl]amino}-2-oxopyrrolidin-1-yl-cyclohexyl-N-ethylpropanamide (2S)-2-((3S)-3-{[(6-Chloro-2-naphthyl)sulfonyl]amino}-2-oxopyrrolidin-1-yl)-N-(2cyanoethyl)-N-cyclopentylpropanamide (2S)-2-((3S)-3-{[(6-Chloro-2-naphthyl)sulfonyl]amino}-2-oxopyrrolidin-1-yl)-N-(2cyanoethyl)-N-cyclopropylpropanamide (2S)-2-((3S)-3-{(2-Amino-2-oxoethyl)[(6-chloro-2-naphthyl)sulfonyl]amino}-2-oxopyrrolidin-1-yl)-N-methyl-N-(1-methylpiperidin-4-yl)propanamide formate (2S)-2-((3S)-3-{([(6-Chloro-2-naphthyl)sulfonyl]amino}-2-oxopyrrolidin-1-yl)-N-ethyl-N-phenylpropanamide (2S)-2{(3S)-3-{(2-Amino-2-oxoethyl)[(6-chloro-2-naphthyl)sulfonyl]amino}-2-oxopyrrolidin-1-yl)-N-(2-cyanoethyl)-N-cyclopentylpropanamide (2S)-2-((3S)-3-{[(6-Chloro-2-naphthyl)sulfonyl]amino}-2-oxopyrrolidin-1-yl)-N-(2-cyanoethyl)-N-cyclohexylpropanamide (2S)-2-((3S)-3-{(2-Amino-2-oxoethyl)[(6-chloro-2-naphthyl)sulfonyl]amino}-2-oxopyrrolidin-1-yl)-N-cyclohexyl-N-methylpropanamide (2S)-2-((3S)-3-{(2-Amino-2-oxoethyl)[(6-chloro-2-naphthyl)sulfonyl]amino}-2-oxopyrrolidin-1-yl)-N-(2-cyanoethyl)-N-cyclopropylpropanamide (2S)-2-((3S)-3-{[(6-Chloro-2-naphthyl)sulfonyl]amino}-2-oxopyrrolidin-1-yl)-N-(2-cyanoethyl)-N-cyclobutylpropanamide (2S)-2-((3S)-3-{[(6-Chloro-2-naphthyl)sulfonyl]amino}-2-oxopyrrolidin-1-yl)-N-cyclopropyl-N-(pyridin-4-ylmethyl)propanamide (2S)-2-((3S)-3-(2-Amino-2-oxoethyl)[(6-chloro-2-naphthyl)sulfonyl]amino}-2-oxopyrrolidin-1-yl)-N-cyclopropyl-N-(pyridin-4-ylmethyl)propanamide (2S)-N-[2-(Aminosulfonyl)ethyl]-2-((3S)-3-{[(6-chloro-2-naphthyl)sulfonyl]amino}-2-oxopyrrolidin-1-yl)-N-isopropylpropanamide (2S)-2-((3S)-3-{(2-Amino-2-oxoethyl)[(6-chloro-2-naphthyl)sulfonyl]amino}-2-oxopyrrolidin-1-yl)-N-isopropyl-N-(2-piperidin-1-ylethyl)propanamide (2S)-2-((3S)-3-{(2-Amino-2-oxoethyl)[(6-chloro-2-naphthyl)sulfonyl]amino}-2-oxopyrrolidin-1-yl)-N-isopropyl-N-(2-morpholin-4-ylethyl)propanamide (2S)-2-((3S)-3-{[(6-Chloro-2-naphthyl)sulfonyl]amino}-2-oxopyrrolidin-1-yl)-N-isopropyl-N-(2-piperidin-1-ylethyl)propanamide (2S)-2-((3S)-3-{[(6-Chloro-2-naphthyl)sulfonyl]amino}-2-oxopyrrolidin-1-yl)-N-isopropyl-N-(2-morpholin-4-ylethyl)propanamide (2S)-2-((3S)-3-{(2-Amino-2-oxoethyl)[(6-chloro-2-naphthyl)sulfonyl]amino}-2-oxopyrrolidin-1-yl)-N-cyclohexyl-N-ethylpropanamide (2S)-2-((3S)-3-{(2-Amino-2-oxoethyl)[(6-chloro-2-naphthyl)sulfonyl]amino}-2-oxopyrrolidin-1-yl)-N-(2-hydroxy-2-phenylethyl)-N-methylpropanamide (2S)-2-((3S)-3-{(2-Amino-2-oxoethyl)[(6-chloro-2-naphthyl)sulfonyl]amino}-2-oxopyrrolidin-1-yl)-N-ethyl-N-phenylpropanamide (2S)-2-((3S)-3-{[(6-Chloro-2-naphthyl)sulfonyl]amino}-2-oxopyrrolidin-1-yl)-N-(2-hydroxy-2-phenylethyl)-N-methylpropanamide (2S)-2-((3S)-3-{[(6-Chloro-2-naphthyl)sulfonyl]amino}-2-oxopyrrolidin-1-yl)-N-isopropyl-N-(1H-pyrazol-3-ylmethyl)propanamide (2S)-N-Allyl-2-((3S)-3-{[(6-chloro-2-naphthyl)sulfonyl]amino}-2-oxopyrrolidin-1-N-(pyridin-4-ylmethyl)propanamide (2S)-2-((3S)-3-{[(6-Chloro-2-naphthyl)sulfonyl]amino}-2-oxopyrrolidin-1-yl)-N-isopropyl-N-[3-(4-methylpiperazin-1-yl)propyl]propanamide formate tert-Butyl 2-[[(2S)-2-((3S)-3-{(2-amino-2-oxoethyl)[(6-chloro-2-naphthyl)sulfonyl]amino}-2-oxopyrrolidin-1-yl)propanoyl](isopropyl)amino]ethylcarbamate tert-Butyl 3-[[(2S)-2-((3S)-3-{[(6-chloro-2-naphthyl)sulfonyl]amino}-2-oxopyrrolidin-1-yl)propanoyl](isopropyl)amino]propylcarbamate tert-Butyl 2-[[(2S)-2-((3S)-3-{[(6-chloro-2-naphthyl)sulfonyl]amino}-2-oxopyrrolidin-1-yl)propanoyl](cyclopropylmethyl)amino]ethylcarbamate (2S)-N-(2-tert-Butoxyethyl)-2-((3S)-3-{[(6-chloro-2-naphthyl)sulfonyl]amino}-2-oxopyrrolidin-1-yl)-N-(pyridin-4-ylmethyl)propanamide (2S)-2-((3S)-3-{[(6-Chloro-2-naphthyl)sulfonyl]amino}-2-oxopyrrolidin-1-yl)-N-(2-hydroxyethyl)-N-(pyridin-4-ylmethyl)propanamide formate (2S)-N-(2-Aminoethyl)-2-((3S)-3-{(2-amino-2-oxoethyl)[(6-chloro-2-naphthyl)sulfonyl]amino}-2-oxopyrrolidin-1-yl)-N-isopropylpropanamide hydrochloride (2S)-N-(3-Aminopropyl)-2-((3S)-3-{[(6-chloro-2-naphthyl)sulfonyl]amino}-2-oxopyrrolidin-1-yl)-N-isopropylpropanamide hydrochloride (2S)-N-(2-Aminoethyl)-2-((3S)-3-{[(6-chloro-2-naphthyl)sulfonyl]amino}-2-oxopyrrolidin-1-yl)-N-(cyclopropylmethyl)propanamide hydrochloride (2S)-N-(2-Aminoethyl)-2-((3S)-3-{[(6-chloro-2-naphthyl)sulfonyl]amino}-2-oxopyrrolidin-1-yl)-N-isopropylpropanamide (2S)-N-(2-Amino-2-oxoethyl)-2-((3S)-3-{[(6-chloro-2-naphthyl)sulfonyl]amino}-2-oxopyrrolidin-1-yl)-N-isopropylpropanamide (2S)-2-((3S)-3-{[(6-Chloro-2-naphthyl)sulfonyl]amino}-2-oxopyrrolidin-1-yl)-N-isopropyl-N-{2-[(methylsulfonyl)amino]ethyl}propanamide (2S)-2-((3S)-3-{(2-Amino-2-oxoethyl)[(6-chloro-2-naphthyl)sulfonyl]amino}-2-oxopyrrolidin-1-yl)-N-isopropyl-N-{2-[(methylsulfonyl)amino]ethyl}propanamide (2S)-2-((3S)-3-{[(6-Chloro-2-naphthyl)sulfonyl]amino}-2-oxopyrrolidin-1-yl)-N-isopropyl-N-{3-[(methylsulfonyl)amino]propyl}propanamide (2S)-2-((3S)-3-{[(6-Chloro-2-naphthyl)sulfonyl]amino}-2-oxopyrrolidin-1-yl)-N-(cyclopropylmethyl)-N-{2-[(methylsulfonyl)amino]ethyl}propanamide (2S)-N-[2-({(E)-Amino[oxido(oxo)hydrazono]methyl}amino)ethyl]-2-((3S)-3-{[(6-chloro-2-naphthyl)sulfonyl]amino}-2-oxopyrrolidin-1-yl)-N-isopropylpropanamide (2S)-N-[2-({(E)-Amino[oxido(oxo)hydrazono]methyl}amino)ethyl]-2-((3S)-3-{(2-amino-2-oxoethyl)[(6-chloro-2-naphthyl)sulfonyl]amino}-2-oxopyrrolidin-1-yl)-N-isopropylpropanamide (2S)-N-[3-({(E)-Amino[oxido(oxo)hydrazono]methyl}amino)propyl]-2-((3S)-3-{[(6-chloro-2-naphthyl)sulfonyl]amino}-2-oxopyrrolidin-1-yl)-N-isopropylpropanamide (2S)-2-((3S)-3-{[(6-Chloro-2-naphthyl)sulfonyl]amino}-2-oxopyrrolidin-1-yl)-N-isopropyl-N-[2-(methylamino)ethyl]propanamide (2S)-2-((3S)-3-{[(6-Chloro-2-naphthyl)sulfonyl]amino}-2-oxopyrrolidin-1-yl)-N-[2-(dimethylamino)ethyl]-N-isopropylpropanamide
(2S)-N-{2-[(Aminocarbonyl)amino]ethyl}-2-((3S)-3-{[(6-chloro-2-naphthyl)sulfonyl]amino}-2-oxopyrrolidin-1-yl)-N-isopropylpropanamide
(2S)-N-(2-[(Aminocarbonyl)amino]ethyl)-2-((3S)-3-{(2-amino-2-oxoethyl)[(6-chloro-2-naphthyl)sulfonyl]amino}-2-oxopyrrolidin-1-yl)-N-isopropylpropanamide
(2S)-N-{2-[(Aminocarbonyl)amino]ethyl}-2-((3S)-3-{[(6-chloro-2-naphthyl)sulfonyl]amino}-2-oxopyrrolidin-1-yl)-N-(cyclopropylmethyl)propanamide
(2S)-N-{3-[(Aminocarbonyl)amino]propyl}-2-((3S)-3-{[(6-chloro-2-naphthyl)sulfonyl]amino}-2-oxopyrrolidin-1-yl)-N-isopropylpropanamide
(2S)-2-((3S)-3-{[(6-Chloro-2-naphthyl)sulfonyl]amino}-2-oxopyrrolidin-1-yl)-N-(cyclopropylmethyl)-N-(2-hydroxyethyl)propanamide
(2S)-2-((3S)-3-{[(5'-Chloro-2,2'-bithien-5-yl)sulfonyl]amino}-2-oxopyrrolidin-1-yl)-N-ethyl-N-isopropylpropanamide
(2S)-2-((3S)-3-{[(6-Chloro-1-benzothien-2-yl)sulfonyl]amino}-2-oxopyrrolidin-1-yl)-N-ethyl-N-isopropylpropanamide
(2S)-2-[(3S)-3-({[(E)-2-(5-Chlorothien-2-yl)ethenyl]sulfonyl}amino)-2-oxopyrrolidin-yl]-N-ethyl-N-isopropylpropanamide
(2S)-2-[(3S)-3-({[(E)-2-(4-Chlorophenyl)ethenyl]sulfonyl}amino)-2-oxopyrrolidin-1-yl]-N-ethyl-N-isopropylpropanamide
(2S)-2-((3S)-{(2-Amino-2-oxoethyl)-3-({[(E)-2-(5-chlorothien-2-yl)ethenyl]sulfonyl}amino)-2-oxopyrrolidin-1-yl)-N-ethyl-N-isopropylpropanamide
(2S)-2-((3S)-{(2-Amino-2-oxoethyl)-3-({[(6-chloro-1-benzothien-2-yl)sulfonyl]amino)-2-oxopyrrolidin-1-yl)-N-ethyl-N-isopropylpropanamide.

Even more preferred compounds of the invention include:
(2S)-2-((3S)-3-{[(6-Chloro-2-naphthyl)sulfonyl]amino}-2-oxopyrrolidin-1-yl)-N-ethyl-N-isopropylpropanamide
(2S)-2-((3S)-3-{[(6-chloro-2-naphthyl)sulfonyl]amino}-2-oxopyrrolidin-1-yl)-N-isopropyl-N-(pyridin-4-ylmethyl)propanamide
(2S)-2-((3S)-3-{[(6-Chloro-2-naphthyl)sulfonyl]amino}-2-oxopyrrolidin-1-yl)-N-isopropyl-N-(pyridin-3-ylmethyl)propanamide
(2S)-N-(2-Azepan-1-ylethyl)-2-((3S)-3-{[(6-chloro-2-naphthyl)sulfonyl]amino}-2-oxopyrrolidin-1-yl)-N-isopropylpropanamide formate
(2S)-2-((3S)-3-{[(6-Chloro-2-naphthyl)sulfonyl]amino}-2-oxopyrrolidin-1-yl)-N-(2-cyanoethyl)-N-isopropylpropanamide
(2S)-2-((3S)-3-{[(6-Chloro-2-naphthyl)sulfonyl]amino}-2-oxopyrrolidin-1-yl)propanoyl)-N-isopropyl-beta-alaninamide
(2S)-2-((3S)-3-{[(6-Chloro-2-naphthyl)sulfonyl]amino}-2-oxopyrrolidin-1-yl)-N-(2-hydroxyethyl)-N-isopropylpropanamide
(2S)-2-((3S)-3-{[(6-Chloro-2-naphthyl)sulfonyl]amino}-2-oxopyrrolidin-1-yl)-N-2-cyanoethyl)-N-(cyclopropylmethyl)propanamide
(2S)-2-((3S)-3-{[(6-Chloro-2-naphthyl)sulfonyl]amino}-2-oxopyrrolidin-1-yl)-N-[2-(dimethylamino)ethyl]-N-ethylpropanamide formate
(2S)-2-((3S)-3-{[(6-Chloro-2-naphthyl)sulfonyl]amino}-2-oxopyrrolidin-1-yl)-N-isopropyl-N-(pyridin-2-ylmethyl)propanamide
(2S)-2-((3S)-3-{[(6-Chloro-2-naphthyl)sulfonyl]amino}-2-oxopyrrolidin-1-yl)-N-ethyl-N-(2-piperidin-1-ylethyl)propanamide formate
(2S)-2-((3S)-3-{[(6-Chloro-2-naphthyl)sulfonyl]amino}-2-oxopyrrolidin-1-yl)-N-isopropyl-N-(2-pyridin-2-ylethyl)propanamide
(2S)-2-((3S)-3-{[(6-Chloro-2-naphthyl)sulfonyl]amino}-2-oxopyrrolidin-1-yl)-N-(2-hydroxypropyl)-N-isopropylpropanamide
(2S)-2-((3S)-3-{[(6-Chloro-2-naphthyl)sulfonyl]amino}-2-oxopyrrolidin-1-yl)-N-(cyanomethyl)-N-isopropylpropanamide formate
(2S)-2-((3S)-3-{[(6-Chloro-2-naphthyl)sulfonyl]amino}-2-oxopyrrolidin-1-yl)-N-isopropyl-N-(3-methoxypropyl)propanamide
(2S)-2-((3S)-3-{[(6-Chloro-2-naphthyl)sulfonyl]amino}-2-oxopyrrolidin-1-yl)-N-isopropyl-N-(2-methoxyethyl)propanamide
(2S)-N-[2-(Acetylamino)ethyl]-2-((3S)-3-{[(6-chloro-2-naphthyl)sulfonyl]amino}-2-oxopyrrolidin-1-yl)-N-isopropylpropanamide
(2S)-2-((3S)-3-{[(6-Chloro-2-naphthyl)sulfonyl]amino}-2-oxopyrrolidin-1-yl)-N-isopropyl-N-(thien-2-ylmethyl)propanamide
(2S)-2-((3S)-3-{[(6-Chloro-2-naphthyl)sulfonyl]amino}-2-oxopyrrolidin-1-yl)-N-(3-hydroxypropyl)-N-isopropylpropanamide
(2S)-2-((3S)-3-{[(6-Chloro-2-naphthyl)sulfonyl]amino}-2-oxopyrrolidin-1-yl)-N-(2-hydroxyethyl)-N-isopropylpropanamide
(2S)-2-((3S)-3-{[(6-Chloro-2-naphthyl)sulfonyl]amino}-2-oxopyrrolidin-1-yl)-N-(2-cyanoethyl)-N-(cyclopropylmethyl)propanamide
(2S)-2-((3S)-3-{[(6-Chloro-2-naphthyl)sulfonyl]amino}-2-oxopyrrolidin-1-yl)-N-(2-cyanoethyl)-N-(2-pyridin-2-ylethyl)propanamide
(2S)-2-((3S)-3-{2-Amino-2-oxoethyl)[(6-chloro-2-naphthyl)sulfonyl]amino}-2-oxopyrrolidin-1-yl)-N-ethyl-N-(pyridin-4-ylmethyl)propanamide
(2S)-2-((3S)-3-{(2-Amino-2-oxoethyl)[(6-chloro-2-naphthyl)sulfonyl]amino}-2-oxopyrrolidin-1-yl)-N-isopropyl-N-(pyridin-2-ylmethyl)propanamide
(2S)-2-((3S)-3-{(2-Amino-2-oxoethyl)[(6-chloro-2-naphthyl)sulfonyl]amino}-2-oxopyrrolidin-1-yl)-N-methyl-N-(pyridin-4-ylmethyl)propanamide
(2S)-2-((3S)-3-{(2-Amino-2-oxoethyl)[(6-chloro-2-naphthyl)sulfonyl]amino}-2-oxopyrrolidin-1-yl)-N-methyl-N-(2-pyridin-2-ylethyl)propanamide
(2S)-2-((3S)-3-{(2-Amino-2-oxoethyl)[(6-chloro-2-naphthyl)sulfonyl]amino}-2-oxopyrrolidin-1-yl)-N,N-dimethylpropanamide
(2S)-2-((3S)-3-{(2-Amino-2-oxoethyl)[(6-chloro-2-naphthyl)sulfonyl]amino}-2-oxopyrrolidin-1-yl)-N-(2-hydroxyethyl)-N-isopropylpropanamide
(2S)-2-((3S)-3-{(2-Amino-2-oxoethyl)[(6-chloro-2-naphthyl)sulfonyl]amino}-2-oxopyrrolidin-1-yl)-N-ethyl-N-(3-hydroxypropyl)propanamide
(2S)-2-((3S)-3-{(2-Amino-2-oxoethyl)[(6-chloro-2-naphthyl)sulfonyl]amino}-2-oxopyrrolidin-1-yl)-N-ethyl-N-(2-morpholin-4-ylethyl)propanamide formate
(2S)-2-((3S)-3-{(2-Amino-2-oxoethyl)[(6-chloro-2-naphthyl)sulfonyl]amino}-2-oxopyrrolidin-1-yl)-N-[2-(dimethylamino)ethyl]-N-ethylpropanamide formate
(2S)-2-((3S)-3-{(2-Amino-2-oxoethyl)[(6-chloro-2-naphthyl)sulfonyl]amino}-2-oxopyrrolidin-1-yl)-N-ethyl-N-(2-hydroxyethyl)propanamide (2S)-2-((3S)-3-{(2-Amino-2-oxoethyl)[(6-chloro-2-naphthyl)sulfonyl]amino}-2-oxopyrrolidin-1-yl)-N-(2-methoxyethyl)-N-methylpropanamide (2S)-2-((3S)-3-{(2-Amino-2-oxoethyl)[(6-chloro-2-naphthyl)sulfonyl]amino}-2-oxopyrrolidin-1-yl)-N-ethyl-N-(2-piperidin-1-ylethyl)propanamide formate (2S)-2-((3S)-3-{(2-Amino-2-oxoethyl)[(6-chloronaphth-2-yl)sulfonyl]amino}-2-oxopyrrolidin-1-yl)-N-ethyl-N-methylpropanamide (2S)-2-((3S)-3-{(2-Amino-2-oxoethyl)[(6-chloronaphth-2-yl)sulfonyl]amino}-2-oxopyrrolidin-1-yl)-N,N-diethylpropanamide (2S)-2-((3S)-3-{(2-Amino-2-oxoethyl)[(6-chloronaphth-2-yl)sulfonyl]amino}-2-oxopyrrolidin-1-yl)-N,N-dipropylpropanamide (2S)-2-((3S)-3-{(2-Amino-2-oxoethyl)[(6-chloronaphth-2-yl)sulfonyl]amino}-2-oxopyrrolidin-1-yl)-N-ethyl-N-isopropylpropanamide (2S)-2-((3S)-3-{(2-Amino-2-oxoethyl)[(6-chloronaphth-2-yl)sulfonyl]amino}-2-oxopyrrolidin-1-yl)-N-isopropyl-N-(pyrid-4-ylmethyl)propanamide (2S)-2-((3S)-3-{(2-Amino-2-oxoethyl)[(6-chloronaphth-2-yl)sulfonyl]amino}-2-oxopyrrolidin-1-yl)-N-(2-cyanoethyl)-N-isopropylpropanamide (2S)-2-((3S)-3-{(2-Amino-2-oxoethyl)[(6-chloronaphth-2-yl)sulfonyl]amino}-2-oxopyrrolidin-1-yl)-N-(2-azepan-1-ylethyl)-N-isopropylpropanamide formate (2S)-N-[2Acetylamino)ethyl]-2-((3S)-3-{(2-amino-2-oxoethyl)[(6-chloronaphth-2-yl)sulfonyl]amino}-2-oxopyrrolidin-1-yl)-N-isopropylpropanamide (2S)-2-((3S)-3-{[(6-Chloro-2-naphthyl)sulfonyl]amino}-2-oxopyrrolidin-1-yl)-N-(2-cyanoethyl)-N-cyclopentylpropanamide (2S)-2-((3S)-3-{(2-Amino-2-oxoethyl)[(6-chloro-2-naphthyl)sulfonyl]amino}-2-oxopyrrolidin-1-yl)-N-(2-cyanoethyl)-N-cyclopentylpropanamide (2S)-2-((3S)-3-{(2-Amino-2-oxoethyl)[(6-chloro-2-naphthyl)sulfonyl]amino}-2-oxopyrrolidin-1-yl)-N-(2-cyanoethyl)-N-cyclopropylpropanamide (2S)-2-((3S)-3-{[(6-Chloro-2-naphthyl)sulfonyl]amino}-2-oxopyrrolidin-1-yl)-N-(2-cyanoethyl)-N-cyclobutylpropanamide (2S)-2-((3S)-3-(2-Amino-2-oxoethyl)[(6-chloro-2-naphthyl)sulfonyl]amino}-2-oxopyrrolidin-1-yl)-N-cyclopropyl-N-(pyridin-4-ylmethyl)propanamide (2S)-N-[2-(Aminosulfonyl)ethyl]-2-((3S)-3-{[(6-chloro-2-naphthyl)sulfonyl]amino}-2-oxopyrrolidin-1-yl)-N-isopropylpropanamide (2S)-2-((3S)-3-{(2-Amino-2-oxoethyl)[(6-chloro-2-naphthyl)sulfonyl]amino}-2-oxopyrrolidin-1-yl)-N-isopropyl-N-(2-piperidin-1-ylethyl)propanamide (2S)-2-((3S)-3-{(2-Amino-2-oxoethyl)[(6-chloro-2-naphthyl)sulfonyl]amino}-2-oxopyrrolidin-1-yl)-N-isopropyl-N-(2-morpholin-4-ylethyl)propanamide (2S)-2-((3S)-3-{[(6-Chloro-2-naphthyl)sulfonyl]amino}-2-oxopyrrolidin-1-yl)-N-isopropyl-N-(2-piperidin-1-ylethyl)propanamide (2S)-2-((3S)-3-{[(6-Chloro-2-naphthyl)sulfonyl]amino}-2-oxopyrrolidin-1-yl)-N-isopropyl-N-(2-morpholin-4-ylethyl)propanamide (2S)-2-((3S)-3-{[(6-Chloro-2-naphthyl)sulfonyl]amino}-2-oxopyrrolidin-1-yl)-N-isopropyl-N-(1H-pyrazol-3-ylmethyl)propanamide (2S)-2-((3S)-3-{[(6-Chloro-2-naphthyl)sulfonyl]amino}-2-oxopyrrolidin-1-yl)-N-isopropyl-N-[3-(4-methylpiperazin-1-yl)propyl]propanamide formate tert-Butyl 2-[[(2S)-2-((3S)-3-{(2-amino-2-oxoethyl)[(6-chloro-2-naphthyl)sulfonyl]amino}-2-oxopyrrolidin-1-yl)propanoyl](isopropyl)amino]ethylcarbamate tert-Butyl 3-[[(2S)-2-((3S)-3-{[(6-chloro-2-naphthyl)sulfonyl]amino}-2-oxopyrrolidin-1-yl)propanoyl](isopropyl)amino]propylcarbamate tert-Butyl 2-[[(2S)-2-((3S)-3-{[(6-chloro-2-naphthyl)sulfonyl]amino}-2-oxopyrrolidin-1-yl)propanoyl](cyclopropylmethyl)amino]ethylcarbamate (2S)-N-(2-Aminoethyl)-2-((3S)-3-{(2-amino-2-oxoethyl)[(6-chloro-2-naphthyl)sulfonyl]amino}-2-oxopyrrolidin-1-yl)-N-isopropylpropanamide hydrochloride (2S)-N-(3-Aminopropyl)-2-((3S)-3-{[(6-chloro-2-naphthyl)sulfonyl]amino}-2-oxopyrrolidin-1-yl)-N-isopropylpropanamide hydrochloride (2S)-N-(2-Aminoethyl)-2-((3S)-3-{[(6-chloro-2-naphthyl)sulfonyl]amino}-2-oxopyrrolidin-1-yl)-N-(cyclopropylmethyl)propanamide hydrochloride (2S)-N-(2-Aminoethyl)-2-((3S)-3-{[(6-chloro-2-naphthyl)sulfonyl]amino}-2-oxopyrrolidin-1-yl)-N-isopropylpropanamide (2S)-N-(2-Amino-2-oxoethyl)-2-((3S)-3-{[(6-chloro-2-naphthyl)sulfonyl]amino}-2-oxopyrrolidin-1-yl)-N-isopropylpropanamide (2S)-2-((3S)-3-{[(6-Chloro-2-naphthyl)sulfonyl]amino}-2-oxopyrrolidin-1-yl)-N-isopropyl-N-{2-[(methylsulfonyl)amino]ethyl}propanamide (2S)-2-((3S)-3-{(2-Amino-2-oxoethyl)[(6-chloro-2-naphthyl)sulfonyl]amino}-2-oxopyrrolidin-1-yl)-N-isopropyl-N-{2-[(methylsulfonyl)amino]ethyl}propanamide (2S)-2-((3S)-3-{[(6-Chloro-2-naphthyl)sulfonyl]amino}-2-oxopyrrolidin-1-yl)-N-isopropyl-N-{3-[(methylsulfonyl)amino]propyl}propanamide (2S)-2-((3S)-3-{[(6-Chloro-2-naphthyl)sulfonyl]amino}-2-oxopyrrolidin-1-yl)-N-(cyclopropylmethyl)-N-{2-[(methylsulfonyl)amino]ethyl}propanamide (2S)-N-[2-({(E)-Amino[oxido(oxo)hydrazono]methyl}amino)ethyl]-2-((3S)-3-{[(6-chloro-2-naphthyl)sulfonyl]amino}-2-oxopyrrolidin-1-yl)-N-isopropylpropanamide (2S)-N-[2-({(E)-Amino[oxido(oxo)hydrazono]methyl}amino)ethyl]-2-((3S)-3-{(2-amino-2-oxoethyl)[(6-chloro-2-naphthyl)sulfonyl]amino}-2-oxopyrrolidin-1-yl)-N-isopropylpropanamide (2S)-N-[3-({(E)-Amino[oxido(oxo)hydrazono]methyl}amino)propyl]-2-((3S)-3-{[(6-chloro-2-naphthyl)sulfonyl]amino}-2-oxopyrrolidin-1-yl)-N-isopropylpropanamide (2S)-2-((3S)-3-{[(6-Chloro-2-naphthyl)sulfonyl]amino}-2-oxopyrrolidin-1-yl)-N-isopropyl-N-[2-(methylamino)ethyl]propanamide (2S)-2-((3S)-3-{[(6-Chloro-2-naphthyl)sulfonyl]amino}-2-oxopyrrolidin-1-yl)-N-[2-(dimethylamino)ethyl]-N-isopropylpropanamide (2S)-N-{2-[(Aminocarbonyl)amino]ethyl}-2-((3S)-3-{[(6-chloro-2-naphthyl)sulfonyl]amino}-2-oxopyrrolidin-1-yl)-N-isopropylpropanamide (2S)-N-{2-[(Aminocarbonyl)amino]ethyl}-2-((3S)-3-{(2-amino-2-oxoethyl)[(6-chloro-2-naphthyl)sulfonyl]amino}-2-oxopyrrolidin-1-yl)-N-isopropylpropanamide (2S)-N-{2-[(Aminocarbonyl)amino]ethyl}-2-((3S)-3-{[(6-chloro-2-naphthyl)sulfonyl]amino}-2-oxopyrrolidin-1-yl)-N-(cyclopropylmethyl)propanamide (2S)-N-{3-[(Aminocarbonyl)amino]propyl}-2-((3S)-3-{[(6-chloro-2-naphthyl)sulfonyl]amino}-2-oxopyrrolidin-1-yl)-N-isopropylpropanamide (2S)-2-((3S)-3-{[(6-Chloro-2-naphthyl)sulfonyl]amino}-2-oxopyrrolidin-1-yl)-N-(cyclopropylmethyl)-N-(2-hydroxyethyl)propanamide (2S)-2-((3S)-3-{[(5'-Chloro-2,2'-bithien-5-yl)sulfonyl]amino}-2-oxopyrrolidin-1-yl)-N-ethyl-N-isopropylpropanamide (2S)-2-[(3S)-3-({[(E)-2-(4-Chlorophenyl)ethenyl]sulfonyl}amino)-2-oxopyrrolidin-1-yl]-N-ethyl-N-isopropylpropanamide (2S)-2-((3S)-{(2-Amino-2-oxoethyl)-3-({[(E)-2-(5-Chlorothien-2-yl)ethenyl]sulfonyl}amino)-2-oxopyrrolidin-1-yl)-N-ethyl-N-isopropylpropanamide (2S)-2-((3S)-{(2-Amino-2-oxoethyl)-3-({[(6-chloro-1-benzothien-2-yl)sulfonyl]amino)-2-oxopyrrolidin-1-yl)-N-ethyl-N-isopropylpropanamide.

In another aspect, preferred compounds of the invention include:

(2S)-2-((3S)-3-{[(6-Chloro-2-naphthyl)sulfonyl]amino}-2-oxopyrrolidin-1-yl)-N,N-diethylpropanamide;

(2S)-2-((3S)-3-{[(6-Chloro-2-naphthyl)sulfonyl]amino}-2-oxopyrrolidin-1-yl)-N-ethyl-N-(pyridin-4-ylmethyl)propanamide;

(2S)-2-((3S)-3-{[(6-Chloro-2-naphthyl)sulfonyl]amino}-2-oxopyrrolidin-1-yl)-N-ethyl-N-methylpropanamide;

(2S)-2-((3S)-3-{[(6-Chloro-2-naphthyl)sulfonyl]amino}-2-oxopyrrolidin-1-yl)-N-methyl-N-(2-phenylethyl)propanamide;

(2S)-2-((3S)-3-{[(6-Chloro-2-naphthyl)sulfonyl]amino}-2-oxopyrrolidin-1-yl)-N-ethyl-N-(2-phenylethyl)propanamide;

(2S)-2-((3S)-3-{[(6-Chloro-2-naphthyl)sulfonyl]amino}-2-oxopyrrolidin-1-yl)-N,N-dipropylpropanamide;

(2S)-2-((3S)-3-{[(6-Chloro-2-naphthyl)sulfonyl]amino}-2-oxopyrrolidin-1-yl)-N-ethyl-N-isopropylpropanamide;

(2S)-2-((3S)-3-{[(6-chloro-2-naphthyl)sulfonyl]amino}-2-oxopyrrolidin-1-yl)-N-methyl-N-(2-pyridin-2-ylethyl)propanamide;

(2S)-2-((3S)-3-{[(6-Chloro-2-naphthyl)sulfonyl]amino}-2-oxopyrrolidin-1-yl)-N-methyl-N-(pyridin-3-ylmethyl)propanamide;

(2S)-2-((3S)-3-{[(6-chloro-2-naphthyl)sulfonyl]amino}-2-oxopyrrolidin-1-yl)-N-isopropyl-N-(pyridin-4-ylmethyl)propanamide;

(2S)-2-((3S)-3-{[(6-Chloro-2-naphthyl)sulfonyl]amino}-2-oxopyrrolidin-1-yl)-N-isobutyl-N-(pyridin-2-ylmethyl)propanamide;

(2S)-2-((3S)-3-{[(6-chloro-2-naphthyl)sulfonyl]amino}-2-oxopyrrolidin-1-yl)-N-propyl-N-(pyridin-2-ylmethyl)propanamide;

(2S)-2-((3S)-3-{[(6-Chloro-2-naphthyl)sulfonyl]amino}-2-oxopyrrolidin-1-yl)-N-isopropyl-N-(pyridin-3-ylmethyl)propanamide;

(2S)-N-(2-Azepan-1-ylethyl)-2-((3S)-3-{[(6-chloro-2-naphthyl)sulfonyl]amino}-2-oxopyrrolidin-1-yl)-N-isopropylpropanamide formate;

(2S)-2-((3S)-3-{[(6-Chloro-2-naphthyl)sulfonyl]amino}-2-oxopyrrolidin-1-yl)-N-(2-cyanoethyl)-N-isopropylpropanamide;

(2S)-2-((3S)-3-{[(6-Chloro-2-naphthyl)sulfonyl]amino}-2-oxopyrrolidin-1-yl)propanoyl)-N-isopropyl-beta-alaninamide;

(2S)-2-((3S)-3-{[(6-Chloro-2-naphthyl)sulfonyl]amino}-2-oxopyrrolidin-1-yl)-N-(2-hydroxyethyl)-N-isopropylpropanamide;

(2S)-2-((3S)-3-{[(6-Chloro-2-naphthyl)sulfonyl]amino}-2-oxopyrrolidin-1-yl)-N-(2-cyanoethyl)-N-(cyclopropylmethyl)propanamide;

(2S)-2-((3S)-3-{[(6-Chloro-2-naphthyl)sulfonyl]amino}-2-oxopyrrolidin-1-yl)-N-(2-cyanoethyl)-N-isobutylpropanamide;

(2S)-2-((3S)-3-{[(6-Chloro-2-naphthyl)sulfonyl]amino}-2-oxopyrrolidin-1-yl)-N,N-dimethylpropanamide;

(2S)-2-((3S)-3-{[(6-Chloro-2-naphthyl)sulfonyl]amino}-2-oxopyrrolidin-1-yl)-N-isopropyl-N-methylpropanamide;

(2S)-2-((3S)-3-{[(6-Chloro-2-naphthyl)sulfonyl]amino}-2-oxopyrrolidin-1-yl)-N-(2-hydroxyethyl)-N-methylpropanamide;

(2S)-2-((3S)-3-{[(6-Chloro-2-naphthyl)sulfonyl]amino}-2-oxopyrrolidin-1-yl)-N-(2-cyanoethyl)-N-methylpropanamide;

(2S)-N-(2-Amino-2-oxoethyl)-2-((3S)-3-{[(6-chloro-2-naphthyl)sulfonyl]amino}-2-oxopyrrolidin-1-yl)-N-methylpropanamide;

(2S)-2-((3S)-3-{[(6-Chloro-2-naphthyl)sulfonyl]amino}-2-oxopyrrolidin-1-yl)-N-[2-(dimethylamino)-2-oxoethyl]-N-methylpropanamide;

(2S)-2-((3S)-3-{[(6-Chloro-2-naphthyl)sulfonyl]amino}-2-oxopyrrolidin-1-yl)-N-ethyl-N-(3-hydroxypropyl)propanamide;

(2S)-2-((3S)-3-{[(6-Chloro-2-naphthyl)sulfonyl]amino}-2-oxopyrrolidin-1-yl)-N-methyl-N-(2-pyrrolidin-1-ylethyl)propanamide formate;

(2S)-2-((3S)-3-{[(6-Chloro-2-naphthyl)sulfonyl]amino}-2-oxopyrrolidin-1-yl)-N-methyl-N-(2-morpholin-4-ylethyl)propanamide formate;

(2S)-2-((3S)-3-{[(6-Chloro-2-naphthyl)sulfonyl]amino}-2-oxopyrrolidin-1-yl)-N-ethyl-N-(2-morpholin-4-ylethyl)propanamide formate;

(2S)-2-((3S)-3-{[(6-Chloro-2-naphthyl)sulfonyl]amino}-2-oxopyrrolidin-1-yl)-N-[2-(dimethylamino)ethyl]-N-ethylpropanamide formate;

(2S)-2-((3S)-3-{[(6-Chloro-2-naphthyl)sulfonyl]amino}-2-oxopyrrolidin-1-yl)-N-isopropyl-N-(pyridin-2-ylmethyl)propanamide;

(2S)-2-((3S)-3-{[(6-Chloro-2-naphthyl)sulfonyl]amino}-2-oxopyrrolidin-1-yl)-N-ethyl-N-(2-pyridin-2-ylethyl)propanamide;

(2S)-2-((3S)-3-{[(6-Chloro-2-naphthyl)sulfonyl]amino}-2-oxopyrrolidin-1-yl)-N-methyl-N-(pyridin-2-ylmethyl)propanamide;

(2S)-2-((3S)-3-{[(6-Chloro-2-naphthyl)sulfonyl]amino}-2-oxopyrrolidin-1-yl)-N-methyl-N-(2-pyridin-4-ylethyl)propanamide;

(2S)-2-((3S)-3-{[(6-Chloro-2-naphthyl)sulfonyl]amino}-2-oxopyrrolidin-1-yl)-N-methyl-N-(pyridin-4-ylmethyl)propanamide;

(2S)-2-((3S)-3-{[(6-Chloro-2-naphthyl)sulfonyl]amino}-2-oxopyrrolidin-1-yl)-N-[2-(1H-imidazol-4-yl)ethyl]-N-methylpropanamide formate;

(2S)-2-((3S)-3-{[(6-Chloro-2-naphthyl)sulfonyl]amino}-2-oxopyrrolidin-1-yl)-N-(2-cyanoethyl)-N-(pyridin-3-ylmethyl)propanamide;

(2S)-2-((3S)-3-{[(6-Chloro-2-naphthyl)sulfonyl]amino}-2-oxopyrrolidin-1-yl)-N-ethyl-N-(2-hydroxyethyl)propanamide;

(2S)-2-((3S)-3-{[(6-Chloro-2-naphthyl)sulfonyl]amino}-2-oxopyrrolidin-1-yl)-N-(2-methoxyethyl)-N-methylpropanamide;

(2S)-2-((3S)-3-{[(6-Chloro-2-naphthyl)sulfonyl]amino}-2-oxopyrrolidin-1-yl)-N-ethyl-N-(2-piperidin-1-ylethyl)propanamide formate;

(2S)-2-((3S)-3-{[(6-Chloro-2-naphthyl)sulfonyl]amino}-2-oxopyrrolidin-1-yl)-N-isopropyl-N-(2-pyridin-2-ylethyl)propanamide;

(2S)-2-((3S)-3-{[(6-Chloro-2-naphthyl)sulfonyl]amino}-2-oxopyrrolidin-1-yl)-N-(2-hydroxypropyl)-N-isopropylpropanamide;
(2S)-2-((3S)-3-{[(6-Chloro-2-naphthyl)sulfonyl]amino}-2-oxopyrrolidin-1-yl)-N-(cyanomethyl)-N-isopropylpropanamide formate;
(2S)-2-((3S)-3-{[(6-Chloro-2-naphthyl)sulfonyl]amino}-2-oxopyrrolidin-1-yl)-N-isopropyl-N-(3-methoxypropyl)propanamide;
(2S)-2-((3S)-3-{[(6-Chloro-2-naphthyl)sulfonyl]amino}-2-oxopyrrolidin-1-yl)-N-isopropyl-N-(2-methoxyethyl)propanamide;
(2S)-N-[2-(Acetylamino)ethyl]-2-((3S)-3-{[(6-chloro-2-naphthyl)sulfonyl]amino}-2-oxopyrrolidin-1-yl)-N-isopropylpropanamide;
(2S)-N-Benzyl-2-((3S)-3-{[(6-chloro-2-naphthyl)sulfonyl]amino}-2-oxopyrrolidin-1-yl)-N-isopropylpropanamide;
(2S)-2-((3S)-3-{[(6-Chloro-2-naphthyl)sulfonyl]amino}-2-oxopyrrolidin-1-yl)-N-isopropyl-N-(thien-2-ylmethyl)propanamide;
(2S)-2-((3S)-3-{[(6-Chloro-2-naphthyl)sulfonyl]amino}-2-oxopyrrolidin-1-yl)-N-(3-hydroxypropyl)-N-isopropylpropanamide;
(2S)-2-((3S)-3-{[(6-Chloro-2-naphthyl)sulfonyl]amino}-2-oxopyrrolidin-1-yl)-N-(2-hydroxyethyl)-N-isopropylpropanamide;
(2S)-2-((3S)-3-{[(6-Chloro-2-naphthyl)sulfonyl]amino}-2-oxopyrrolidin-1-yl)-N-(3-hydroxypropyl)-N-(pyridin-4-ylmethyl)propanamide;
(2S)-2-((3S)-3-{[(6-Chloro-2-naphthyl)sulfonyl]amino}-2-oxopyrrolidin-1-yl)-N-(3-hydroxypropyl)-N-(pyridin-3-ylmethyl)propanamide;
(2S)-2-((3S)-3-{[(6-Chloro-2-naphthyl)sulfonyl]amino}-2-oxopyrrolidin-1-yl)-N-(3-hydroxypropyl)-N-(pyridin-2-ylmethyl)propanamide;
(2S)-2-((3S)-3-{[(6-Chloro-2-naphthyl)sulfonyl]amino}-2-oxopyrrolidin-1-yl)-N-(2-cyanoethyl)-N-(tetrahydrofuran-2-ylmethyl)propanamide;
(2S)-2-((3S)-3-{[(6-Chloro-2-naphthyl)sulfonyl]amino}-2-oxopyrrolidin-1-yl)-N-(2-cyanoethyl)-N-(cyclopropylmethyl)propanamide;
(2S)-2-((3S)-3-{[(6-Chloro-2-naphthyl)sulfonyl]amino}-2-oxopyrrolidin-1-yl)-N-(2-cyanoethyl)-N-(2-pyridin-2-ylethyl)propanamide;
(2S)-2-((3S)-3-{[(6-Chloro-2-naphthyl)sulfonyl]amino}-2-oxopyrrolidin-1-yl)-N-(2-cyanoethyl)-N-isobutylpropanamide;
(2S)-2-((3S)-3-{(2-Amino-2-oxoethyl)[(6-chloro-2-naphthyl)sulfonyl]amino}-2-oxopyrrolidin-1-yl)-N-ethyl-N-(pyridin-4-ylmethyl)propanamide;
(2S)-2-((3S)-3-{(2-Amino-2-oxoethyl)[(6-chloro-2-naphthyl)sulfonyl]amino}-2-oxopyrrolidin-1-yl)-N-ethyl-N-(2-pyridin-2-ylethyl)propanamide;
(2S)-2-((3S)-3-{(2-amino-2-oxoethyl)[(6-chloro-2-naphthyl)sulfonyl]amino}-2-oxopyrrolidin-1-yl)-N-ethyl-N-(2-hydroxyethyl)propanamide;
(2S)-2-((3S)-3-{(2-Amino-2-oxoethyl)[(6-chloro-2-naphthyl)sulfonyl]amino}-2-oxopyrrolidin-1-yl)-N-isopropyl-N-(pyridin-2-ylmethyl)propanamide;
(2S)-2-((3S)-3-{(2-Amino-2-oxoethyl)[(6-chloro-2-naphthyl)sulfonyl]amino}-2-oxopyrrolidin-1-yl)-N-methyl-N-(pyridin-2-ylmethyl)propanamide;
(2S)-2-((3S)-3-{(2-Amino-2-oxoethyl)[(6-chloro-2-naphthyl)sulfonyl]amino}-2-oxopyrrolidin-1-yl)-N-methyl-N-(pyridin-3-ylmethyl)propanamide;
(2S)-2-((3S)-3-{(2-Amino-2-oxoethyl)[(6-chloro-2-naphthyl)sulfonyl]amino}-2-oxopyrrolidin-1-yl)-N-methyl-N-(2-pyridin-4-ylethyl)propanamide;
(2S)-2-((3S)-3-{(2-Amino-2-oxoethyl)[(6-chloro-2-naphthyl)sulfonyl]amino}-2-oxopyrrolidin-1-yl)-N-methyl-N-(pyridin-4-ylmethyl)propanamide;
(2S)-2-((3S)-3-{(2-Amino-2-oxoethyl)[(6-chloro-2-naphthyl)sulfonyl]amino}-2-oxopyrrolidin-1-yl)-N-[2-(1H-imidazol-4-yl)ethyl]-N-methylpropanamide formate;
(2S)-2-((3S)-3-{(2-Amino-2-oxoethyl)[(6-chloro-2-naphthyl)sulfonyl]amino}-2-oxopyrrolidin-1-yl)-N-methyl-N-(2-pyridin-2-ylethyl)propanamide;
(2S)-2-((3S)-3-{(2-Amino-2-oxoethyl)[(6-chloro-2-naphthyl)sulfonyl]amino}-2-oxopyrrolidin-1-yl)-N-methyl-N-(2-phenylethyl)propanamide;
(2S)-2-((3S)-3-{(2-Amino-2-oxoethyl)[(6-chloro-2-naphthyl)sulfonyl]amino}-2-oxopyrrolidin-1-yl)-N-ethyl-N-(2-phenylethyl)propanamide;
(2S)-2-((3S)-3-{(2-Amino-2-oxoethyl)[(6-chloro-2-naphthyl)sulfonyl]amino}-2-oxopyrrolidin-1-yl)-N,N-dimethylpropanamide;
(2S)-2-((3S)-3-{(2-Amino-2-oxoethyl)[(6-chloro-2-naphthyl)sulfonyl]amino}-2-oxopyrrolidin-1-yl)-N-isopropyl-N-methylpropanamide;
(2S)-2-((3S)-3-{(2-Amino-2-oxoethyl)[(6-chloro-2-naphthyl)sulfonyl]amino}-2-oxopyrrolidin-1-yl)-N-(2-hydroxyethyl)-N-methylpropanamide;
(2S)-2-((3S)-3-{(2-Amino-2-oxoethyl)[(6-chloro-2-naphthyl)sulfonyl]amino}-2-oxopyrrolidin-1-yl)-N-(2-hydroxyethyl)-N-isopropylpropanamide;
(2S)-2-((3S)-3-{(2-Amino-2-oxoethyl)[(6-chloro-2-naphthyl)sulfonyl]amino}-2-oxopyrrolidin-1-yl)-N-(2cyanoethyl)-N-methylpropanamide;
(2S)-N-(2-Amino-2-oxoethyl)-2-((3S)-3-{(2-amino-2-oxoethyl)[(6-chloro-2-naphthyl)sulfonyl]amino}-2-oxopyrrolidin-1-yl)-N-methylpropanamide;
(2S)-2-((3S)-3-{(2-Amino-2-oxoethyl)[(6-chloro-2-naphthyl)sulfonyl]amino}-2-oxopyrrolidin-1-yl)-N-[2-(dimethylamino)-2-oxoethyl]-N-methylpropanamide;
(2S)-2-((3S)-3-{(2-Amino-2-oxoethyl)[(6-chloro-2-naphthyl)sulfonyl]amino}-2-oxopyrrolidin-1-yl)-N-ethyl-N-(3-hydroxypropyl)propanamide;
(2S)-2-((3S)-3-{(2-Amino-2-oxoethyl)[(6-chloro-2-naphthyl)sulfonyl]amino}-2-oxopyrrolidin-1-yl)-N-methyl-N-(2-pyrrolidin-1-ylethyl)propanamide formate;
(2S)-2-((3S)-3-{(2-Amino-2-oxoethyl)[(6-chloro-2-naphthyl)sulfonyl]amino}-2-oxopyrrolidin-1-yl)-N-methyl-N-(2-morpholin-4-ylethyl)propanamide formate;
(2S)-2-((3S)-3-{(2-Amino-2-oxoethyl)[(6-chloro-2-naphthyl)sulfonyl]amino}-2-oxopyrrolidin-1-yl)-N-ethyl-N-(2-morpholin-4-ylethyl)propanamide formate;
(2S)-2-((3S)-3-{(2-Amino-2-oxoethyl)[(6-chloro-2-naphthyl)sulfonyl]amino}-2-oxopyrrolidin-1-yl)-N-[2dimethylamino)ethyl]-N-ethylpropanamide formate;
(2S)-2-((3S)-3-{(2-Amino-2-oxoethyl)[(6-chloro-2-naphthyl)sulfonyl]amino}-2-oxopyrrolidin-1-yl)-N-(2-cyanoethyl)-N-(pyridin-3-ylmethyl)propanamide;
(2S)-2-((3S)-3-{(2-Amino-2-oxoethyl)[(6-chloro-2-naphthyl)sulfonyl]amino}-2-oxopyrrolidin-1-yl)-N-ethyl-N-(2-bydroxyethyl)propanamide;
(2S)-2-((3S)-3-{(2-Amino-2-oxoethyl)[(6-chloro-2-naphthyl)sulfonyl]amino}-2-oxopyrrolidin-1-yl)-N-(2-methoxyethyl)-N-methylpropanamide;
(2S)-2-((3S)-3-{(2-Amino-2-oxoethyl)[(6-chloro-2-naphthyl)sulfonyl]amino}-2-oxopyrrolidin-1-yl)-N-ethyl-N-(2-piperidin-1-ylethyl)propanamide formate;

(2S)-2-((3S)-3-{(2-Amino-2-oxoethyl)[(6-chloro-2-naphthyl)sulfonyl]amino}-2-oxopyrrolidin-1-yl)-N-(2-hydroxyethyl)-N-(2-morpholin-4-ylethyl)propanamide formate;

(2S)-2-((3S)-3-{(2-Amino-2-oxoethyl)[(6-chloronaphth-2-yl)sulfonyl]amino}-2-oxopyrrolidin-1-yl)-N-ethyl-N-methylpropanamide;

(2S)-2-((3S)-3-{(2-Amino-2-oxoethyl)[(6-chloronaphth-2-yl)sulfonyl]amino}-2-oxopyrrolidin-1-yl)-N,N-diethylpropanamide;

(2S)-2-((3S)-3-{(2-Amino-2-oxoethyl)[(6-chloronaphth-2-yl)sulfonyl]amino}-2-oxopyrrolidin-1-yl)-N,N-dipropylpropanamide;

(2S)-2-((3S)-3-{(2-Amino-2-oxoethyl)[(6-chloronaphth-2-yl)sulfonyl]amino}-2-oxopyrrolidin-1-yl)-N-ethyl-N-isopropylpropanamide;

(2S)-2-((3S)-3-{(2-Amino-2-oxoethyl)[(6-chloronaphth-2-yl)sulfonyl]amino}-2-oxopyrrolidin-1-yl)-N-isopropyl-N-(pyrid-4-ylmethyl)propanamide;

(2S)-2-((3S)-3-{(2-Amino-2-oxoethyl)[(6-chloronaphth-2-yl)sulfonyl]amino}-2-oxopyrrolidin-1-yl)-N-(2-cyanoethyl)-N-isopropylpropanamide;

(2S)-2-((3S)-3-{(2-Amino-2-oxoethyl)[(6-chloronaphth-2-yl)sulfonyl]amino}-2-oxopyrrolidin-1-yl)-N-(2-azepan-1-ylethyl)-N-isopropylpropanamide formate;

(2S)-N-[2-(Acetylamino)ethyl]-2-((3S)-3-{(2-amino-2-oxoethyl)[(6-chloronaphth-2-yl)sulfonyl]amino}-2-oxopyrrolidin-1-yl)-N-isopropylpropanamide;

(2S)-2-((3S)-3-{[(6-Chloro-2-naphthyl)sulfonyl]amino}-2-oxopyrrolidin-1-yl)-N-cyclopentyl-N-methylpropanamide;

(2S)-2-((3S)-3-{[(6-Chloro-2-naphthyl)sulfonyl]amino}-2-oxopyrrolidin-1-yl)-N-cyclohexyl-N-ethylpropanamide;

(2S)-2-((3S)-3-{[(6-Chloro-2-naphthyl)sulfonyl]amino}-2-oxopyrrolidin-1-yl)-N-cyclohexyl-N-methylpropanamide;

(2S)-2-((3S)-3-{[(6-Chloro-2-naphthyl)sulfonyl]amino}-2-oxopyrrolidin-1-yl)-N-(2-cyanoethyl)-N-cyclopentylpropanamide;

(2S)-2-((3S)-3-{[(6-Chloro-2-naphthyl)sulfonyl]amino}-2-oxopyrrolidin-1-yl)-N-(2-cyanoethyl)-N-cyclopropylpropanamide;

(2S)-2-((3S)-3-{(2-Amino-2-oxoethyl)[(6-chloro-2-naphthyl)sulfonyl]amino}-2-oxopyrrolidin-1-yl)-N-methyl-N-(1-methylpiperidin-4-yl)propanamide formate;

(2S)-2-((3S)-3-{[(6-Chloro-2-naphthyl)sulfonyl]amino}-2-oxopyrrolidin-1-yl)-N-ethyl-N-phenylpropanamide;

(2S)-2-((3S)-3-{(2-Amino-2-oxoethyl)[(6-chloro-2-naphthyl)sulfonyl]amino}-2-oxopyrrolidin-1-yl)-N-(2-cyanoethyl)-N-cyclopentylpropanamide;

(2S)-2-((3S)-3-{[(6-Chloro-2-naphthyl)sulfonyl]amino}-2-oxopyrrolidin-1-yl)-N-(2-cyanoethyl)-N-cyclohexylpropanamide;

(2S)-2-((3S)-3-{(2-Amino-2-oxoethyl)[(6-chloro-2-naphthyl)sulfonyl]amino}-2-oxopyrrolidin-1-yl)-N-cyclohexyl-N-methylpropanamide;

(2S)-2-((3S)-3-{(2-Amino-2-oxoethyl)[(6-chloro-2-naphthyl)sulfonyl]amino}-2-oxopyrrolidin-1-yl)-N-(2-cyanoethyl)-N-cyclopropylpropanamide;

(2S)-2-((3S)-3-{[(6-Chloro-2-naphthyl)sulfonyl]amino}-2-oxopyrrolidin-1-yl)-N-(2-cyanoethyl)-N-cyclobutylpropanamide;

(2S)-2-((3S)-3-{[(6-Chloro-2-naphthyl)sulfonyl]amino}-2-oxopyrrolidin-1-yl)-N-cyclopropyl-N-(pyridin-4-ylmethyl)propanamide;

(2S)-2-((3S)-3-(2-Amino-2-oxoethyl)[(6-chloro-2-naphthyl)sulfonyl]amino}-2-oxopyrrolidin-1-yl)-N-cyclopropyl-N-(pyridin-4-ylmethyl)propanamide;

(2S)-N-(2-Aminoethyl)-2-((3S)-3-{[(6-chloro-2-naphthyl)sulfonyl]amino}-2-oxopyrrolidin-1-yl)-N-isopropylpropanamide;

(2S)-2-((3S)-3-{[(6-Chloro-2-naphthyl)sulfonyl]amino}-2-oxopyrrolidin-1-yl)-N-isopropyl-N-{2-[(methylsulfonyl)amino]ethyl}propanamide;

(2S)-N-{2-[(Aminocarbonyl)amino]ethyl}-2-((3S)-3-{[(6-chloro-2-naphthyl)sulfonyl]amino}-2-oxopyrrolidin-1-yl)-N-isopropylpropanamide The compounds of formula (I) are Factor Xa inhibitors and as such are useful in the treatment of clinical conditions susceptible to amelioration by administration of a Factor Xa inhibitor. Such conditions include acute vascular diseases such as coronary thrombosis (for example myocardial infarction and unstable angina), thromboembolism, acute vessel closure associated with thrombolytic therapy and percutaneous transluminal coronary angioplasty (PTCA), transient ischemic attacks, pulmonary embolism, deep vein thrombosis, peripheral arterial occlusion, prevention of vessel luminal narrowing (restenosis), and the prevention of thromboembolic events associated with atrial fibrillation, e.g. stroke; in oedema and PAF mediated inflammatory diseases such as adult respiratory shock syndrome, septic shock and reperfusion damage; the treatment of pulmonary fibrosis; the treatment of tumour metastasis; neurogenerative disease such as Parkinson's and Alzheimer's diseases; viral infection; Kasabach Merritt Syndrome; Haemolytic uremic syndrome; arthritis; osteoporosis; as anti-coagulants for extracorporeal blood in for example, dialysis, blood filtration, bypass, and blood product storage; and in the coating of invasive devices such as prostheses, artificial valves and catheters in reducing the risk of thrombus formation.

Accordingly, one aspect of present invention provides a compound of formula (I) or a physiologically acceptable derivative thereof for use in medical therapy, particularly for use in the amelioration of a clinical condition in a mammal, including a human, for which a Factor Xa inhibitor is indicated.

In another aspect, the invention provides a method for the treatment and/or prophylaxis of a mammal, including a human, suffering from a condition susceptible to amelioration by a Factor Xa inhibitor which method comprises administering to the subject an effective amount of a compound of formula (I) or a pharmaceutically acceptable derivative thereof.

In another aspect, the present invention provides the use of a compound of formula (I) or a pharmaceutically acceptable derivative thereof, for the manufacture of a medicament for the treatment and/or prophylaxis of a condition susceptible to amelioration by a Factor Xa inhibitor.

Preferably, the condition susceptible to amelioration by a Factor Xa inhibitor is selected from coronary thrombosis (for example myocardial infarction and unstable angina), pulmonary embolism, deep vein thrombosis and the prevention of thromboembolic events associated with atrial fibrillation, e.g. stroke;

It will be appreciated that reference to treatment includes acute treatment or prophylaxis as well as the alleviation of established symptoms.

While it is possible that, for use in therapy, a compound of the present invention may be administered as the raw chemical, it is preferable to present the active ingredient as a pharmaceutical formulation.

In a further aspect, the invention provides a pharmaceutical composition comprising at least one compound of formula (I) or a pharmaceutically acceptable derivative thereof in association with a pharmaceutically acceptable carrier and/or excipient. The carrier and/or excipient must be "acceptable" in the sense of being compatible with the other ingredients of the formulation and not deleterious to the receipient thereof.

Accordingly, the present invention further provides a pharmaceutical formulation comprising at least one compound of formula (I) or a pharmaceutically acceptable derivative thereof, thereof in association with a pharmaceutically acceptable carrier and/or excipient. The carrier and/or excipient must be "acceptable" in the sense of being compatible with the other ingredients of the formulation and not deleterious to the receipient thereof.

In another aspect, the invention provides a pharmaceutical composition comprising, as active ingredient, at least one compound of formula (I) or a pharmaceutically acceptable derivative thereof in association with a pharmaceutically acceptable carrier and/or excipient for use in therapy, and in particular in the treatment of human or animal subjects suffering from a condition susceptible to amelioration by a Factor Xa inhibitor.

There is further provided by the present invention a process of preparing a pharmaceutical composition, which process comprises mixing at least one compound of formula (I) or a pharmaceutically acceptable derivative thereof, together with a pharmaceutically acceptable carrier and/or excipient.

The compounds for use according to the present invention may be formulated for oral, buccal, parenteral, topical, rectal or transdermal administration or in a form suitable for administration by inhalation or insufflation (either through the mouth or the nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions or they may be presented as a dry product for constitution with water or other suitable vehicles before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in a conventional manner.

The compounds according to the present invention may be formulated for parenteral administration by injection, e.g. by bolus injection or continuous infusion. Formulations for injection may be presented in unit dosage form, e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds according to the present invention may be formulated for topical administration by insufflation and inhalation. Examples of types of preparation for topical administration include sprays and aerosols for use in an inhaler or insufflator.

Powders for external application may be formed with the aid of any suitable powder base, for example, lactose, talc or starch. Spray compositions may be formulated as aqueous solutions or suspensions or as aerosols delivered from pressurised packs, such as metered dose inhalers, with the use of a suitable propellant.

The compounds according to the present invention may also be formulated in rectal compositions such as suppositories or retention enemas, e.g. containing conventional suppository bases such as cocoa butter or other glycerides.

In addition to the formulations described previously, the compounds may also be formulated as a depot preparation. Such long acting formulations may be administered by implantation (for example subcutaneously, transcutaneously or intramuscularly) or by intramuscular injection. Thus, for example, the compounds according to the present invention may be formulated with suitable polymeric or hydrophobic materials (for example as an emulsion in an acceptable oil) or ion exchange resins or as sparingly soluble derivatives, for example, as a sparingly soluble salt.

A proposed dose of the compounds according to the present invention for administration to a human (of approximately 70 kg body weight) is 0.1 mg to 1 g, preferably to 1 mg to 500 mg of the active ingredient per unit dose, expressed as the weight of free base. The unit dose may be administered, for example, 1 to 4 times per day. The dose will depend on the route of administration. It will be appreciated that it may be necessary to make routine variations to the dosage depending on the age and weight of the patient as well as the severity of the condition to be treated. The dosage will also depend on the route of administration. The precise dose and route of administration will ultimately be at the discretion of the attendant physician or veterinarian.

The compounds of formula (I) may also be used in combination with other therapeutic agents. The invention thus provides, in a further aspect, a combination comprising a compound of formula (I) or a pharmaceutically acceptable derivative thereof together with a further therapeutic agent.

When a compound of formula (I) or a pharmaceutically acceptable derivative thereof is used in combination with a second therapeutic agent active against the same disease state the dose of each compound may differ from that when the compound is used alone. The compounds of the present invention may be used in combination with other antithrombotic drugs such as thrombin inhibitors, thromboxane receptor antagonists, prostacyclin mimetics, phosphodiesterase inhibitors, fibrinogen antagonists, thrombolytic drugs such as tissue plaminogen activator and streptokinase, non-steroidal anti-inflammatory drugs such as aspirin, and the like.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations by any convenient route.

When administration is sequential, either the Factor Xa inhibitor or the second therapeutic agent may be administered first. When administration is simultaneous, the combination may be administered either in the same or different pharmaceutical composition.

When combined in the same formulation it will be appreciated that the two compounds must be stable and compatible with each other and the other components of the formulation. When formulated separately they may be provided in any convenient formulation, conveniently in such manner as are known for such compounds in the art.

When a compound of formula (I) or a pharmaceutically acceptable derivative thereof is used in combination with a second therapeutic agent active against the same disease state the dose of each compound may differ from that when the compound is used alone. Appropriate doses will be readily appreciated by those skilled in the art. It will be appreciated that the amount of a compound of the invention required for use in treatment will vary with the nature of the condition being treated and the age and the condition of the patient and will be ultimately at the discretion of the attendant physician or veterinarian.

The compounds of formula (I) and pharmaceutically acceptable derivative thereof may be prepared by the processes described hereinafter, said processes constituting a further aspect of the invention. In the following description, the groups are as defined above for compounds of formula (I) unless otherwise stated.

According to a further aspect of the present invention, there is provided a process (A) for preparing a compound of formula (I) which process comprises reacting a compound of formula (II) with a compound of formula (III).

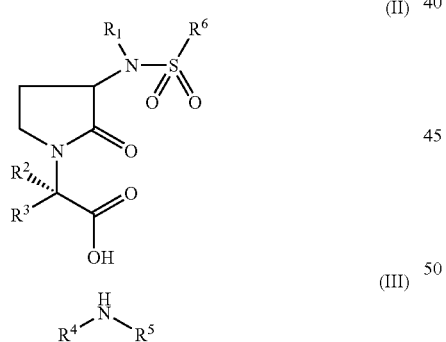

(II)

(III)

Suitably, the reaction may be carried out in the presence of a coupling agent, for example 1-[3-(dimethylamino)propyl]-3-ethyl carbodimide hydrochloride, HOBt (1-hydroxybenzotriazole), a base, e.g. $Et_3N$ (triethylamine), and an organic solvent, e.g. DCM (dichloromethane), suitably at room temperature.

It will be appreciated by persons skilled in the art that compounds of formula (I) may be prepared by interconversion, utilising other compounds of formula (I) which are optionally protected by standard protecting groups, as precursors. For instance, compounds of formula (I) where $R^5$ is $C_{1-3}alkylNH_2$, may be converted into compounds of formula (I) possessing alternative substituents at $R^5$, e.g. —$C_{2-4}alkylNR^aR^b$, —$C_{2-4}alkylNHCOC_{1-3}alkyl$, $C_{2-4}alkylNHCONR^aR^b$, $C_{2-4}alkylNHSO_2R^e$, by methods well known in the art (see for example March, J., Advanced Organic Chemistry, 4$^{th}$ Edition 1992, John Wiley & Sons).

Compounds of formula (II) may be prepared from compounds of formula (IV):

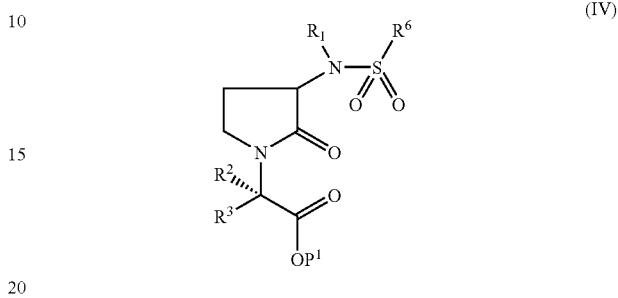

(IV)

wherein $P^1$ is a suitable carboxylic acid protecting group, e.g. t-Butyl, by removal of the protecting group under standard conditions. For example, when $P^1$ represents t-Butyl, removal of the protecting group may be effected under acidic conditions, using for example TFA (trifluoroacetic acid) in a solvent such as DCM.

A compound of formula (IV) may be prepared by reacting a compound of formula (V) with a compound of formula (VI) where $P^1$ is as described above:

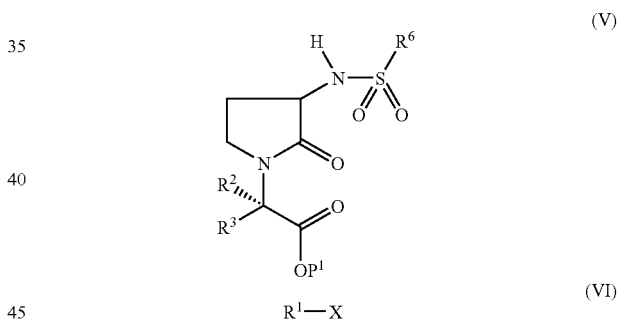

(V)

$R^1$—X (VI)

Suitably, where X is a leaving group such as a halogen atom, e.g. bromine, the reaction is carried out in the presence of a base, e.g. potassium carbonate. Preferably, the reaction is effected in a suitable solvent, e.g. DMF, suitably at room temperature.

A compound of formula (V) may be prepared by reacting a compound of formula (VII) with a compound of formula (VIII):

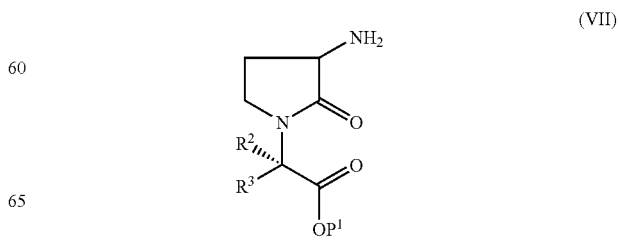

(VII)

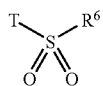

(VIII)

wherein T is a reactive group, such as a halide, preferably chloride, and $P^1$ is as described above. The reaction is conveniently carried out in the presence of a base, e.g. pyridine, and in a suitable solvent, e.g. DCM, suitably at room temperature.

A compound of formula (VII) may be prepared from a compound of formula (IX)

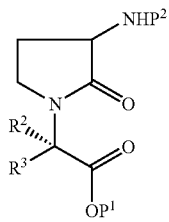

(IX)

where $P^1$ is as described above and $P^2$ represents a suitable amine protecting group, e.g. Cbz (benzyloxycarbonyl), by removal of the protecting group under standard conditions. For example, the protecting group may be removed by reaction with hydrogen in the presence of a metal catalyst, e.g. palladium/C. Suitably, the reaction is carried out in an alcoholic solvent, e.g. ethanol, suitably at room temperature.

A compound of formula (D) may be prepared from a compound of formula (X)

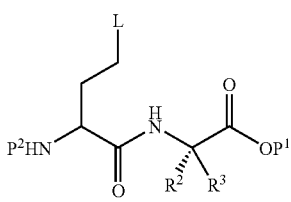

(X)

by cyclisation, wherein $P^1$ and $P^2$ are as described above and L represents a leaving group, e.g. SMeRX. The ring closure may be performed by treatment with Dowex 2×8 400 mesh OH⁻ resin in a suitable solvent, e.g. MeCN (acetonitrile). Alternatively, the ring closure may be performed by treatment with potassium carbonate in a suitable solvent, e.g. MeCN. Generally R will represent alkyl or aralkyl and X will represent halide, especially iodide or sulphate.

A compound of formula (X) in which L represents SMeRX may be formed from a compound of formula (XI)

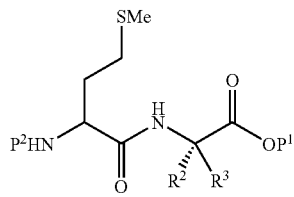

(XI)

by treatment with RX, where $P^1$ and $P^2$ are as described above and RX is a compound (e.g. MeI, benzyl iodide or $Me_2SO_4$) capable of converting sulphur in the SMe moiety to a sulfonium salt, in a suitable solvent, e.g. propanone or acetonitrile. Protection of the amine is convenient, although not essential, for this reaction.

A compound of formula (XI) may be prepared by reacting a compound of formula (XII) with a compound of formula (XIII):

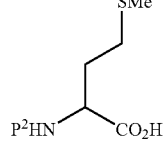

(XII)

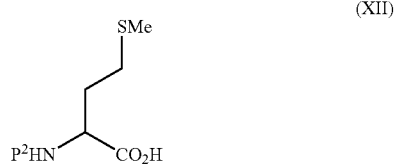

(XIII)

Suitably, the reaction may be carried out in the presence of a coupling agent, for example 1-[3-(dimethylamino)propyl]-3-ethyl carbodiimide hydrochloride, HOBt, a base, e.g. $Et_3N$, and an organic solvent, e.g. DCM, suitably at room temperature.

Compounds of formulae (III), (VI), (VIII), (X), (XI), (XII) and (XIII) are known compounds and/or can be prepared by processes well known in the art.

The various general methods described above may be useful for the introduction of the desired groups at any stage in the stepwise formation of the required compound, and it will be appreciated that these general methods can be combined in different ways in such multi-stage processes. The sequence of the reactions in multi-stage processes should of course be chosen so that the reaction conditions used do not affect groups in the molecule which are desired in the final product. For example, those skilled in the art will appreciate that, with the use of appropriate protecting groups, the coupling to any of groups —$R^1$, —$SO_2R^6$ or —$NR^4R^5$ can be the final step in the preparation of a compound of formula (I). Hence, in another aspect of the invention, the final step in the preparation of a compound of formula (I) may comprise the coupling to group —$R^1$ by reacting a compound of formula (XIV) with a compound of formula (VI) under the conditions described above:

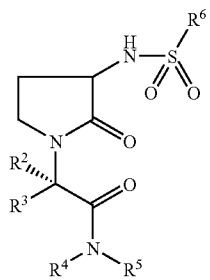

(XIV)

Suitably, where X is a leaving group such as a halogen atom, e.g. bromine, the reaction is carried out in the presence of a base, e.g. potassium carbonate. Preferably, the reaction is effected in a suitable solvent, e.g. DMF, suitably at room temperature.

A compound of formula (XIV) may be prepared by reacting a compound of formula (V) wherein $P^1$ is hydrogen with a compound of formula (III) under the conditions described above.

In a further aspect of the present invention, the final step in the preparation of a compound of formula (I) may comprise the coupling to group —$SO_2R^6$ by reacting a compound of formula (XV) with a compound of formula (VIII) under the conditions described above:

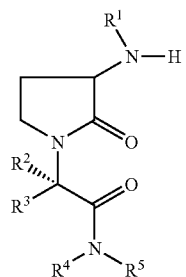

(XV)

The reaction is conveniently carried out in the presence of a base, e.g. pyridine, and in a suitable solvent, e.g. DCM, suitably at room temperature.

A compound of formula (XV) may be prepared by reacting a compound of formula (VII) with a compound of formula (VI) followed by deprotection and reaction with a compound of formula (III) under the conditions described above.

Those skilled in the art will appreciate that in the preparation of the compound of formula (I) or a solvate thereof it may be necessary and/or desirable to protect one or more sensitive groups in the molecule to prevent undesirable side reactions. Suitable protecting groups for use according to the present invention are well known to those skilled in the art and may be used in a conventional manner. See, for example, "Protective groups in organic synthesis" by T. W. Greene and P. G. M. Wuts (John Wiley & sons 1991) or "Protecting Groups" by P. J. Kocienski (Georg Thieme Verlag 1994). Examples of suitable amino protecting groups include acyl type protecting groups (e.g. formyl, trifluoroacetyl, acetyl), aromatic urethane type protecting groups (e.g. benzyloxycarbonyl (Cbz) and substituted Cbz), aliphatic urethane protecting groups (e.g. 9-fluorenylmethoxycarbonyl (Fmoc), t-butyloxycarbonyl (Boc), isopropyloxycarbonyl, cyclohexyloxycarbonyl) and alkyl or aralkyl type protecting groups (e.g. benayl, trityl, chlorotrityl). Examples of suitable oxygen protecting groups may include for example alkyl silyl groups, such as trimethylsilyl or tert-butyldimethylsilyl; alkyl ethers such as tetrahydropyranyl or tert-butyl; or esters such as acetate.

Various intermediate compounds used in the above-mentioned process, including but not limited to certain compounds of formulae formulae (II), (IV), (V), (VII), (IX), (XIV) and (XV) are novel and accordingly constitute a further aspect of the present invention.

The present invention will now be further illustrated by the accompanying examples which should not be construed as limiting the scope of the invention in any way.

All publications, including but not limited to patents and patent applications, cited in this specification are herein incorporated by reference as if each individual publication were specifically and individually indicated to be incorporated by reference herein as though fully set forth.

EXAMPLES

| Abbreviations | |
|---|---|
| BOC | t-Butyloxycarbonyl |
| Cbz or Z | Benzyloxycarbonyl |
| THF | Tetrahydrofuran |
| DCM | Dichloromethane |
| HOBT | 1-Hydroxybenzotriazole |
| br | broad |
| m | multiplet |
| q | quartet |
| s | singlet |
| t | triplet |

Example 1

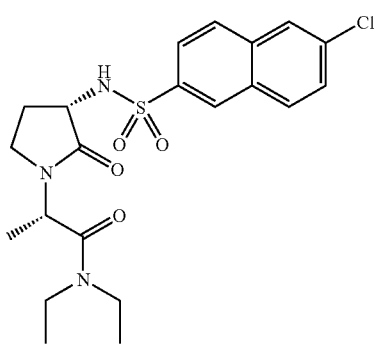

(2S)-2-((3S)-3-{[(6-Chloro-2-naphthyl)sulfonyl] amino}-2-oxopyrrolidin-1-yl)-N,N-diethylpropanamide To a solution of (2S)-2-((3S)-3-{[(6-chloro-2-naphthyl) sulfonyl]amino}-2-oxopyrrolidin-1-yl)propanoic acid (0.015 g) in DMF (1 ml) were added 1-[3-(dimethylamino) propyl]-3-ethylcarbodiimide hydrochloride (0.015 g), HOBT (0.01 g) and triethylamine (0.007 ml) and the mixture was stirred at room temperature for 30 min. Diethylamine (0.007 ml) was added and the resultant mixture stirred at room temperature for 16 h. The mixture was concentrated under reduced pressure and the residue was purified by mass directed preparative h.p.l.c. to give the title compound (0.008 g) as a colourless oil.

Mass spectrum: Found: MH$^+$452. H.p.l.c. (1) Rt 3.21 min

Using similar chemistry, the following were prepared:

Example 2

(2S)-2-((3S)-3-{[(6-Chloro-2-naphthl)sulfonyl]amino}-2-oxopyrrolidin-1-yl)-N-ethyl-N-(pyridin-4-ylmethyl)propanamide Mass spectrum: Found: MH$^+$ 515. H.p.l.c. (1) Rt 2.75 min

Example 3

(2S)-2-((3S)-3-}[(6-Chloro-2-naphthyl)sulfonyl]amino}-2-oxopyrrolidin-1-yl)-N-ethyl-N-methylpropanamide Mass spectrum: Found: MH$^+$ 438. H.p.l.c. (1) Rt 2.98 min

Example 4

(2S)-2-((3S)-3-{[(6-Chloro-2-naphthyl)sulfonyl]amino}-2-oxopyrrolidin-1-yl)-N-methyl-N-(2-phenylethyl)propanamide Mass spectrum: Found: MH$^+$ 514. H.p.l.c. (1) Rt 3.48 min

Example 5

(2S)-2-((3S)-3-{[(6-Chloro-2-naphthyl)sulfonyl]amino}-2-oxopyrrolidin-1-yl)-N-ethyl-N-(2-phenylethyl)propanamide Mass spectrum: Found: MH$^+$ 528. H.p.l.c. (1) Rt 3.59 min

Example 6

(2S)-2-((3S)-3-{[(6-Chloro-2-naphthyl)sulfonyl]amino}-2-oxopyrrolidin-1-yl)-N,N-dipropylpropanamide Mass spectrum: Found: MH$^+$ 480. H.p.l.c.(1) Rt 3.48 min

Example 7

(2S)-2-((3S)-3-{[(6-Chloro-2-naphthyl)sulfonyl]amino}-2-oxopyrrolidin-1-yl)-N-ethyl-N-isopropylpropanamide Mass spectrum; Found: MH$^+$ 464. H.p.l.c. (1) Rt 3.32 min

Example 8

(2S)-2-((3S)-3-{[(6-chloro-2-naphthyl)sulfonyl]amino}-2-oxopyrrolidin-1-yl)-N-methyl-N-(2-pyridin-2-ylethyl propanamide Mass spectrum: Found: MH$^+$ 515. H.p.l.c. (1) Rt 2.77 min

Example 9

(2S)-2-((3S)-3-{[(6-Chloro-2-naphthyl)sulfonyl]amino}-2-oxopyrrolidin-1-yl)-N-methyl-N-(pyridin-3-ylmethyl)propanamide Mass spectrum: Found: MH$^+$ 501. H.p.l.c. (1) Rt 2.81 min

Example 10

(2S)-2-((3S)-3-{[(6-chloro-2-naphthyl)sulfonyl]amino}-2-oxopyrrolidin-1-yl)-N-isopropyl-N-(pyridin-4-ylmethyl)propanamide Mass spectrum: Found: MH$^+$ 529. H.p.l.c. (1) Rt 2.75 min

Example 11

(2S)-2-((3S)-3-{[(6-Chloro-2-naphthyl1sulfonyl]amino}-2-oxopyrrolidin-1-yl)-N-isobutyl-N-(pyridin-2-ylmethyl)propanamide Mass spectrum: Found: MH$^+$ 543. H.p.l.c. (1) Rt 3.35 min

Example 12

(2S)-2-((3S)-3-{[(6-chloro-2-naphthyl)sulfonyl]amino}-2-oxopyrrolidin-1-yl)-N-propyl-N-(pyridin-2-ylmethyl)propanamide Mass spectrum: Found: MH$^+$ 529. H.p.l.c. (1) Rt 3.22 min

Example 13

(2S)-2-((3S)-3-{[(6-Chloro-2-naphthyl)sulfonyl]amino}-2-oxopyrrolidin-1-yl)-N-isopropyl-N-(pyridin-3-ylmethyl)propanamide Mass spectrum: Found: MH$^+$ 529. H.p.l.c. (1) Rt 2.90 min

Example 14

(2S)-N-(2-Azepan-1-ylethyl)-2-((3S)-3-{[(6-chloro-2-naphthyl)sulfonyl]amino}-2-oxopyrrolidin-1-yl)-N-isopropylpropanamide formate Mass spectrum: Found: MH$^+$ 563. H.p.l.c. (1) Rt 2.83 min

Example 15

(2S)-2-((3S)-3-{[(6-Chloro-2-naphthyl)sulfonyl]amino}-2-oxopyrrolidin-1-yl)-N-(2-cyanoethyl)-N-isopropylpropanamide Mass spectrum: Found: MH$^+$ 491. H.p.l.c. (1) Rt 3.23 min

Example 16

(2S)-2-((3S)-3-{[(6-Chloro-2-naphthyl)sulfonyl]amino}-2-oxopyrrolidin-1-yl)propanoyl)-N-isopropyl-beta-alaninamide Mass spectrum: Found: MH$^+$ 509. H.p.l.c. (1) Rt 2.97 min

Example 17

(2S)-2-((3S)-3-{[(6-Chloro-2-naphthyl)sulfonyl]
amino}-2-oxopyrrolidin-1-yl)-N-(2-hydroxyethyl)-
N-isopropylpropanamide Mass spectrum: Found: MH$^+$ 482. H.p.l.c. (1) Rt 3.05 min

Example 18

(2S)-2-((3S)-3-{[(6-Chloro-2-naphthyl)sulfonyl]
amino}-2-oxopyrrolidin-1-yl)-N-(2-cyanoethyl)-N-
(cyclopropylmethyl)propanamide Mass spectrum: Found: MH$^+$ 503. H.p.l.c. (1) Rt 3.30 min

Example 19

(2S)-2-((3S)-3-{[(6-Chloro-2-naphthyl)sulfonyl]
amino}-2-oxopyrrolidin-1-yl)-N-(2-cyanoethyl)-N-
isobutylpropanamide Mass spectrum: Found: MH$^+$ 505. H.p.l.c. (1) Rt 3.37 min

Example 20

(2S)-2-((3S)-3-{[(6-Chloro-2-naphthyl)sulfonyl]
amino}-2-oxopyrrolidin-1-yl)-N,N-dimethylpro-
panamide Mass spectrum: Found: MH$^+$ 424. H.p.l.c. (1) Rt 2.89 min

Example 21

(2S)-2-((3S)-3-{[(6-Chloro-2-naphthyl)sulfonyl]
amino}-2-oxopyrrolidin-1-yl-N-isopropyl-N-methyl-
propanamide Mass spectrum: Found: MH$^+$ 452. H.p.l.c. (1) Rt 3.08 min

Example 22

(2S)-2-((3S)-3-{[(6-Chloro-2-naphthyl)sulfonyl]
amino}-2-oxopyrrolidin-1-yl)-N-(2-hydroxyethyl)-
N-methylpropanamide Mass spectrum: Found: MH$^+$ 454. H.p.l.c. (1) Rt 2.78 min

Example 23

(2S)-2-((3S)-3-{[(6-Chloro-2-naphthyl)sulfonyl]
amino}-2-oxopyrrolidin-1-yl)-N-(2-cyanoethyl)-N-
methylpropanamide Mass spectrum: Found: MH$^+$ 463. H.p.l.c. (1) Rt 2.95 min

Example 24

(2S)-N-(2-Amino-2-oxoethyl)-2-((3S)-3-{[(6-chloro-
2-naphthyl)sulfonyl]amino}-2-oxopyrrolidin-1-yl)-
N-methylpropanamide Mass spectrum: Found: MH$^+$ 467. H.p.l.c. (1) Rt 2.73 min

Example 25

(2S)-2(3S)-3-{[(6-Chloro-2-naphthyl)sulfonyl]
amino}-2-oxopyrrolidin-1-yl)-N-[2-(dimethy-
lamino)-2-oxoethyl]-N-methylpropanamide Mass spectrum: Found: MH$^+$ 495. H.p.l.c. (1) Rt 2.84 min

Example 26

(2S)-2-((3S)-3-{[(6-Chloro-2-naphthyl)sulfonyl]
amino}-2-oxopyrrolidin-1-yl)-N-ethyl-N-(3-hydrox-
ypropyl)propanamide Mass spectrum: Found: MH$^+$ 507. H.p.l.c. (1) Rt 2.32 min

Example 27

(2S)-2-((3S)-3-{[(6-Chloro-2-naphthyl)sulfonyl]
amino}-2-oxopyrrolidin-1-yl)-N-methyl-N-(2-pyrro-
lidin-1-ylethyl)propanamide formate Mass spectrum: Found: MH$^+$ 523. H.p.l.c. (1) Rt 2.30 min

Example 28

(2S)-2-((3S)-3-{[(6-Chloro-2-naphthyl)sulfonyl]
amino}-2-oxopyrrolidin-1-yl)-N-methyl-N-(2-mor-
pholin-4-ylethyl)propanamide formate Mass spectrum: Found: MH$^+$ 537. H.p.l.c. (1) Rt 2.33 min

Example 29

(2S)-2-((3S)-3-{[(6-Chloro-2-naphthyl)sulfonyl]
amino}-2-oxopyrrolidin-1-yl)-N-ethyl-N-(2-morpho-
lin-4-ylethyl)propanamide formate Mass spectrum: Found: MH$^+$ 536. H.p.l.c. (1) Rt 2.33 min

Example 30

(2S)-2-((3S)-3-{[(6-Chloro-2-naphthyl)sulfonyl]
amino}-2-oxopyrrolidin-1-yl)-N-[2-(dimethylamino)
ethyl]-N-ethylpropanamide formate Mass spectrum: Found: MH$^+$ 495. H.p.l.c. (1) Rt 2.32 min

Example 31

(2S)-2-((3S)-3-{[(6-Chloro-2-naphthyl)sulfonyl]
amino}-2-oxopyrrolidin-1-yl)-N-isopropyl-N-(pyri-
din-2-ylmethyl)propanamide Mass spectrum: Found: MH$^+$ 529. H.p.l.c. (1) Rt 3.17 min

Example 32

(2S)-2-((3S)-3-{[(6-Chloro-2-naphthyl)sulfonyl]
amino}-2-oxopyrrolidin-1-yl)-N-ethyl-N-(2-pyridin-
2-ylethyl)propanamide Mass spectrum: Found: MH$^+$ 529. H.p.l.c. (1) Rt 2.92 min

Example 33

(2S)-2-((3S)-3-{[(6-Chloro-2-naphthyl)sulfonyl]amino}-2-oxopyrrolidin-1-yl)-N-methyl-N-(pyridin-2-ylmethyl)propanamide Mass spectrum: Found: MH$^+$ 501. H.p.l.c. (1) Rt 3.06 min

Example 34

(2S)-2-((3S)-3-{[(6-Chloro-2-naphthyl)sulfonyl]amino}-2-oxopyrrolidin-1-yl)-N-methyl-N-(2-pyridin-4-ylethyl)propanamide Mass spectrum: Found: MH$^+$ 515. H.p.l.c. (1) Rt 2.69 min

Example 35

(2S)-2-((3S)-3-{[(6-Chloro-2-naphthyl)sulfonyl]amino}-2-oxopyrrolidin-1-yl)-N-methyl-N-(pyridin-4-ylmethyl)propanamide Mass spectrum: Found: MH$^+$ 501. H.p.l.c. (1) Rt 2.75 min

Example 36

(2S)-2-((3S)-3-{[(6-Chloro-2-naphthyl)sulfonyl]amino}-2-oxopyrrolidin-1yl)-N-[2-(1 H-imidazol4-yl)ethyl]-N-methylpropanamide formate Mass spectrum: Found: MH$^+$ 504. H.p.l.c. (1) Rt 2.61 min

Example 37

(2S)-2-((3S)-3-{[(6-Chloro-2-naphthyl)sulfonyl]amino}-2-oxopyrrolidin-1-yl)-N-(2-cyanoethyl)-N-(pyridin-3-ylmethyl)propanamide Mass spectrum: Found: MH$^+$ 541. H.p.l.c. (1) Rt 2.51 min

Example 38

(2S)-2-((3S)-3-{[(6-Chloro-2-naphthyl)sulfonyl]amino}-2-oxopyrrolidin-1-yl)-N-ethyl-N-(2-hydroxyethyl)propanamide Mass spectrum: Found: MH$^+$ 469. H.p.l.c. (1) Rt 2.86 min

Example 39

(2S)-2-((3S)-3-{[(6-Chloro-2-naphthyl)sulfonyl]amino}-2-oxopyrrolidin-1-yl-N-(2-methoxyethyl)-N-methylpropanamide Mass spectrum: Found: MH$^+$ 469. H.p.l.c. (1) Rt 2.94 min

Example 40

(2S)-2-((3S)-3-{[(6-Chloro-2-naphthyl)sulfonyl]amino}-2-oxopyrrolidin-1-yl)-N-ethyl-N-(2-piperidin-1-ylethyl)propanamide formate Mass spectrum: Found: MH$^+$ 536. H.p.l.c. (1) Rt 2.38 min

Example 41

(2S)-2-((3S)-3-{[(6-Chloro-2-naphthyl)sulfonyl]amino}-2-oxopyrrolidin-1-yl)-N-isopropyl-N-(2-pyridin-2-ylethyl)propanamide Mass spectrum: Found: MH$^+$ 543. H.p.l.c. (1) Rt 2.48 min

Example 42

(2S)-2-((3S)-3-{[(6-Chloro-2-naphthyl)sulfonyl]amino}-2-oxopyrrolidin-1-yl)-N-(2-hydroxypropyl)-N-isopropylpropanamide Mass spectrum: Found: MH$^+$ 496. H.p.l.c. (1) Rt 3.07 min

Example 43

(2S)-2-((3S)-3-{[(6-Chloro-2-naphthyl)sulfonyl]amino}-2-oxopyrrolidin-1-yl)-N-(cyanomethyl)-N-isopropylpropanamide formate Mass spectrum: Found: MH$^+$ 477. H.p.l.c. (1) Rt 3.1 min

Example 44

(2S)-2-((3S)-3-{[(6-Chloro-2-naphthyl)sulfonyl]amino}-2-oxopyrrolidin-1-yl)-N-isopropyl-N-(3-methoxypropyl)propanamide Mass spectrum: Found: MH$^+$ 510. H.p.l.c. (1) Rt 3.16 min

Example 45

(2S)-2-((3S)-3-{[(6-Chloro-2-naphthyl)sulfonyl]amino}-2-oxopyrrolidin-1-yl)-N-isopropyl-N-(2-methoxyethyl)propanamide Mass spectrum: Found: MH$^+$ 496. H.p.l.c. (1) Rt 3.13 min

Example 46

(2S)-N-[2-(Acetylamino)ethyl]-2-((3S)-3-{[(6-chloro-2-naphthyl)sulfonyl]amino}-2-oxopyrrolidin-1-yl)-N-isopropylpropanamide Mass spectrum: Found: MH$^+$ 523. H.p.l.c. (1) Rt 2.9 min

Example 47

(2S)-N-Benzyl-2-((3S)-3-{[(6-chloro-2-naphthyl)sulfonyl]amino-2-oxopyrrolidin-1-yl)-N-isopropyl-propanamide Mass spectrum: Found: MH$^+$ 528. H.p.l.c. (1) Rt 3.47 min

Example 48

(2S)-2-((3S)-3-{[(6-Chloro-2-naphthyl)sulfonyl]amino}-2-oxopyrrolidin-1-yl)-N-isopropyl-N-(thien-2-ylmethyl)propanamide Mass spectrum: Found: MH$^+$ 534. H.p.l.c. (1) Rt 3.43 min

Example 49

(2S)-2-((3S)-3-{[(6-Chloro-2-naphthyl)sulfonyl]amino}-2-oxopyrrolidin-1-yl)-N-(3-hydroxypropyl)-N-isopropylpropanamide Mass spectrum: Found: MH+ 496. H.p.l.c. (1) Rt 2.95 min

Example 50

(2S)-2-((3S)-3-{[(6-Chloro-2-naphthyl)sulfonyl]amino}-2-oxopyrrolidin-1-yl)-N-(2-hydroxyethyl)-N-isopropylpropanamide Mass spectrum: Found: MH+ 482. H.p.l.c. (1) Rt 2.93 min

Example 51

(2S)-2-((3S)-3-{[(6-Chloro-2-naphthyl)sulfonyl]amino}-2-oxopyrrolidin-1-yl)-N-(3-hydroxypropyl)-N-(pyridin-4-ylmethyl)propanamide Mass spectrum: Found: MH+ 545. H.p.l.c. (1) Rt 2.30 min

Example 52

(2S)-2-((3S)-3-{[(6-Chloro-2-naphthyl)sulfonyl]amino}-2-oxopyrrolidin-1-yl)-N-(3-hydroxypropyl)-N-(pyridin-3-ylmethyl)propanamide Mass spectrum: Found: MH+ 545. H.p.l.c. (1) Rt 2.37 min

Example 53

(2S)-2-((3S)-3-{[(6-Chloro-2-naphthyl)sulfonyl]amino}-2-oxopyrrolidin-1-yl)-N-(3-hydroxypropyl)-N-(pyridin-2-ylmethyl)propanamide Mass spectrum: Found: MH+ 545. H.p.l.c. (1) Rt 2.59 min

Example 54

(2S)-2-((3S)-3-{[(6-Chloro-2-naphthyl)sulfonyl]amino}-2-oxopyrrolidin-1-yl)-N-(2-cyanoethyl)-N-(tetrahydrofuran-2-ylmethyl)propanamide Mass spectrum: Found: MH+ 503. H.p.l.c. (1) Rt 3.18 min

Example 55

(2S)-2-((3S)-3-{[(6-Chloro-2-naphthyl)sulfonyl]amino}-2-oxopyrrolidin-1-yl)-N-(2-cyanoethyl)-N-(cyclopropylmethyl)propanamide Mass spectrum: Found: MH+ 502. H.p.l.c. (1) Rt 3.19 min

Example 56

(2S)-2-((3S)-3-{[(6-Chloro-2-naphthyl)sulfonyl]amino}-2-oxopyrrolidin-1-yl)-N-(2-cyanoethyl)-N-(2-pyridin-2-ylethyl)propanamide Mass spectrum: Found: MH+ 554. H.p.l.c. (1) Rt 2.53 min

Example 57

(2S)-2-((3S)-3-{[(6-Chloro-2-naphthyl)sulfonyl]amino}-2-oxopyrrolidin-1-yl)-N-(2-cyanoethyl)-N-isobutylpropanamide Mass spectrum: Found: MH+ 505. H.p.l.c. (1) Rt 3.25 min

Example 58

(2S)-2-((3S)-3-{(2-Amino-2-oxoethyl)[(6-chloro-2-naphthyl)sulfonyl]amino}-2-oxopyrrolidin-1-yl)-N-ethyl-N-(pyridin-4-ylmethyl)propanamide Mass spectrum: Found: MH+ 572. H.p.l.c. (2) Rt 10.8 min

Example 59

(2S)-2-((3S)-3-{(2-Amino-2-oxoethyl)[(6-chloro-2-naphthyl)sulfonyl]amino}-2-oxopyrrolidin-1-yl)-N-ethyl-N-(2-pyridin-2-ylethyl)propanamide Mass spectrum: Found: MH+ 586. H.p.l.c. (2) Rt 10.96 min

Example 60

(2S)-2-((3S)-3-{(2-amino-2oxoethyl)[(6-chloro-2-naphthyl)sulfonyl]amino}-2-oxopyrrolidin-1-yl)-N-ethyl-N-(2-hydroxyethyl)propanamide Mass spectrum: Found: MH+ 525. H.p.l.c. (2) Rt 10.5 min

Example 61

(2S)-2-((3S)-3-{(2-Amino-2-oxoethyl)[(6-chloro-2-naphthyl)sulfonyl]amino}-2-oxopyrrolidin-1-yl)-N-isopropyl-N-(pyridin-2-ylmethyl)propanamide Mass spectrum: Found: MH+ 586. H.p.l.c. (1) Rt 3.05 min

Example 62

(2S)-2-((3S)-3-{(2-Amino-2-oxoethyl)[(6-chloro-2-naphthyl)sulfonyl]amino}-2-oxopyrrolidin-1-yl)-N-methyl-N-(pyridin-2-ylmethyl)propanamide Mass spectrum: Found: MH+ 558. H.p.l.c. (1) Rt 2.94 min

Example 63

(2S)-2-((3S)-3-{(2-Amino-2-oxoethyl)[(6-chloro-2-naphthyl)sulfonyl]amino}-2-oxopyrrolidin-1-yl)-N-methyl-N-(pyridin-3-ylmethyl)propanamide Mass spectrum: Found: MH+ 558. H.p.l.c. (1) Rt 2.78 min

Example 64

(2S)-2-((3S)-3-{(2-Amino-2-oxoethyl)[(6-chloro-2-naphthyl)sulfonyl]amino}-2-oxopyrrolidin-1-yl)-N-methyl-N-(2-pyridin-4-ylethyl)propanamide Mass spectrum: Found: MH$^+$ 572. H.p.l.c. (1) Rt 2.64 min

Example 65

(2S)-2-((3S)-3-{(2-Amino-2-oxoethyl)[(6-chloro-2-naphthyl)sulfonyl]amino}-2-oxopyrrolidin-1-yl)-N-methyl-N-(pridin-4-ylmethyl)propanamide Mass spectrum: Found: MH$^+$ 558. H.p.l.c. (1) Rt 2.68 min

Example 66

(2S)-2-((3S)-3-{(2-Amino-2-oxoethyl)[(6-chloro-2-naphthyl)sulfonyl]amino}-2-oxopyrrolidin-1-yl)-N-[2-(1H-imidazol-4-yl)ethyl]-N-methylpropanamide formate Mass spectrum: Found: MH$^+$ 561. H.p.l.c. (1) Rt 2.57 min

Example 67

(2S)-2-((3S)-3-{(2-Amino-2-oxoethyl)[(6-chloro-2-naphthyl)sulfonyl]amino}-2-oxopyrrolidin-1-yl)-N-methyl-N-(2-pyridin-2-ylethyl)propanamide Mass spectrum: Found: MH$^+$ 572. H.p.l.c. (1) Rt 2.73 min

Example 68

(2S)-2-((3S)-3-{(2-Amino-2-oxoethyl)[(6-chloro-2-naphthyl)sulfonyl]amino}-2-oxopyrrolidin-1-yl)-N-methyl-N-(2-phenylethyl)propanamide Mass spectrum: Found: MH$^+$ 571. H.p.l.c. (1) Rt 3.34 min

Example 69

(2S)-2-((3S)-3-{(2-Amino-2-oxoethyl)[(6-chloro-2-naphthyl)sulfonyl]amino}-2-oxopyrrolidin-1-yl)-N-ethyl-N-(2-phenylethyl)propanamide Mass spectrum: Found: MH$^+$ 585. H.p.l.c. (1) Rt 3.44 min

Example 70

(2S)-2-((3S)-3-{(2-Amino-2-oxoethyl)[(6-chloro-2-naphthyl)sulfonyl]amino}-2-oxopyrrolidin-1-yl)-N,N-dimethylpropanamide Mass spectrum: Found: MH$^+$ 481. H.p.l.c. (1) Rt 2.78 min

Example 71

(2S)-2-((3S)-3-{(2-Amino-2-oxoethyl)[(6-chloro-2-naphthyl)sulfonyl]amino}-2-oxopyrrolidin-1-yl)-N-isopropyl-N-methylpropanamide Mass spectrum: Found: MH$^+$ 509. H.p.l.c. (1) Rt 2.95 min

Example 72

(2S)-2-((3S)-3-{(2-Amino-2-oxoethyl)[(6-chloro-2-naphthyl)sulfonyl]amino}-2-oxopyrrolidin-1-yl)-N-(2-hydroxyethyl)-N-methylpropanamide Mass spectrum: Found: MH$^+$ 511. H.p.l.c. (1) Rt 2.70 min

Example 73

(2S)-2-((3S)-3-{(2-Amino-2-oxoethyl)[(6-chloro-2-naphthyl)sulfonyl]amino}-2-oxopyrrolidin-1-yl)-N-(2-hydroxyethyl)-N-isopropylpropanamide Mass spectrum: Found: MH$^+$ 539. H.p.l.c. (1) Rt 2.83 min

Example 74

(2S)-2-((3S)-3-{(2-Amino-2-oxoethyl)[(6-chloro-2-naphthyl)sulfonyl]amino}-2-oxopyrrolidin-1-yl)-N-(2-cyanoethyl)-N-methylpropanamide Mass spectrum: Found: MH$^+$ 520. H.p.l.c. (1) Rt 2.83 min

Example 75

(2S)-N-(2-Amino-2-oxoethyl)-2-((3S)-3-{(2-amino-2-oxoethyl)[(6-chloro-2-naphthyl)sulfonyl]amino}-2-oxopyrrolidin-1-yl)-N-methylpropanamide Mass spectrum: Found: MH$^+$ 524. H.p.l.c. (1) Rt 2.66 min

Example 76

(2S)-2-((3S)-3-{(2-Amino-2-oxoethyl)[(6-chloro-2-naphthyl)sulfonyl]amino}-2-oxopyrrolidin-1-yl)-N-[2-(dimethylamino)-2-oxoethyl]-N-methylpropanamide Mass spectrum: Found: MH$^+$ 552. H.p.l.c. (1) Rt 2.74 min

Example 77

(2S)-2-((3S)-3-{(2-Amino-2-oxoethyl)[(6-chloro-2-naphthyl)sulfonyl]amino}-2-oxopyrrolidin-1-yl)-N-ethyl-N-(3-hydroxypropyl)propanamide Mass spectrum: Found: MH$^+$ 539. H.p.l.c. (1) Rt 2.79 min

Example 78

(2S)-2-((3S)-3-{(2-Amino-2-oxoethyl)[(6-chloro-2-naphthyl)sulfonyl]amino}-2-oxopyrrolidin-1-y)-N-methyl-N-(2-pyrrolidin-1-ylethyl)propanamide formate Mass spectrum: Found: MH$^+$ 564. H.p.l.c. (1) Rt 2.27 min

Example 79

(2S)-2-((3S)-3-{(2-Amino-2-oxoethyl)[(6-chloro-2-naphthyl)sulfonyl]amino}-2-oxopyrrolidin-1-yl)-N-methyl-N-(2-morpholin-4-ylethyl)propanamide formate Mass spectrum: Found: MH$^+$ 580. H.p.l.c. (1) Rt 2.25 min

Example 80

(2S)-2-((3S)-3-{(2-Amino-2-oxoethyl)[(6-chloro-2-naphthyl)sulfonyl]amino}-2-oxopyrrolidin-1-yl)-N-ethyl-N-(2-morpholin-4-ylethyl)propanamide formate Mass spectrum: Found: MH$^+$ 594. H.p.l.c. (1) Rt 2.29 min

Example 81

(2S)-2-((3S)-3-{(2-Amino-2-oxoethyl)[(6-chloro-2-naphthyl)sulfonyl]amino}-2-oxopyrrolidin-1-yl)-N-[2-(dimethylamino)ethyl]-N-ethylpropanamide formate Mass spectrum: Found: MH$^+$ 552. H.p.l.c. (1) Rt 2.28 min

Example 82

(2S)-2-((3S)-3-{(2-Amino-2-oxoethyl)[(6-chloro-2-naphthyl)sulfonyl]amino}-2-oxopyrrolidin-1-yl)-N-(2-cyanoethyl)-N-(pyridin-3-ylmethyl)propanamide Mass spectrum: Found: MH$^+$ 598. H.p.l.c. (1) Rt 2.38 min

Example 83

(2S)-2-((3S)-3-{(2-Amino-2-oxoethyl)[(6-chloro-2-naphthyl)sulfonyl]amino}-2-oxopyrrolidin-1-yl)-N-ethyl-N-(2-hydroxyethyl)propanamide Mass spectrum: Found: MH$^+$ 526. H.p.l.c. (1) Rt 2.76 min

Example 84

(2S)-2-((3S)-3-{(2-Amino-2-oxoethyl)[(6-chloro-2-naphthyl)sulfonyl]amino}-2-oxopyrrolidin-1-yl)-N-(2-methoxyethyl)-N-methylpropanamide Mass spectrum: Found: MH$^+$ 526. H.p.l.c. (1) Rt 2.83 min

Example 85

(2S)-2-((3S)-3-{(2-Amino-2-oxoethyl)[(6-chloro-2-naphthyl)sulfonyl]amino}-2-oxopyrrolidin-1-yl)-N-ethyl-N-(2-piperidin-1-ylethyl)propanamide formate Mass spectrum: Found: MH$^+$ 593. H.p.l.c. (1) Rt 2.33 min

Example 86

(2S)-2-((3S)-3-{(2-Amino-2-oxoethyl)[(6-chloro-2-naphthyl)sulfonyl]amino}-2-oxopyrrolidin-1-yl)-N-(2-hydroxyethyl)-N-(2-morpholin-4-ylethyl)propanamide formate Mass spectrum: Found: MH$^+$ 610. H.p.l.c. (2) Rt 10.35 min

Example 87

(2S)-2-((3S)-3-{(2-Amino-2-oxoethyl)[(6-chloronaphth-2-yl)sulfonyl]amino}-2-oxopyrrolidin-1-yl)-N-ethyl-N-methylpropanamide Mass spectrum: Found: MH$^+$ 495. H.p.l.c. (1) Rt 2.96 min

Example 88

(2S)-2-((3S)-3-{(2-Amino-2-oxoethyl)[(6-chloronaphth-2-yl)sulfonyl]amino}-2-oxopyrrolidin-1-yl)-N,N-diethylpropanamide Mass spectrum: Found: MH$^+$ 509. H.p.l.c. (1) Rt 3.08 min

Example 89

(2S)-2-((3S)-3-{(2-Amino-2-oxoethyl)[(6-chloronaphth-2-yl)sulfonyl]amino}-2-oxopyrrolidin-1-yl)-N,N-dipropylpropanamide Mass spectrum: Found: MH$^+$ 537. H.p.l.c. (1) Rt 3.22 min

Example 90

(2S)-2-((3S)-3-{(2-Amino-2-oxoethyl)[(6-chloronaphth-2-yl)sulfonyl]amino}-2-oxopyrrolidin-1-yl)-N-ethyl-N-isopropylpropanamirde Mass spectrum: Found: MH$^+$ 523. H.p.l.c. (1) Rt 3.17 min

Example 91

(2S)-2-((3S)-3-{(2-Amino-2-oxoethyl)[(6-chloronaphth-2-yl)sulfonyl]amino}-2-oxopyrrolidin-1-yl)-N-isopropyl-N-(pyrid-4-ylmethyl-propanamide Mass spectrum: Found: MH$^+$ 586. H.p.l.c. (1) Rt 2.67 min

Example 92

(2S)-2-((3S)-3-{(2-Amino-2-oxoethyl)[(6-chloronaphth-2-yl)sulfonyl]amino}-2-oxopyrrolidin-1-yl)-N-(2-cyanoethyl)-N-isopropylpropanamide Mass spectrum: Found: MH$^+$ 548. H.p.l.c. (1) Rt 3.07 min

Example 93

(2S)-2-((3S)-3-{(2-Amino-2-oxoethyl)[(6-chloronaphth-2-yl)sulfonyl]amino}-2-oxopyrrolidin-1-yl)-N-(2-azepan-1-ylethyl)-N-isopropylpropanamide formate Mass spectrum: Found: MH$^+$ 620. H.p.l.c. (1) Rt 2.65 min

Example 94

(2S)-N-[2-(Acetylamino)ethyl]-2-((3S)-3-{(2-amino-2-oxoethyl)[(6-chloronaphth-2-yl)sulfonyl]amino}-2-oxopyrrolidin-1-yl)-N-isopropylpropanamide Mass spectrum: Found: MH$^+$ 580. H.p.l.c. (1) Rt 2.87 min

Example 95

(2S)-2-((3S)-3-{[(6-Chloro-2-naphthyl)sulfonyl]amino}-2-oxopyrrolidin-1-yl)-N-cyclopentyl-N-methylpropanamide Mass spectrum: Found: MH$^+$ 478. H.p.l.c. (1) Rt 3.23 min

Example 96

(2S)-2-((3S)-3-{[(6-Chloro-2-naphthyl)sulfonyl]amino}-2-oxopyrrolidin-1-yl)-N-cyclohexyl-N-ethylpropanamide Mass spectrum: Found: MH$^+$ 506. H.p.l.c. (1) Rt 3.45 min

Example 97

(2S)-2-((3S)-3-{[(6-Chloro-2-naphthyl)sulfonyl]amino}-2-oxopyrrolidin-1-yl)-N-cyclohexyl-N-methylpropanamide Mass spectrum: Found: MH$^+$ 492. H.p.l.c. (1) Rt 3.34 min

Example 98

(2S)-2-((3S)-3-{[(6-Chloro-2-naphthyl)sulfonyl]amino}-2-oxopyrrolidin-1-yl)-N-(2-cyanoethyl)-N-cyclopentylpropanamide Mass spectrum: Found: MH$^+$ 517. H.p.l.c. (1) Rt 3.25 min

Example 99

(2S)-2-((3S)-3-{[(6-Chloro-2-naphthyl)sulfonyl]amino}-2-oxopyrrolidin-1-yl)-N-(2-cyanoethyl)-N-cyclopropylpropanamide Mass spectrum: Found: MH$^+$ 489. H.p.l.c. (1) Rt 3.09 min

Example 100

(2S)-2-((3S)-3-{(2-Amino-2-oxoethyl)[(6-chloro-2-naphthyl)sulfonyl]amino}-2-oxopyrrolidin-1-yl)-N-methyl-N-(1-methylpiperidin-4-yl)propanamide formate Mass spectrum: Found: MH$^+$ 564. H.p.l.c. (1) Rt 2.40 min

Example 101

(2S)-2-((3S)-3-{[(6-Chloro-2-naphthyl)sulfonyl]amino}-2-oxopyrrolidin-1-yl)-N-ethyl-N-phenylpropanamide Mass spectrum: Found: MH$^+$ 501. H.p.l.c. (1) Rt 3.34 min

Example 102

(2S)-2-((3S)-3-{(2-Amino-2-oxoethyl)[(6-chloro-2-naphthyl)sulfonyl]amino}-2-oxopyrrolidin-1-yl)-N-(2-cyanoethyl)-N-cyclopentylpropanamide Mass spectrum: Found: MH$^+$ 574. H.p.l.c. (1) Rt 3.11 min

Example 103

(2S)-2-((3S)-3-{[(6-Chloro-2-naphthyl)sulfonyl]amino}-2-oxopyrrolidin-1-yl)-N-(2-cyanoethyl)-N-cyclohexylpropanamide Mass spectrum: Found: MH$^+$ 531. H.p.l.c. (1) Rt 3.34 min

Example 104

(2S)-2-((3S)-3-{(2-Amino-2-oxoethyl)[(6-chloro-2-naphthyl)sulfonyl]amino}-2-oxopyrrolidin-1-yl)-N-cyclohexyl-N-methylpropanamide Mass spectrum: Found: MH$^+$ 549. H.p.l.c. (1) Rt 3.19 min

Example 105

(2S)-2-((3S)-3-{(2-Amino-2-oxoethyl)[(6-chloro-2-naphthyl)sulfonyl]amino}-2-oxopyrrolidin-1-yl)-N-(2-cyanoethyl)-N-cyclopropylpropanamide Mass spectrum: Found: MH$^+$ 546. H.p.l.c. (1) Rt2.96 min

Example 106

(2S)-2-((3S)-3-{[(6-Chloro-2-naphthyl)sulfonyl]amino}-2-oxopyrrolidin-1-yl)-N-(2-cyanoethyl)-N-cyclobutylpropanamide Mass spectrum: Found: MH$^+$ 503. H.p.l.c. (1) Rt 3.18 min

Example 107

(2S)-2-((3S)-3-{[(6-Chloro-2-naphthyl)sulfonyl]amino}-2-oxopyrrolidin-1-yl)-N-cyclopropyl-N-(pyridin-4-ylmethyl)propanamide Mass spectrum: Found: MH$^+$ 527. H.p.l.c. (1) Rt 2.79 min

Example 108

(2S)-2-((3S)-3-(2-Amino-2-oxoethyl)[(6-chloro-2-naphthyl)sulfonyl]amino}-2-oxopyrrolidin-1-yl)-N-cyclopropyl-N-(pyridin-4-ylmethyl)propanamide Mass spectrum: Found: MH$^+$ 584. H.p.l.c. (1) Rt 2.70 min

Example 109

(2S)-N-[2-(Aminosulfonyl)ethyl]-2-((3S)-3-{[(6-chloro-2-naphthyl)sulfonyl]amino}-2-oxopyrrolidin-1-yl)-N-isopropylpropanamide Mass spectrum: Found: MH$^+$ 545. H.p.l.c. (1) Rt 3.06 min

Example 110

(2S)-2-((3S)-3-{(2-Amino-2-oxoethyl)[(6-chloro-2-naphthyl)sulfonyl]amino}-2-oxopyrrolidin-1-yl)-N-isopropyl-N-(2-piperidin-1-ylethyl)propanamide Mass spectrum: Found: MH$^+$ 606. H.p.l.c. (1) Rt 2.6 min

Example 111

(2S)-2-((3S)-3-{(2-Amino-2-oxoethyl)[(6-chloro-2-naphthyl)sulfonyl]amino}-2-oxopyrrolidin-1-yl)-N-isopropyl-N-(2-morpholin-4-ylethyl)propanamide Mass spectrum: Found: MH$^+$ 608. H.p.l.c. (1) Rt 2.55 min

Example 112

(2S)-2-((3S)-3-{[(6-Chloro-2-naphthyl)sulfonyl]
amino}-2-oxopyrrolidin-1-yl)-N-isopropyl-N-(2-
piperidin-1-ylethyl)propanamide Mass spectrum: Found: MH$^+$ 549. H.p.l.c. (1) Rt 2.64 min

Example 113

(2S)-2-((3S)-3-{[(6-Chloro-2-naphthyl)sulfonyl]
amino}-2-oxopyrrolidin-1-yl)-N-isopropyl-N-(2-
morpholin-4-ylethyl)propanamide Mass spectrum: Found: MH$^+$ 551. H.p.l.c. (1) Rt 2.57 min

Example 114

(2S)-2-((3S)-3-{(2-Amino-2-oxoethyl)[(6-chloro-2-
naphthyl)sulfonyl]amino}-2-oxopyrrolidin-1-yl)-N-
cyclohexyl-N-ethylpropanamide Mass spectrum: Found: MH$^+$ 563. H.p.l.c. (1) Rt 3.29 min

Example 115

(2S)-2-((3S)-3-{(2-Amino-2-oxoethyl)[(6-chloro-2-
naphthyl)sulfonyl]amino}-2-oxopyrrolidin-1-yl)-N-
(2-hydroxy-2-phenylethyl)-N-methylpropanamide Mass spectrum: Found: MH$^+$ 587. H.p.l.c. (1) Rt 3.01 min

Example 116

(2S)-2-((3S)-3-{(2-Amino-2-oxoethyl)[(6-chloro-2-
naphthyl)sulfonyl]amino}-2-oxopyrrolidin-1-yl)-N-
ethyl-N-phenylpropanamide Mass spectrum: Found: MH$^+$ 557. H.p.l.c. (1) Rt 3.16 min

Example 117

(2S)-2-((3S)-3-{[(6-Chloro-2-naphthyl)sulfonyl]
amino}-2-oxopyrrolidin-1-yl)-N-(2-hydroxy-2-phe-
nylethyl)-N-methylpropanamide Mass spectrum: Found: MH$^+$ 530. H.p.l.c. (1) Rt 3.16 min

Example 118

(2S)-2-((3S)-3-{[(6-Chloro-2-naphthyl)sulfonyl]
amino}-2-oxopyrrolidin-1-yl)-N,N-bis(2-hydroxy-
ethyl)propanamide Mass spectrum: Found: MH$^+$ 484. H.p.l.c. (1) Rt 2.79 min

Example 119

(2S)-2-((3S)-3-{[(6-Chloro-2-naphthyl)sulfonyl]
amino}-2-oxopyrrolidin-1-yl)-N-isopropyl-N-(1H-
pyrazol-3-ylmethyl)propanamide Mass spectrum: Found: MH$^+$ 518. H.p.l.c. (1) Rt 3.1 min

Example 120

(2S)-N-Allyl-2-((3S)-3-{[(6-chloro-2-naphthyl)sul-
fonyl]amino}-2-oxopyrrolidin-1-yl)-N-(pyridin-4-
ylmethyl)propanamide Mass spectrum: Found: MH$^+$ 527. H.p.l.c. (1) Rt 2.86 min

Example 121

(2S)-2-((3S)-3-{[(6-Chloro-2-naphthyl)sulfonyl]
amino}-2-oxopyrrolidin-1-yl)-N-isopropyl-N-[3-(4-
methylpiperazin-1-yl)propyl]propanamide formate Mass spectrum: Found: MH$^+$ 578. H.p.l.c. (1) Rt 2.53 min

Example 122 tert-Butyl 2-[[(2S)-2-((3S)-3-{(2-amino-2-oxoethyl)
[(6-chloro-2-naphthyl)sulfonyl]amino}-2-oxopyrro-
lidin-1-yl)propanoyl](isopropyl)amino]ethylcarbam-
ate Mass spectrum: Found: MH$^+$ 638. H.p.l.c. (1) Rt 3.28 min

Example 123 tert-Butyl 3-[[(2S)-2-((3S)-3-{[(6-chloro-2-naph-
thyl)sulfonyl]amino}-2-oxopyrrolidin-1-yl)pro-
panoyl](isopropyl)amino]propylcarbamate Mass spectrum: Found: MH$^+$ 595. H.p.l.c. (1) Rt 3.47 min

Example 124 tert-Butyl 2-[[(2S)-2-((3S)-3-{[(6-chloro-2-naph-
thyl)sulfonyl]amino}-2-oxopyrrolidin-1-yl)pro-
panoyl](cyclopropylmethyl)amino]ethylcarbamate Mass spectrum: Found: MH$^+$ 592. H.p.l.c. (1) Rt 3.53 min

Example 125

(2S)-2-((3S)-3-{(2-Amino-2oxoethyl)[(6-chloro-2-
naphthyl)sulfonyl]amino}-2-oxopyrrolidin-1-yl)-N-
isopropylpropanamide Mass spectrum: Found: MH$^+$ 495. H.p.l.c. (1) Rt 3.01 min

Example 126

(2S)-N-(42-tert-Butoxyethyl)-2-((3S)-3-{[(6-chloro-
2-naphthyl)sulfonyl]amino}-2-oxopyrrolidin-1-yl)-
N-(pyridin-4-ylmethyl)propanamide Mass spectrum: Found: MH$^+$ 587. H.p.l.c. (1) Rt 3.08 min

Example 127

(2S)-2-((3S)-3-{[(6-Chloro-2-naphthyl)sulfonyl]
amino}-2-oxopyrrolidin-1-yl)-N-(2-hydroxyethyl)-
N-(pyridin-4-ylmethyl)propanamide formate Example 126 (0.058 g) was dissolved in DCM (2 ml) and trifluoroacetic acid (3 ml) was added. After stirring for 4 h at room temperature, the mixture was concentrated under reduced pressure and the residue purified by mass directed preparative h.p.l.c. to give the title compound (0.003 g) as a white solid.

Mass spectrum: Found: MH$^+$ 531. H.p.l.c. (1) Rt 2.54 min

Example 128

(2S)-N-(2-Aminoethyl)-2-((3S)-3-{(2-amino-2-oxo-ethyl)[(6-chloro-2-naphthyl)sulfonyl]amino}-2-oxopyrrolidin-1-yl)-N-isopropylpropanamide hydrochloride Example 124 (0.12 g) was dissolved in 4N hydrochloric acid:dioxane (1:1, 5 ml) and stirred at room temperature for 4 h. The mixture was then concentrated under reduced pressure to give the title compound (0.9 g) as a beige solid.

Mass spectrum: Found: MH$^+$ 538. H.p.l.c. (1) Rt 2.5 min

Using similar chemistry and Example 125, the following was prepared:

Example 129

(2S)-N-(3-Aminopropyl)-2-((3S)-3-{[(6-chloro-2-naphthyl)sulfonyl]amino}-2-oxopyrrolidin-1-yl)-N-isopropylpropanamide hydrochloride Mass spectrum: Found: MH$^+$ 495. H.p.l.c. (1) Rt 2.56 min

Example 130

(2S)-N-(2-Aminoethyl)-2-((3S)-3-{[(6-chloro-2-naphthyl)sulfonyl]amino}-2-oxopyrrolidin-1-yl)-N-(cyclopropylmethyl)propanamide hydrochloride Mass spectrum: Found: MH$^+$ 493. H.p.l.c. (1) Rt 2.54 min

Example 131

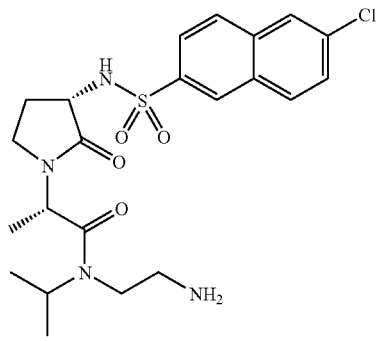

(2S)-N-(2-Aminoethyl)-2-((3S)-3-{[(6-chloro-2-naphthyl)sulfonyl]amino}-2-oxopyrrolidin-1-yl)-N-isopropylpropanamide tert-Butyl 2-[[(2S)-2-((3S)-3-{[(6-chloro-2-naphthyl)sulfonyl]amino}-2-oxopyrrolidin-1-yl)propanoyl](isopropyl)amino]ethylcarbamate (0.21 g) was dissolved in DCM (4 ml), and trifluoroacetic acid (4 ml) was added. The mixture was stirred at room temperature for 2.5 h and then concentrated under reduced pressure. The residue was partitioned between saturated sodium bicarbonate solution and DCM, and the organic layer was separated, dried (over magnesium sulphate) and concentrated under reduced pressure. The residue was purified using SPE (silica, eluting with DCM, diethyl ether, ethyl acetate, methanol and methanol:10% aqueous ammonia) to give the title compound (0.124 g) as a white solid.

Mass spectrum: Found: MH$^+$ 481. H.p.l.c. (1) Rt 2.5 min

Example 133

(2S)-N-(2-Amino-2-oxoethyl)-2-((3S)-3-{[(6-chloro-2-naphthyl)sulfonyl]amino}-2-oxopyrrolidin-1-yl)-N-isopropylpropanamide Using Intermediate 26 and ammonium chloride, and the synthetic procedure described for Example 1, the title compound was prepared.

Mass spectrum: Found: MH$^+$ 493. H.p.l.c. (1) Rt 2.94 min

Example 134

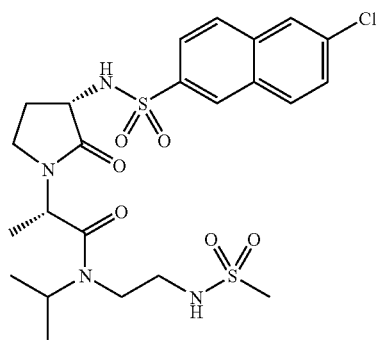

(2S)-2-((3S)-3-{[(6-Chloro-2-naphthyl)sulfonyl]amino}-2-oxopyrrolidin-1-yl)-N-isopropyl-N-{2-[(methylsulfonyl)amino]ethyl}propanamide (2S)-N-(2-Aminoethyl)-2-((3S)-3-{[(6-chloro-2-naphthyl)sulfonyl]amino}-2-oxopyrrolidin-1-yl)-N-isopropylpropanamide (0.04 g) was dissolved in DCM (3 ml) at 0° C. and was treated with pyridine (0.027 ml) and mesyl chloride (0.03 ml). The reaction mixture was allowed to reach room temperature and then stirred at room temperature for 3 h. Additional DCM (3 ml) followed by hydrochloric acid (5 ml) was added. The organic layer was separated, dried (over magnesium sulphate) and concentrated under reduced pressure. The residue was purified using SPE (silica, eluting with DCM, diethyl ether, ethyl acetate:10% aqueous NH$_3$) to give the title compound (0.024 g) as gum.

Mass spectrum: Found: MH$^+$ 559. H.p.l.c. (1) Rt 3.08 min

Using similar chemistry, the following was prepared:

Example 135

(2S)-2-((3S)-3-{(2-Amino-2-oxoethyl)[(6-chloro-2-naphthyl)sulfonyl]amino}-2-oxopyrrolidin-1-yl)-N-isopropyl-N-{2-[(methylsulfonyl)amino]ethyl}propanamide Mass spectrum: Found: MH$^+$ 616. H.p.l.c. (1) Rt 2.98 min

Example 136

(2S)-2-((3S)-3-{[(6-Chloro-2-naphthyl)sulfonyl]amino}-2-oxopyrrolidin-1-yl)-N-isopropyl-N-{3-[(methylsulfonyl)amino]propyl}propanamide Mass spectrum: Found: MH$^+$ 573. H.p.l.c. (1) Rt 3.12 min

Example 137

(2S)-2-((3S)-3-{[(6-Chloro-2-naphthyl)sulfonyl]amino}-2-oxopyrrolidin-1-yl)-N-(cyclopropylmethyl)-N-{2-[(methylsulfonyl)amino]ethyl}propanamide Mass spectrum: Found: MH$^+$ 571. H.p.l.c. (1) Rt 3.15 min

Example 138

(2S)-N-[2-({(E)-Amino[oxido(oxo)hydrazono]methyl}amino)ethyl]-2-((3S)-3-{[(6-chloro-2-naphthyl)sulfonyl]amino}-2-oxopyrrolidin-1-yl)-N-isopropylpropanamide (2S)-N-(2-Aminoethyl)-2-((3S)-3-{[(6-chloro-2-naphthyl)sulfonyl]amino}-2-oxopyrrolidin-1-yl)-N-isopropylpropanamide (0.035 g) was dissolved in ethanol (2 ml), treated with S-methyl-nitro-isothiourea (0.022 g) and stirred at room temperature for 18 h. The mixture was concentrated under reduced pressure and the residue purified by mass directed preparative h.p.l.c. to give the title compound (0.019 g) as a white solid.

Mass spectrum: Found: MH$^+$ 568. H.p.l.c. (1) Rt 3.07 min

Using similar chemistry, the following was prepared:

Example 139

(2S)-N-[2-({(E)-Amino[oxido(oxo)hydrazono]methyl}amino)ethyl]-2-((3S)-3-{(2-amino-2-oxoethyl)[(6-chloro-2-naphthyl)sulfonyl]amino}-2-oxopyrrolidin-1-yl)-N-isopropylpropanamide Mass spectrum: Found: MH$^+$ 625. H.p.l.c. (1) Rt 2.97 min

Example 140

(2S)-N-[3-({(E)-Amino[oxido(oxo)hydrazono]methyl}amino)propyl]-2-((3S)-3-{[(6-chloro-2-naphthyl)sulfonyl]amino}-2-oxopyrrolidin-1-yl)-N-isopropylpropanamide Mass spectrum: Found: MH$^+$ 582. H.p.l.c. (1) Rt 3.06 min

Example 141 and Example 142

(2S)-2-((3S)-3-{[(6-Chloro-2-naphthyl)sulfonyl]amino}-2-oxopyrrolidin-1-yl)-N-isopropyl-N-[2-(methylamino)ethyl]propanamide and (2S)-2-((3S)-3-{[(6-Chloro-2-naphthyl)sulfonyl]amino}-2-oxopyrrolidin-1-yl)-N-[2-(dimethylamino)ethyl]-N-isopropylpropanamide (2S)-N-(2-Aminoethyl)-2-((3S)-3-{[(6-chloro-2-naphthyl)sulfonyl]amino}-2-oxopyrrolidin-1-yl)-N-isopropylpropanamide (0.06 g) was dissolved in formic acid (2 ml), cooled to 0° C. and treated slowly with formaldehyde (2 ml). The mixture was heated to 50° C. for 18 h, cooled to room temperature and then basified to pH8 with sodium bicarbonate solution. The aqueous mixture was extracted with DCM, and the combined, dried (over magnesium sulphate) organic extracts concentrated under reduced pressure. The residue was purified using SPE (silica, eluting with DCM:methanol aqueous ammonia 200:5:2) to give Example 143 (0.027 g) and Example 144 (0.017 g), both as colourless gums.

Example 141

Mass spectrum: Found: MH$^+$ 494. H.p.l.c. (1) Rt 2.61 min

Example 142

Mass spectrum: Found: MH$^+$ 508. H.p.l.c. (1) Rt 2.62 min

Example 143

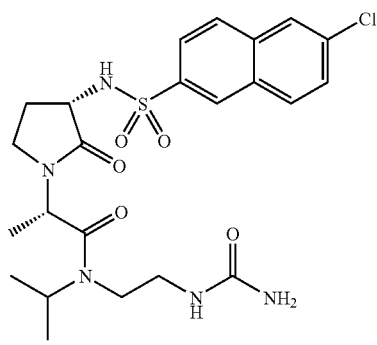

(2S)-N-{2-[(Aminocarbonyl)amino]ethyl}-2-((3S)-3-{[(6-chloro-2-naphthyl)sulfonyl]amino}-2-oxopyrrolidin-1-yl)-N-isopropylpropanamide (2S)-N-(2-Aminoethyl)-2(3S)-3-{[(6-chloro-2-naphthyl)sulfonyl]amino}-2-oxopyrrolidin-1-yl)-N-isopropylpropanamide (0.02 g) was dissolved in THF (2 ml) and treated with N-methyl morpholine (0.183 ml) followed by phenyl carbamate (0.034 g), and the resultant mixture heated under reflux for 18 h. The reaction mixture was concentrated under reduced pressure and the residue triturated with methanol. The resultant suspension was filtered and the filtrate was separated using SPE (silica, eluting with DCM, ethyl acetate, methanol, methanol:10% aqueous NH$_3$) to give an impure sample of the title compound, which was further purified using mass directed preparative h.p.l.c. to give the title compound (0.01 g) as an oil.

Mass spectrum: Found: MH$^{-1}$ 522. H.p.l.c. (1) Rt 2.90 min

Using similar chemistry, the following was prepared:

Example 144

(2S)-N-{2-[(Aminocarbonyl)amino]ethyl}-2-((3S)-3-{(2-amino-2-oxoethyl)[(6-chloro-2-naphthyl)sulfonyl]amino}-2-oxopyrrolidin-1-yl)-N-isopropylpropanamide Mass spectrum: Found: MH$^+$ 581. H.p.l.c. (1) Rt 2.78 min

Example 145

(2S)-N-{2-[(Aminocarbonyl)amino]ethyl}-2-((3S)-3-{[(6-chloro-2-naphthyl)sulfonyl]amino}-2-oxopyrrolidin-1-yl)-N-(cyclopropylmethyl)propanamide Mass spectrum: Found: MH$^+$ 536. H.p.l.c. (1) Rt 2.96 min

Example 146

(2S)-N-{3-[(Aminocarbonyl)amino]propyl}-2-((3S)-3-{[(6-chloro-2-naphthyl)sulfonyl]amino}-2-oxopyrrolidin-1-yl)-N-isopropylpropanamide Example 131 (0.03 g) was dissolved in dry THF (3 ml) and treated with N,N-diisopropylethlamine (0.039 ml) and phenyl carbamate (0.047 g) and then heated under reflux for 4 h. The cooled reaction mixture was concentrated under reduced pressure and the residue purified using mass directed preparative h.p.l.c. to give the title compound (0.014 g) as a pale yellow solid.

Mass spectrum: Found: $MH^{-1}$ 535. H.p.l.c. (1) Rt 2.95 min

Example 147

(2S)-2-((3S)-3-{[(6-Chloro-2-naphthyl)sulfonyl]amino}-2-oxopyrrolidin-1-yl)-N-(cyclopropylmethyl)-N-(2-hydroxyethyl)propanamide Intermediate 20 (0.05 g) was dissolved in dry THF (5 ml) and tetrabutylammonium fluoride (0.028 g) was added. After stirring at room temperature for 4 h, a further quantity of tetrabutylammonium fluoride (0.014 g) was added. After 1 h, the mixture was concentrated under reduced pressure and the residue was partitioned between DCM and water. The separated organic component was dried (over magnesium sulphate), filtered and concentrated under reduced pressure. The residue was partially purified using SPE (silica, eluting with cyclohexane:ethyl acetate, 20:1 to 1:1) to give an impure sample of the title compound. Further purification using mass directed preparative h.p.l.c. provided the title compound (0.014 g) as a colourless gum.

Mass spectrum: Found: $MH^+$ 494. H.p.l.c. (1) Rt 3.06 min

Example 148

(2S)-2-((3S)-3-{[(5'-Chloro-2,2'-bithien-5-yl)sulfonyl]amino}-2-oxopyrrolidin-1-yl)-N-ethyl-N-isopropylpropanamide Using Intermediate 25 and 5'-chloro-2,2'-bithiophene-5-sulfonyl chloride, and the chemistry described for the preparation of Intermediate 4, the title compound was prepared.

Mass spectrum: Found: $MH^+$ 504. H.p.l.c. (1) Rt 3.41 min

Using similar chemistry, the following were prepared:

Example 149

(2S)-2-((3S)-3-{[(6-Chloro-1-benzothien-2-yl)sulfonyl]amino}-2-oxopyrrolidin-1-yl)-N-ethyl-N-isopropylpropanamide Mass spectrum: Found: $MH^+$ 472. H.p.l.c. (1) Rt 3.21 min

Example 150

(2S)-2-[(3S)-3-({[(E)-2-(5-Chlorothien-2-yl)ethenyl]sulfonyl}amino)-2-oxopyrrolidin-1-yl]-N-ethyl-N-isopropylpropanamide Mass spectrum: Found: $MH^+$ 448. H.p.l.c. (1) Rt 3.05 min

Example 151

(2S)-2-[(3S)-3-({[(E)-2-(4-Chlorophenyl)ethenyl]sulfonyl}amino)-2-oxopyrrolidin-1-yl]-N-ethyl-N-isopropylpropanamide Mass spectrum: Found: $MH^+$ 442. H.p.l.c. (1) Rt 3.09 min

Example 152 tert-Butyl 2-{[(2S)-2-((3S)-3-{[(6-chloro-2-naphthyl)sulfonyl]amino}-2-oxopyrrolidin-1-yl)propanoyl]amino}ethylcarbamate Using 2-(1H-benzotriazole-1-yl)-1,1,3,3-tetramethyluronium tetrafluoroborate, and the synthetic procedure described for Example 1, the title compound was prepared.

Mass spectrum: Found: $MH^+$ 539. H.p.l.c. (1) Rt 3.15 min

Using similar chemistry, the following was prepared:

Example 153

(2S)-2-((3S)-3-{[(6-Chloro-2-naphthyl)sulfonyl]amino}-2-oxopyrrolidin-1-yl)-N-(2-piperidin-1-ylethyl)propanamide Mass spectrum: Found: $MH^+$ 507. H.p.l.c. (1) Rt 2.42 min

Example 154

(2S)-N-(2-Aminoethyl)-2-((3S)-3-{[(6-chloro-2-naphthyl)sulfonyl]amino}-2-oxopyrrolidin-1-yl)propanamide hydrochloride Example 152 (0.281 g) was dissolved in DCM (3 ml), and 4M HCl in dioxane (3 ml) was added. The mixture was stirred at room temperature for 18 h and then concentrated under reduced pressure to give the title compound (0.247 g) as a white solid.

Mass spectrum: Found: $MH^+$ 439. H.p.l.c. (1) Rt 2.35 min

Example 155

(2S)-2-((3S)-{(2-Amino-2-oxoethyl)-3-({[(E)-2-(5-chlorothien-2-yl)ethenyl]sulfonyl}amino)-2-oxopyrrolidin-1-yl)-N-ethyl-N-isopropylpropanamide Using Example 150, and the synthetic procedure described for Intermediate 6, the title compound was prepared.

Mass spectrum: Found: $MH^+$ 505. H.p.l.c. (1) Rt 2.92 min

Using similar chemistry and Example 149, the following was prepared:

Example 156

(2S)-2-((3S)-{(2-Amino-2-oxoethyl)-3-({[(6-chloro-1-benzothien-2-yl)sulfonyl]amino)-2-oxopyrrolidin-1-yl)-N-ethyl-N-isopropylpropanamide Mass spectrum: Found: $MH^+$ 529. H.p.l.c. (1) Rt 3.09 min

Intermediate 1 tert-Butyl N-[(benzyloxy)carbonyl]-L-methionyl-D-alaninate

Z-Protected L-methionine (10 g) was dissolved in DMF (200 ml) and 1-[3-(diemthylamino)propyl]-3-ethylcarbodi imide hydrochloride (8.13 g) was added followed by HOBT (5.72 g) and triethylamine (19.7 ml). The mixture was stirred for 1 h then L-alanine tert-butyl ester (7.7 g) was added and stirring continued for 18 h. The mixture was evaporated under reduced pressure and partitioned between diethyl ether and water. The separated organic phase was washed with hydrochloric acid (1M), saturated sodium bicarbonate solution and brine, dried (over magnesium sulphate) and concentrated under reduced pressure to give the title compound (11.9 g) as an orange oil which crystallised on standing.

Mass spectrum: Found: MH+ 411.

Intermediate 2 tert-Butyl (2S)-2-((3S)-3-{[(benzyloxy)carbonyl]amino}-2-oxopyrrolidin-1-yl)propanoate A solution of tert-butyl N-[(benzyloxy)carbonyl]-l-methionyl-D-alaninate (11.9 g) in acetone (75 ml) was treated with methyl iodide (18 ml) and stirred at room temperature for 72 h. The reaction mixture was then concentrated under reduced pressure to give an orange solid which was dissolved in acetonitrile (200 ml). Dowex (OH− form) resin (19.42 g) was added and the mixture stirred for 18 h at room temperature. The mixture was filtered and the resin washed with ethyl acetate. The filtrate was evaporated under reduced pressure to afford a yellow oil which was purified by Biotage™ chromatography (eluting with cyclohexane/ethyl acetate 3:2) to give the title compound (2.92 g) as a colourless oil.

Mass spectrum: Found: MH+ 363.

Intermediate 3 tert-Butyl (2S)-2-[(3S)-3-amino-2-oxopyrrolidin-1-yl]propanoate

A mixture of tert-butyl (2S)-2-((3S)-3-{[(benzyloxy)carbonyl]amino}-2-oxopyrrolidin-1-yl)propanoate (2.82 g), 10% palladium on carbon (0.300 g) and ethanol (150 ml) was stirred under an atmosphere of hydrogen for 18 h. The reaction mixture was filtered through Harbolite™ and the filtrate was concentrated under reduced pressure to give the title compound (1.8 g) as a pale yellow oil.

$^1$H NMR (D$_4$MeOD): δ4.56(1H, q), 3.57(1H, dd), 3.49–3.35(2H, 2×m), 2.48–2.39(1H, m), 1.88–1.77(1H, m), 1.47(9H, s), 1.40 (3H, d) ppm.

Intermediate 4 tert-Butyl (2S)-2-((3S)-3-{[(6-chloro-2-naphthyl)sulfonyl]amino}-2-oxopyrrolidin-1-yl)propanoate A solution of tert-butyl (2S)-2-[(3S)-3-amino-2-oxopyrrolidin-1-yl]propanoate (1.8 g) in DCM (75 ml) was treated with 6-chloronaphthylsulphonyl chloride[1] (2.28 g) and pyridine (0.705 ml) and stirred at room temperature for 72 h. The mixture was washed with water and concentrated under reduced pressure to yield an oil which was purified by Biotage™ chromatography (eluting with cyclohexane/ethyl acetate 3:1) to give the title compound (2.31), as a white solid.

Mass spectrum: Found: MH+ 453.

Intermediate 5

(2S)-2-((3S)-3-{[(6-Chloro-2-naphthyl)sulfonyl]amino}-2-oxopyrrolidin-1-yl)propanoic acid tert-Butyl (2S)-2-((3S)-3-{[(6-chloro-2-naphthyl)sulfonyl]amino}-2-oxopyrrolidin-1-yl)propanoate (0.643 g) was dissolved in DCM (19 ml), and trifluoroacetic acid (19 ml) was added. The mixture was stirred at room temperature for 2.5 h and then concentrated under reduced pressure. Anhydrous DCM (4 ml) was added and the solution evaporated under reduced pressure. Repetitive addition of DCM and concentration under reduced pressure provided the title compound (0.56 g) as a white foam.

Mass spectrum: Found: MH+ 397.

Intermediate 6 tert-Butyl (2S)-2-((3S)-3-{(2-amino-2-oxoethyl)[(6-chloro-2-naphthyl)sulfonyl]amino}-2-oxopyrrolidin-1-yl)propanoate A solution of tert-butyl (2S)-2-((3S)-3-{[(6-chloro-2-naphthyl)sulfonyl]amino}-2-oxopyrrolidin-1-yl)propanoate (1.31 g) in DMF (22 ml) was treated with potassium carbonate (0.786 g) followed by 2-bromoacetamide (0.48 g) and the resultant mixture stirred at room temperature for 22 h. Additional 2-bromoacetamide (0.4 g) and potassium carbonate (0.4 g) were added and the mixture was stirred at room temperature for 24 h. The reaction mixture was evaporated under reduced pressure and the residue partitioned between ethyl acetate and water. The separated organic layer was washed with water, dried (over magnesium sulphate) and evaporated under reduced pressure to give the title compound (1.4 g) as a white foam.

Mass spectrum: Found: MH+ 510.

Intermediate 7

(2S)-2-((3S)-3-{(2-Amino-2-oxoethyl)[(6-chloro-2-naphthyl)sulfonyl]amino}-2-oxopyrrolidin-1-yl)propanoic acid tert-Butyl (2S)-2-((3S)-3-{(2-amino-2-oxoethyl)[(6-chloro-2-naphthyl)sulfonyl]amino}-2-oxopyrrolidin-1-yl)propanoate (1.4 g) was dissolved in DCM (35 ml), and trifluoroacetic acid (35 ml) was added. The mixture was stirred at room temperature for 2 h and then evaporated under reduced pressure. The residue was azeotroped with anhydrous dichloromethane and then dried under high vacuum. The residual viscous oil was triturated with diethyl ether to give the title compound (1.23 g) as a white solid.

Mass spectrum: Found: MH+ 454.

Intermediate 8 tert-Butyl 2-(isopropylamino)ethylcarbamate

N-Isopropylethylene diamine (1.25 ml) was dissolved in dry DCM (50 ml), cooled to 0° C. and treated with di-tert-butyl dicarbonate (1.09 g) and triethylamine (1.39 ml). The resultant mixture was stirred at room temperature for 90 min and then evaporated under reduced pressure. The residue was purified using SPE (silica, eluting with DCM:MeOH:aqueous NH$_3$, 100:8:1) to give the title compound (0.85 g) as a pale yellow oil.

T.l.c. (DCM:MeOH:aqueous NH$_3$, 200:5:2) R$_f$ 0.2

Using similar chemistry, the following was prepared:

Intermediate 9 tert-Butyl 3-(isopropylamino)propylcarbamate

T.l.c. (DCM:MeOH:aqueous $NH_3$, 200:5:2) $R_f$ 0.25

Intermediate 10 tert-Butyl 2-[[(2S)-2-((3S)-3-{[(6-chloro-2-naph-thyl)sulfonyl]amino}-2-oxopyrrolidin-1-yl)pro-panoyl](isopronyl)amino]ethylcarbamate To a solution of (2S)-2-((3S)-3-{[(6-chloro-2-naphthyl)sulfonyl]amino}-2-oxopyrrolidin-1-yl)propanoic acid (0.198 g) in DMF (10 ml) were added 2-(1H-benzotriazole-1-yl)-1,1,3,3-tetramethyluronium tetrafluoroborate (0.321 g) and diisopropylethylamine (0.174 ml) and the mixture was stirred at room temperature for 30 min. tert-Butyl 2-(isopropylamino)ethylcarbamate (0.202 g) was added and the resultant mixture stirred at room temperature for 72 h. The mixture was concentrated under reduced pressure and the residue was partitioned between DCM and saturated sodium bicarbonate. The organic layer was separated, dried (over magnesium sulphate), filtered and concentrated under reduced pressure to give an oil which was purified using SPE (silica, eluting with cyclohexane:ethyl acetate, 20:1 to 1:2) to give the title compound (0.210 g) as a colourless gum.

Mass spectrum: Found: $MH^+$ 581.

Intermediate 11

3-(Cyclopropylmethyl-amino)-propionitrile

With stirring and cooling in an ice-bath to maintain a temperature of 8–10° C., acrylonitrile (0.614 ml) was added to aminomethylcyclopropane (0.651 g). The resultant mixture was stirred at room temperature for 15 h to give the title compound (1.02 g) as a yellow oil.

Mass spectrum: Found: $MH^+$ 125.

Intermediate 12

N-(pyridin-4-ylmethyl)propan-2-amine

4-Bromomethylpyridine (1 g) was suspended in THF:ethanol (5:1) and cooled to 0–5° C. Isopropylamine (1.01 ml) was added and the resultant mixture allowed to reach room temperature. After 24 h, the mixture was concentrated under reduced pressure and the residue purified using SPE (silica, eluting with DCM:methanol 1:1, 3:7, 1:4 and methanol) to give an impure sample of the title compound. Further purification using SPE (silica, eluting with DCM, ethyl acetate, acetonitrile, methanol) gave the title compound (0.25 g) as a white solid.

Mass spectrum: Found: $MH^+$ 151.

Intermediate 13

Hexamethyleneimineacetonitrile

To a solution of chloroacetonitrile (73 g) in benzene (500 ml) was added anhydrous sodium carbonate (52 g) followed by a solution of hexamethyleneimine (96 g) in benzene (250 ml). The mixture was stirred and heated under reflux for 4 h, cooled in an ice-bath and filtered. The filtrate was concentrated under reduced pressure and the residue purified by distillation to give the title compound (117 g) as an oil.

B.p. 108–112° C., 17 mm Hg

Intermediate 14

1-Amino-2-hexamethyleneiminoethane

A solution of hexamethyleneimineacetonitrile (60 g) in dry diethyl ether (200 ml) was slowly added to a stirred suspension of lithium aluminium hydride (16.5 g) in dry diethyl ether (200 ml) at a rate to maintain a steady reflux. Addition was completed in 1.5 h, and then the mixture was stirred at room temperature for 1 h. The reaction mixture was cooled in an ice-bath and treated with methanol (10 ml), sodium hydroxide solution (10N, 10 ml) and water (40 ml), and left to stand at room temperature for 18 h. The organic layer was separated, and stirred with potassium hydroxide pellets, filtered and concentrated under reduced pressure. The residue was purified by distillation to give the title compound (44.4 g) as an oil.

B.p. 86–90° C., 17 mm Hg

Intermediate 15

N-(2-Hexamethyleneiminoethyl)-N-isopronylamine

A mixture of 1-amino-2-hexamethyleneiminoethane (14.2 g), acetone (7 g) and platinium oxide (0.4 g) in ethanol (50 ml) was hydrogenated at room temperature and pressure for 24 h. The solution was filtered over Celite™ and the filtrate concentrated under reduced pressure. The residue was distilled to give the title compound (13.85 g) as an oil B.p. 102–106° C., 17 mm Hg

Intermediate 16

N-(1H-pyrazol-3-ylmethyl)propan-2-amine

To a mixture of pyrazolyl-3-carboxaldehyde (0.06 g), isopropylamine (0.081 ml) and acetic acid (0.072 ml) in dry DCM (4 ml), sodium triacetoxyborohydride (0.2 g) was added at 0° C. and the resultant solution sturred at room temperature for 72 h. Sodium hydroxide solution (2M) was added and the solution was extracted with DCM. The combined organic extracts were filtered through a hydrophobic frit and the filtrate concentrated under reduced pressure. The residue was purified using SPE (silica, eluting with methanol and methanol: 10% aqueous ammonia) to give the title compound (0.074 g) as a gum.

GCMS: $MH^+$ 151

Using similar chemistry, the following was prepared;

Intermediate 17

N-(pyridin-4-ylmethyl)prop-2-en-1-amine

GCMS: $MH^+$ 149

Intermediate 18 tert-Butyl 2-[(cyclopropylmethyl)amino]ethylcarbamate tert-Butyl N-(2-oxoethyl)carbamate (1 g) was dissolved in dry methanol (40 ml) and treated with cyclopropane methylamine (0.709 ml) and 4A° molecular sieves (1 g) and the resultant mixture stirred at room temperature for 5 h. Sodium borohydride (0.38 g) was added and the reaction stirred for a further 18 h at room temperature. Sodium hydroxide (2N, 3 ml) was added, the mixture filtered and the filtrate concentrated under reduced pressure. The residue was partitioned between sodium hydroxide solution (2N) and ethyl acetate. The separated organic layer was dried (over magnesium sulphate), filtered and concentrated under reduced pressure to give the title compound (1 g) as a colourless oil
$^1$H NMR (CDCl$_3$): δ4.95(1H, br.s), 3.23(2H, dt), 2.75(2H, t), 2.47(2H, d), 1.45(9H, s), 0.95(1H, m), 0.47(2H, m), 0.12(2H, m) ppm.

Intermediate 19

2-{[tert-Butyl(dimethyl)silyl]oxy}-N-(cyclopropyl-methyl)ethanamine (tert-Butyldimethylsilyloxy)acetaldehyde (0.98 g) was dissolved in dry methanol (40 ml) and then treated with cyclopropane methylamine (0.634 ml) followed by 4A° molecular sieves (1 g). The resultant mixture was stirred for 5 h at room temperature and then sodium borohydride (0.340 g) was added. After stirring for a further 18 h at room temperature, sodium hydroxide (2N) was added, the mixture was filtered and the filtrate concentrated under reduced pressure. The residue was partitioned between sodium hydroxide (2N) and ethyl acetate. The separated aqueous layer was washed further with ethyl acetate. The combined organic components were dried (over magnesium sulphate), filtered and concentrated under reduced pressure to give the title compound (0.78 g) as a yellow oil.
$^1$H NMR (CDCl$_3$): δ3.70(2H, t), 2.70(2H, t), 2.75(2H, t), 2.47(2H, d), 0.95(1H, m), 0.88(9H, s), 0.47(2H, m), 0.10 (2H, m), 0.05(6H, s) ppm.

Intermediate 20

(2S)-N-(2-{[tert-Butyl(dimethyl)silyl]oxy}ethyl)-2-((3S)-3-{[(6-chloro-2-naphthyl)sulfonyl]amino}-2-oxopyrrolidin-1-yl)-N-(cyclopropylmethyl)propanamide Using Intermediates 5 and 19, and similar chemistry to that described for the preparation of Example 1, the title compound was prepared.
Mass spectrum: Found: MH$^+$ 609.

Intermediate 21 tert-Butyl [[(2S)-2-((3S)-3-{[(6-chloro-2-naphthyl)sulfonyl]amino}-2-oxopyrrolidin-1-yl)propanoyl] (isopropyl)amino]acetate Using tert-butyl (isopropylamino)acetate and Intermediate 5, and similar chemistry to that described for the preparation of Example 1, the title compound was prepared.
Mass spectrum: Found: MH$^+$ 553.

Intermediate 22

2-tert-Butoxy-N-(pyridin-4-ylmethyl)ethanamine

Using 4-pyridine carboxaldehyde and O-tert butyl ethanolamine, and the synthetic procedure described for Intermediate 16, a crude sample of the title compound was prepared, which was used directly in the next stage of the synthetic sequence.

Intermediate 23

(2S)-2-((3S)-3-{[(Benzyloxy)carbonyl]amino}-2-oxopyrrolidin-1-yl)propanoic acid

Using Intermediate 2 and the procedure described for Intermediate 5, the title compound was prepared.
Mass spectrum: Found: MH$^+$ 307.

Intermediate 24

Benzyl (3S)-1-{(1S)-2-[ethyl(isopropyl)amino]-1-methyl-2-oxoethyl}-2-oxopyrrolidin-3-ylcarbamate Using the Intermediate 23 and ethylisopropylamine, and similar chemistry to that described for the preparation of Example 1, the title compound was prepared.
Mass spectrum: Found: MH$^+$ 376.

Intermediate 25

(2S)-2-[(3S)-3-Amino-2-oxopyrrolidin-1-yl]-N-ethyl-N-isopropylpropanamide

Using Intermediate 24 and the synthetic procedure described for Intermediate 3, the title compound was prepared.
Mass spectrum: Found: MH$^+$ 242.

Intermediate 26

[[(2S)-2-((3S)-3-{[(6-Chloro-2-naphthyl)sulfonyl] amino}-2-oxopyrrolidin-1-yl)propanoyl](isopropyl) amino]acetic acid Using Intermediate 21, and the chemistry described to prepare Example 131, the title compound was prepared:
Mass spectrum: Found: MH$^+$ 496.

REFERENCES

1. Klimkowski, Valentine Joseph; Kyle, Jeffrey Alan; Masters, John Joseph; Wiley, Michael Robert. PCT Int. Appl. (2000), WO 0039092.

In Vitro Assay for Inhibition of Factor Xa (1)

Compounds of the present invention (Examples 1–147) were tested for their Factor Xa inhibitory activity as determined in vitro by their ability to inhibit human Factor Xa in a chromogenic assay, using N-α-benzyloxycarbonyl-D-Arg-Gly-Arg-p-nitroanilide as the chromogenic substrate. Compounds were diluted from a 10 mM stock solution in dimethylsulfoxide at appropriate concentrations. Assay was performed at room temperature using buffer consisting of: 50 mM Tris-HCl, 150 mM NaCl, 5 mM CaCl$_2$, pH 7.4. containing human Factor Xa (final conc. Of 0.0015 U.ml$^{-1}$). Compound and enzyme were preincubated for 15 min prior to addition of the substrate (final conc. of 200 μM). The reaction was stopped after 30 min with the addition of soybean trypsin inhibitor or H-D-PHE-PRO-ARG-Chloromethylketone. BioTek EL340 or Tecan SpectraFluor Plus plate readers were used to monitor the absorbance at 405 nm. To obtain IC$_{50}$ values the data were analysed using ActivityBase® and XLfit®.

Calculation of Ki values:

$$Ki=IC_{50}/(1+[Substrate]/Km)$$

The Ki value for the above assay can be obtained by dividing the $IC_{50}$ value by 7.

In Vitro Assay for Inhibition of Factor Xa (2)

Compounds of the present invention (Examples 148–156) were tested for their Factor Xa inhibitory activity as determined in vitro by their ability to inhibit human Factor Xa in a fluorogenic assay, using Rhodamine 110, bis-(CBZ-glycylglycyl-L-arginine amide as the fluorogenic substrate. Compounds were diluted from a 10 mM stock solution in dimethylsulfoxide at appropriate concentrations. Assay was performed at room temperature using buffer consisting of: 50 mM Tris-HCl, 150 mM NaCl, 5 mM $CaCl_2$, pH 7.4. containing human Factor Xa (final conc. Of 0.0003 U.ml–1). Compound and enzyme were preincubated for 15 min prior to addition of the substrate (final conc. of 10 μM). The reaction was stopped after 3 hrs with the addition of H-D-PHE-PRO-ARG-Chloromethylketone. An LJL-Analyst fluorimeter was used to monitor fluorescence with 485 nm excitation/535 nm emission. To obtain $IC_{50}$ values the data were analysed using ActivityBase® and XLfit®.

Calculation of Ki values:

$$Ki=IC_{50}/(1+[Substrate]/Km)$$

The Ki value for the above assay can be obtained by dividing the $IC_{50}$ value by 1.6.

All of the synthetic Example compounds tested (Examples 1–156) by one of the above described in vitro assays for Factor Xa exhibited $IC_{50}$ values of less than 4 μM.

Preferably compounds have a Ki value of less than 1 μM, more preferably compounds have an Ki value of less than 200 nM, most preferably compounds have a Ki value of less than 20 nM.

Method for Measurement of Prothrombin Time (PT)

Blood is collected into a sodium citrate solution (ratio 9:1) to give a final concentration of 0.38% citrate. Plasma is generated by centrifugation of citrated blood samples at 1200×g for 20 min at 4° C.

The PT test is performed at 37° C. in plastic cuvettes containing a magnetic ball bearing. 50 μL of citrated plasma and either 25 μL of 2.8% DMSO for control or 25 μL of test compound (dissolved in DMSO and diluted in water and 2.8% DMSO to give 0.4% DMSO final in assay) at a concentration of 7-times the final desired concentration is pippetted into each cuvette. This mixture is incubated for 1 mm at 37° C. before adding 100 μL of thromboplastin mixture (comprising lyophilised rabbit thromboplastin and calcium chloride which is reconstituted in distilled water as per manufacturer's [Sigma] instructions). On addition of the thromboplastin mixture, the timer is automatically started and continued until the plasma clotted. The time to clotting was recorded (normal range for human plasma is 10–13seconds).

Method for Measurement of Prothrombin Time (PT)-Test 2

Blood is collected into a sodium citrate solution (ratio 9:1) to give a final concentration of 0.38% citrate. Plasma is generated by centrifugation of citrated blood samples at 1200×g for 20 min at 4° C.

The PT test is preformed at 37° C. in plastic cassettes and using a MCA210 Microsample Coagulation Analyzer (Bio/Data Corporation). For assay, 25 ul of plasma containing test compound at concentrations ranging from 0.1 to 100 uM (made from a 1 mM stock solution in 10% DMSO and plasma) and 25 ul of Thromboplastin C Plus (Dade Berhing) are automatically injected into the cassette. Upon addition of the Thromboplastin C Plus, the instrument determines and records the time to clot (normal range for human plasma is 10–13seconds).

General Purification and Analytical Methods

LC/MS Method (1)

Analytical HPI,C was conducted on a Supelcosil LCABZ+PLUS column (3 μm, 3.3 cm×4.6 mm ID) eluting with 0.1% $HCO_2H$ and 0.01 M ammonium acetate in water (solvent A), and 95% acetonitrile and 0.05% $HCO_2H$ in water (solvent B), using the following elution gradient 0–0.7 minutes 0% B, 0.7–4.2 minutes 0→100% B, 4.2–5.3 minutes 100% B, 5.3–5.5 minutes 100→0% B at a flow rate of 3 ml/minutes (System 1). The mass spectra (MS) were recorded on a Fisons VG Platform mass spectrometer using electrospray positive ionisation [(ES+ve to give $MH^+$ and $M(NH_4)^+$ molecular ions] or electrospray negative ionisation [(ES–ve to give $(M-H)^-$ molecular ion] modes.

LC/MS Method (2)

Method 2 was conducted on a Waters Xtera $RP_{18}$ column (3 μm, 15 cm×2.1 mm ID) eluting with solvent A (0.1% $HCO_2H$ and water) and solvent B (100% acetonitrile, 0.1% $HCO_2H$ and reserpine 2.5 $\mu gml^{-1}$) at 20° C. The following elution gradient was ran: 0–2.0 minutes 0% B; 2.0–18.0 minutes 0–100% B; 18.0–20.0 minutes 100% B; 20.0–22.0 minutes 100–0% B; 22.0–30.0 minutes 0% B, at a flow rate of 0.4 ml/minutes. The mass spectra (MS) were recorded on a Micromass QTOF 2spectrometer using electrospray positive ionisation [$ES^+$ve to give $MH^+$].

Note: The number given in brackets in the Examples and Intermediates above, c.g. H.p.l.c. (1), specifies the LCIMS method used.

$^1$H mr spectra were recorded using a Bruker DPX 400 MHz spectrometer using tetramethylsilane as the external standard.

Biotage™ chromatography refers to purification carried out using equipment sold by Dyax Corporation (either the Flash 40i or Flash 150i) and cartridges pre-packed with KPSil.

Mass directed autoprep refers to methods where the material was purified by high performance liquid chromatography on a HPLCABZ+5 μm column (5 cm×10 mm i.d.) with 0.1% $HCO_2H$ in water and 95% MECN, 5% water (0.5% $HCO_2H$) utilising the following gradient elution conditions: 0–1.0 minutes 5% B, 1.0–8.0 minutes 5→30% B, 8.0–8.9 minutes 30% B, 8.9–9.0 minutes 30→95%B, 9.0–9.9 minutes 95% B, 9.9–10 minutes 95→0% B at a flow rate of 8 ml $minutes^{-1}$ (System 2). The Gilson 202-fraction collector was triggered by a VG Platform Mass Spectrometer on detecting the mass of interest.

Hydrpophobic frits refers to filtration tubes sold by Whatman.

SPE (solid phase extraction) refers to the use of cartridges sold by International Sorbent Technology Ltd.

TLC (thin layer chromatography) refers to the use of TLC plates sold by Merck coated with silica gel 60 $F_{254}$.

The invention claimed is:

1. A compound of formula (I)

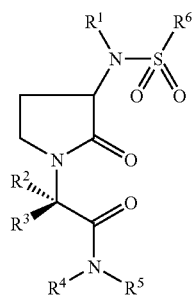

wherein:
$R^1$ represents hydrogen or —$C_{1-3}$alkylCONR$^a$R$^b$;
One of $R^2$ and $R^3$ represents —$C_{1-3}$alkyl and the other represents hydrogen;
$R^4$ represents hydrogen, —$C_{1-4}$alkyl, —$C_{3-4}$alkenyl, —$C_{2-4}$alkylOH, —$C_{2-4}$alkylOC$_{1-4}$alkyl, —$C_{1-4}$alkylCN or —$C_{0-4}$alkylC$_{3-6}$cycloalkyl;
$R^5$ represents —$C_{2-4}$alkylOH, —$C_{1-4}$alkyl, —$C_{2-4}$alkylOC$_{1-4}$alkyl, —$C_{1-4}$alkylCN, —$C_{2-4}$alkylNR$^a$R$^b$, —$C_{2-4}$ alkylNHCOC$_{1-3}$alkyl, —$C_{2-4}$alkylNHCONR$^a$R$^b$, —$C_{2-4}$alkylNHSO$_2$R$^e$, —$C_{2-4}$alkylSO$_2$NR$^a$R$^b$, —$C_{2-4}$alkylNHCO$_2$C$_{1-4}$alkyl, —$C_{2-4}$alkylNHC(NH$_2$)=NR$^f$, or a group X—Y;
X represents —$C_{1-4}$alkylene- optionally substitued by —OH, or a direct link, with the proviso that when X is substituted by —OH, X represents $C_{2-4}$alkylene and the —OH group is not alpha with respect to the amide N atom to which the group X is attached;
Y represents —$C_{3-6}$cycloalkyl, phenyl, or an aromatic or non-aromatic 5-, 6- or 7-membered heterocyclic group containing at least one heteroatom selected from O, N or S and optionally substituted at C and/or N atoms by —$C_{1-3}$alkyl, $C_{1-3}$alkoxy, $C_{1-3}$alkylOH, halogen, —CN, —CF$_3$, —NH$_2$, —CO$_2$H and —OH;
$R^a$ and $R^b$ independently represent hydrogen or —$C_{1-4}$alkyl;
$R^e$ represents —$C_{1-4}$alkyl or —CF$_3$;
$R^f$ represents NO$_2$ or CN;
$R^6$ represents a group selected from:

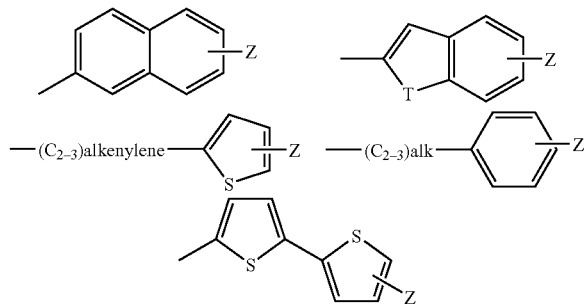

Z represents an optional substituent halogen,
alk represents alkylene or alkenylene,
T represents a heteroatom selected from S or N;

or a pharmaceutically acceptable derivative thereof.

2. A compound of formula (I) as claimed in claim 1 wherein:
$R^1$ represents hydrogen or —$C_{1-3}$alkylCONR$^a$R$^b$;
One of $R^2$ and $R^3$ represents —$C_{1-3}$alkyl and the other represents hydrogen;
$R^4$ represents —$C_{1-4}$alkyl, —$C_{2-4}$alkylOH, —$C_{1-4}$alkylCN, —$C_{3-6}$cycloalkyl;
$R^5$ represents —$C_{2-4}$alkylOH, —$C_{1-4}$alkyl, —$C_{2-4}$alkylOC$_{1-3}$alkyl, —$C_{1-4}$alkylCN, —$C_{2-4}$alkylNR$^a$R$^b$, —$C_{2-4}$ alkylNHCOC$_{1-3}$alkyl, —$C_{2-4}$alkylNHCONR$^a$R$^b$, —$C_{2-4}$alkylNHSO$_2$R$^a$, —$C_{1-4}$alkylSO$_2$NR$^a$R$^b$, or a group X—Y;
X represents —$C_{1-4}$alkylene- or a direct link;
Y represents —$C_{3-6}$cycloalkyl, phenyl, or an aromatic or non-aromatic 5-, 6- or 7-membered heterocyclic group containing one or two O, N or S atoms and optionally substituted at C and/or N atoms by —$C_{1-3}$alkyl;
$R^a$ and $R^b$ independently represent hydrogen or —$C_{1-3}$alkyl;
$R^6$ represents a group selected from:

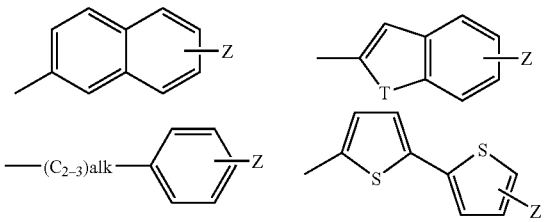

Z represents an optional substituent halogen,
alk represents alkylene or alkenylene,
T represents a heteroatom selected from S or N;
or a pharmaceutically acceptable salt or solvate thereof.

3. A compound as claimed in claim 1 wherein $R^1$ represents hydrogen or —CH$_2$CONH$_2$.

4. A compound as claimed in claim 1 wherein one of $R^2$ and $R^3$ represents methyl and the other represents hydrogen.

5. A compound as claimed in claim 1 wherein $R^4$ represents —$C_{1-4}$alkyl, —$C_{3-4}$alkenyl, —$C_{2-4}$alkylOH, —$C_{2-4}$alkylOC$_{1-4}$alkyl, —$C_{1-4}$alkylCN or —$C_{0-4}$alkylC$_{3-6}$cycloalkyl.

6. A compound as claimed in claim 1 wherein $R^5$ represents —$C_{2-4}$alkylOH, —$C_{1-4}$alkyl, —$C_{2-4}$alkylOC$_{1-4}$alkyl, —$C_{1-4}$alkylCN, —$C_{2-4}$alkylNR$^a$R$^b$, —$C_{2-4}$alkylNHCO C$_{1-3}$alkyl, —$C_{2-4}$alkylNHCONR$^a$R$^b$, —$C_{2-4}$alkylNHSO$_2$R$^e$, —$C_{2-4}$alkylSO$_2$NR$^a$R$^b$, —$C_{2-4}$alkylNHCO$_2$C$_{1-4}$alkyl, —$C_{2-4}$alkylNHC(NH$_2$)=NR$^f$, or a group X—Y.
X represents —$C_{1-3}$alkylene- optionally substituted by —OH, or a direct link, with the proviso that when X is substituted by —OH, X represents $C_{2-4}$alkylene and the —OH group is not alpha with respect to the amide N atom to which the group X is attached;
Y represents phenyl, or an aromatic or non-aromatic 5-, 6- or 7-membered heterocyclic group containing one or two heteroatoms selected from O, N or S atoms and optionally substituted at C and/or N atoms by —$C_{1-3}$alkyl.

7. A compound as claimed in claim 6 wherein $R^5$ represents —$C_{2-4}$alkylOH, —$C_{1-4}$alkyl, —$C_{2-4}$alkylOC$_{1-3}$alkyl, —$C_{1-4}$alkylCN, —$C_{2-4}$alkylNR$^a$R$^b$, —$C_{2-4}$alkylNHCOC$_{1-3}$alkyl, —$C_{2-4}$alkylNHCONR$^a$R$^b$, $C_{2-4}$alkylNHSO$_2$R$^e$, —C$_{2-4}$ alkylSO$_2$NR$^a$R$^b$, —C$_{2-4}$alkylNHCO$_2$C$_{1-4}$alkyl, —C$_{2-4}$alkylNHC(NH$_2$)=NR$^f$, or a group X—Y;

X represents —C$_{1-3}$alkylene-;

Y represents phenyl, or an aromatic or non-aromatic 5-, 6- or 7-membered heterocyclic group containing one or two heteroatoms selected from O, N or S atoms and optionally substituted at C and/or N atoms by —C$_{1-3}$alkyl.

8. A compound as claimed in claim 1 wherein R$^6$ represents a group selected from: chloronaphthylene, chlorobenzothiophene, chlorobithiophene, chlorophenylethene or (chlorothienyl)ethene.

9. A compound selected from:

(2S)-2-((3S)-3-{[(6-Chloro-2-naphthyl)sulfonyl]amino}-2-oxopyrrolidin-1-yl)-N-ethyl-N-isopropylpropanamide;

(2S)-2-((3S)-3-{[(6-chloro-2-naphthyl)sulfonyl]amino}-2-oxopyrrolidin-1-yl)-N-isopropyl-N-(pyridin-4-ylmethyl)propanamide;

(2S)-2-((3S)-3-{[(6-Chloro-2-naphthyl)sulfonyl]amino}-2-oxopyrrolidin-1-yl)-N-isopropyl-N-(pyridin-3-ylmethyl)propanamide;

(2S)-N-(2-Azepan-1-ylethyl)-2-((3S)-3-{[(6-chloro-2-naphthyl)sulfonyl]amino}-2-oxopyrrolidin-1-yl)-N-isopropylpropanamide formate;

(2S)-2-((3S)-3-{[(6-Chloro-2-naphthyl)sulfonyl]amino}-2-oxopyrrolidin-1-yl)-N-(2-cyanoethyl)-N-isopropylpropanamide;

(2S)-2-((3S)-3-{[(6-Chloro-2-naphthyl)sulfonyl]amino}-2-oxopyrrolidin-1-yl)-N-(2-hydroxyethyl)-N-isopropylpropanamide;

(2S)-2-((3S)-3-{[(6-Chloro-2-naphthyl)sulfonyl]amino}-2-oxopyrrolidin-1-yl)-N-(2-cyanoethyl)-N-(cyclopropylmethyl)propanamide;

(2S)-2-((3S)-3-{[(6-Chloro-2-naphthyl)sulfonyl]amino}-2-oxopyrrolidin-1-yl)-N-[2-(dimethylamino)ethyl]-N-ethylpropanamide formate;

(2S)-2-((3S)-3-{[(6-Chloro-2-naphthyl)sulfonyl]amino}-2-oxopyrrolidin-1-yl)-N-isopropyl-N-(pyridin-2-ylmethyl)propanamide;

(2S)-2-((3S)-3-{[(6-Chloro-2-naphthyl)sulfonyl]amino}-2-oxopyrrolidin-1-yl)-N-ethyl-N-(2-piperidin-1-ylethyl)propanamide formate;

(2S)-2-((3S)-3-{[(6-Chloro-2-naphthyl)sulfonyl]amino}-2-oxopyrrolidin-1-yl)-N-isopropyl-N-(2-pyridin-2-ylethyl)propanamide;

(2S)-2-((3S)-3-{[(6-Chloro-2-naphthyl)sulfonyl]amino}-2-oxopyrrolidin-1-yl)-N-(2-hydroxypropyl)-N-isopropylpropanamide;

(2S)-2-((3S)-3-{[(6-Chloro-2-naphthyl)sulfonyl]amino}-2-oxopyrrolidin-1-yl)-N-(cyanomethyl)-N-isopropylpropanamide formate;

(2S)-2-((3S)-3-{[(6-Chloro-2-naphthyl)sulfonyl]amino}-2-oxopyrrolidin-1-yl)-N-isopropyl-N-(3-methoxypropyl)propanamide;

(2S)-2-((3S)-3-{[(6-Chloro-2-naphthyl)sulfonyl]amino}-2-oxopyrrolidin-1-yl)-N-isopropyl-N-(2-methoxyethyl)propanamide;

(2S)-N-[2-(Acetylamino)ethyl]-2-((3S)-3-{[(6-chloro-2-naphthyl)sulfonyl]amino}-2-oxopyrrolidin-1-yl)-N-isopropylpropanamide;

(2S)-2-((3S)-3-{[(6-Chloro-2-naphthyl)sulfonyl]amino}-2-oxopyrrolidin-1-yl)-N-isopropyl-N-(thien-2-ylmethyl)propanamide;

(2S)-2-((3S)-3-{[(6-Chloro-2-naphthyl)sulfonyl]amino}-2-oxopyrrolidin-1-yl)-N-(3-hydroxypropyl)-N-isopropylpropanamide;

(2S)-2-((3S)-3-{[(6-Chloro-2-naphthyl)sulfonyl]amino}-2-oxopyrrolidin-1-yl)-N-(2-hydroxyethyl)-N-isopropylpropanamide;

(2S)-2-((3S)-3-{[(6-Chloro-2-naphthyl)sulfonyl]amino}-2-oxopyrrolidin-1-yl)-N-(2-cyanoethyl)-N-(cyclopropylmethyl)propanamide;

(2S)-2-((3S)-3-{[(6-Chloro-2-naphthyl)sulfonyl]amino}-2-oxopyrrolidin-1-yl)-N-(2-cyanoethyl)-N-(2-pyridin-2-ylethyl)propanamide;

(2S)-2-((3S)-3-{(2-Amino-2-oxoethyl)[(6-chloro-2-naphthyl)sulfonyl]amino}-2-oxopyrrolidin-1-yl)-N-ethyl-N-(pyridin-4-ylmethyl)propanamide;

(2S)-2-((3S)-3-{(2-Amino-2-oxoethyl)[(6-chloro-2-naphthyl)sulfonyl]amino}-2-oxopyrrolidin-1-yl)-N-isopropyl-N-(pyridin-2-ylmethyl)propanamide;

(2S)-2-((3S)-3-{(2-Amino-2-oxoethyl)[(6-chloro-2-naphthyl)sulfonyl]amino}-2-oxopyrrolidin-1-yl)-N-methyl-N-(pyridin-4-ylmethyl)propanamide;

(2S)-2-((3S)-3-{(2-Amino-2-oxoethyl)[(6-chloro-2-naphthyl)sulfonyl]amino}-2-oxopyrrolidin-1-yl)-N-methyl-N-(2-pyridin-2-ylethyl)propanamide;

(2S)-2-((3S)-3-{(2-Amino-2-oxoethyl)[(6-chloro-2-naphthyl)sulfonyl]amino}-2-oxopyrrolidin-1-yl)-N,N-dimethylpropanamide;

(2S)-2-((3S)-3-{(2-Amino-2-oxoethyl)[(6-chloro-2-naphthyl)sulfonyl]amino}-2-oxopyrrolidin-1-yl)-N-(2-hydroxyethyl)-N-isopropylpropanamide;

(2S)-2-((3S)-3-{(2-Amino-2-oxoethyl)[(6-chloro-2-naphthyl)sulfonyl]amino}-2-oxopyrrolidin-1-yl)-N-ethyl-N-(3-hydroxypropyl)propanamide;

(2S)-2-((3S)-3-{(2-Amino-2-oxoethyl)[(6-chloro-2-naphthyl)sulfonyl]amino}-2-oxopyrrolidin-1-yl)-N-ethyl-N-(2-morpholin-4-ylethyl)propanamide formate;

(2S)-2-((3S)-3-{(2-Amino-2-oxoethyl)[(6-chloro-2-naphthyl)sulfonyl]amino}-2-oxopyrrolidin-1-yl)-N-[2-(dimethylamino)ethyl]-N-ethylpropanamide formate;

(2S)-2-((3S)-3-{(2-Amino-2-oxoethyl)[(6-chloro-2-naphthyl)sulfonyl]amino}-2-oxopyrrolidin-1-yl)-N-ethyl-N-(2-hydroxyethyl)propanamide;

(2S)-2-((3S)-3-{(2-Amino-2-oxoethyl)[(6-chloro-2-naphthyl)sulfonyl]amino}-2-oxopyrrolidin-1-yl)-N-(2-methoxyethyl)-N-methylpropanamide;

(2S)-2-((3S)-3-{(2-Amino-2-oxoethyl)[(6-chloro-2-naphthyl)sulfonyl]amino}-2-oxopyrrolidin-1-yl)-N-ethyl-N-(2-piperidin-1-ylethyl)propanamide formate;

(2S)-2-((3S)-3-{(2-Amino-2-oxoethyl)[(6-chloronaphth-2-yl)sulfonyl]amino}-2-oxopyrrolidin-1-yl)-N-ethyl-N-methylpropanamide;

(2S)-2-((3S)-3-{(2-Amino-2-oxoethyl)[(6-chloronaphth-2-yl)sulfonyl]amino}-2-oxopyrrolidin-1-yl)-N,N-diethylpropanamide;

(2S)-2-((3S)-3-{(2-Amino-2-oxoethyl)[(6-chloronaphth-2-yl)sulfonyl]amino}-2-oxopyrrolidin-1-yl)-N,N-dipropylpropanamide;

(2S)-2-((3S)-3-{(2-Amino-2-oxoethyl)[(6-chloronaphth-2-yl)sulfonyl]amino}-2-oxopyrrolidin-1-yl)-N-ethyl-N-isopropylpropanamide;

(2S)-2-((3S)-3-{(2-Amino-2-oxoethyl)[(6-chloronaphth-2-yl)sulfonyl]amino}-2-oxopyrrolidin-1-yl)-N-isopropyl-N-(pyrid-4-ylmethyl)propanamide;

(2S)-2-((3S)-3-{(2-Amino-2-oxoethyl)[(6-chloronaphth-2-yl)sulfonyl]amino}-2-oxopyrrolidin-1-yl)-N-(2-cyanoethyl)-N-isopropylpropanamide;

(2S)-2-((3S)-3-{(2-Amino-2-oxoethyl)[(6-chloronaphth-2-yl)sulfonyl]amino}-2-oxopyrrolidin-1-yl)-N-(2-azepan-1-ylethyl)-N-isopropylpropanamide formate;

(2S)-N-[2-(Acetylamino)ethyl]-2-((3S)-3-{(2-amino-2-oxoethyl)[(6-chloronaphth-2-yl)sulfonyl]amino}-2-oxopyrrolidin-1-yl)-N-isopropylpropanamide;

(2S)-2-((3S)-3-{[(6-Chloro-2-naphthyl)sulfonyl]amino}-2-oxopyrrolidin-1-yl)-N-(2-cyanoethyl)-N-cyclopentylpropanamide;

(2S)-2-((3S)-3-{(2-Amino-2-oxoethyl)[(6-chloro-2-naphthyl)sulfonyl]amino}-2-oxopyrrolidin-1-yl)-N-(2-cyanoethyl)-N-cyclopentylpropanamide;

(2S)-2-((3S)-3-{(2-Amino-2-oxoethyl)[(6-chloro-2-naphthyl)sulfonyl]amino}-2-oxopyrrolidin-1-yl)-N-(2-cyanoethyl)-N-cyclopropylpropanamide;

(2S)-2-((3S)-3-{[(6-Chloro-2-naphthyl)sulfonyl]amino}-2-oxopyrrolidin-1-yl)-N-(2-cyanoethyl)-N-cyclobutylpropanamide;

(2S)-2-((3S)-3-(2-Amino-2-oxoethyl)[(6-chloro-2-naphthyl)sulfonyl]amino}-2-oxopyrrolidin-1-yl)-N-cyclopropyl-N-(pyridin-4-ylmethyl)propanamide;

(2S)-N-[2-(Aminosulfonyl)ethyl]-2-((3S)-3-{[(6-chloro-2-naphthyl)sulfonyl]amino}-2-oxopyrrolidin-1-yl)-N-isopropylpropanamide;

(2S)-2-((3S)-3-{(2-Amino-2-oxoethyl)[(6-chloro-2-naphthyl)sulfonyl]amino}-2-oxopyrrolidin-1-yl)-N-isopropyl-N-(2-piperidin-1-ylethyl)propanamide;

(2S)-2-((3S)-3-{(2-Amino-2-oxoethyl)[(6-chloro-2-naphthyl)sulfonyl]amino}-2-oxopyrrolidin-1-yl)-N-isopropyl-N-(2-morpholin-4-ylethyl)propanamide;

(2S)-2-((3S)-3-{[(6-Chloro-2-naphthyl)sulfonyl]amino}-2-oxopyrrolidin-1-yl)-N-isopropyl-N-(2-piperidin-1-ylethyl)propanamide;

(2S)-2-((3S)-3-{[(6-Chloro-2-naphthyl)sulfonyl]amino}-2-oxopyrrolidin-1-yl)-N-isopropyl-N-(2-morpholin-4-ylethyl)propanamide;

(2S)-2-((3S)-3-{[(6-Chloro-2-naphthyl)sulfonyl]amino}-2-oxopyrrolidin-1-yl)-N-isopropyl-N-(1H-pyrazol-3-ylmethyl)propanamide;

(2S)-2-((3S)-3-{[(6-Chloro-2-naphthyl)sulfonyl]amino}-2-oxopyrrolidin-1-yl)-N-isopropyl-N-[3-(4-methylpiperazin-1-yl)propyl]propanamide formate;

tert-Butyl 2-[[(2S)-2-((3S)-3-{(2-amino-2-oxoethyl)[(6-chloro-2-naphthyl)sulfonyl]amino}-2-oxopyrrolidin-1-yl)propanoyl](isopropyl)amino]ethylcarbamate;

tert-Butyl 3-[[(2S)-2-((3S)-3-{[(6-chloro-2-naphthyl)sulfonyl]amino}-2-oxopyrrolidin-1-yl)propanoyl](isopropyl)amino]propylcarbamate;

tert-Butyl 2-[[(2S)-2-((3S)-3-{[(6-chloro-2-naphthyl)sulfonyl]amino}-2-oxopyrrolidin-1-yl)propanoyl](cyclopropylmethyl)amino]ethylcarbamate;

(2S)-N-(2-Aminoethyl)-2-((3S)-3-{(2-amino-2-oxoethyl)[(6-chloro-2-naphthyl)sulfonyl]amino}-2-oxopyrrolidin-1-yl)-N-isopropylpropanamide hydrochloride;

(2S)-N-(3-Aminopropyl)-2-((3S)-3-{[(6-chloro-2-naphthyl)sulfonyl]amino}-2-oxopyrrolidin-1-yl)-N-isopropylpropanamide hydrochloride;

(2S)-N-(2-Aminoethyl)-2-((3S)-3-{[(6-chloro-2-naphthyl)sulfonyl]amino}-2-oxopyrrolidin-1-yl)-N-(cyclopropylmethyl)propanamide hydrochloride;

(2S)-N-(2-Aminoethyl)-2-((3S)-3-{[(6-chloro-2-naphthyl)sulfonyl]amino}-2-oxopyrrolidin-1-yl)-N-isopropylpropanamide;

(2S)-2-((3S)-3-{[(6-Chloro-2-naphthyl)sulfonyl]amino}-2-oxopyrrolidin-1-yl)-N-isopropyl-N-{2-[(methylsulfonyl)amino]ethyl}propanamide;

(2S)-2-((3S)-3-{(2-Amino-2-oxoethyl)[(6-chloro-2-naphthyl)sulfonyl]amino}-2-oxopyrrolidin-1-yl)-N-isopropyl-N-{2-[(methylsulfonyl)amino]ethyl}propanamide;

(2S)-2-((3S)-3-{[(6-Chloro-2-naphthyl)sulfonyl]amino}-2-oxopyrrolidin-1-yl)-N-isopropyl-N-{3-[(methylsulfonyl)amino]propyl}propanamide;

(2S)-2-((3S)-3-{[(6-Chloro-2-naphthyl)sulfonyl]amino}-2-oxopyrrolidin-1-yl)-N-(cyclopropylmethyl)-N-{2-[(methylsulfonyl)amino]ethyl}propanamide;

(2S)-N-[2-({(E)-Amino[oxido(oxo)hydrazono]methyl}amino)ethyl]-2-((3S)-3-{[(6-chloro-2-naphthyl)sulfonyl]amino}-2-oxopyrrolidin-1-yl)-N-isopropylpropanamide;

(2S)-N-[2-({(E)-Amino[oxido(oxo)hydrazono]methyl}amino)ethyl]-2-((3S)-3-{(2-amino-2-oxoethyl)[(6-chloro-2-naphthyl)sulfonyl]amino}-2-oxopyrrolidin-1-yl)-N-isopropylpropanamide;

(2S)-N-[3-({(E)-Amino[oxido(oxo)hydrazono]methyl}amino)propyl]-2-((3S)-3-{[(6-chloro-2-naphthyl)sulfonyl]amino}-2-oxopyrrolidin-1-yl)-N-isopropylpropanamide;

(2S)-2-((3S)-3-{[(6-Chloro-2-naphthyl)sulfonyl]amino}-2-oxopyrrolidin-1-yl)-N-isopropyl-N-[2-(methylamino)ethyl]propanamide;

(2S)-2-((3S)-3-{[(6-Chloro-2-naphthyl)sulfonyl]amino}-2-oxopyrrolidin-1-yl)-N-[2-(dimethylamino)ethyl]-N-isopropylpropanamide;

(2S)-N-{2-[(Aminocarbonyl)amino]ethyl}-2-((3S)-3-{[(6-chloro-2-naphthyl)sulfonyl]amino}-2-oxopyrrolidin-1-yl)-N-isopropylpropanamide;

(2S)-N-{2-[(Aminocarbonyl)amino]ethyl}-2-((3S)-3-{(2-amino-2-oxoethyl)[(6-chloro-2-naphthyl)sulfonyl]amino}-2-oxopyrrolidin-1-yl)-N-isopropylpropanamide;

(2S)-N-{2-[(Aminocarbonyl)amino]ethyl}-2-((3S)-3-{[(6-chloro-2-naphthyl)sulfonyl]amino}-2-oxopyrrolidin-1-yl)-N-(cyclopropylmethyl)propanamide;

(2S)-N-{3-[(Aminocarbonyl)amino]propyl}-2-((3S)-3-{[(6-chloro-2-naphthyl)sulfonyl]amino}-2-oxopyrrolidin-1-yl)-N-isopropylpropanamide;

(2S)-2-((3S)-3-{[(6-Chloro-2-naphthyl)sulfonyl]amino}-2-oxopyrrolidin-1-yl)-N-(cyclopropylmethyl)-N-(2-hydroxyethyl)propanamide;

(2S)-2-((3S)-3-{[(5'-Chloro-2,2'-bithien-5-yl)sulfonyl]amino}-2-oxopyrrolidin-1-yl)-N-ethyl-N-isopropylpropanamide;

(2S)-2-[(3S)-3-{[(E)-2-(4-Chlorophenyl)ethenyl]sulfonyl}amino)-2-oxopyrrolidin-1-yl]-N-ethyl-N-isopropylpropanamide;

(2S)-2-((3S)-{(2-Amino-2-oxoethyl)-3-({[(E)-2-(5-chlorothien-2-yl)ethenyl]sulfonyl}amino)-2-oxopyrrolidin-1-yl)-N-ethyl-N-isopropylpropanamide; and (2S)-2-((3S)-{(2-Amino-2-oxoethyl)-3-({[(6-chloro-1-benzothien-2-yl)sulfonyl]amino)-2-oxopyrrolidin-1-yl)-N-ethyl-N-isopropylpropanamide.

10. A pharmaceutical composition comprising a compound according to claim 1 together with a pharmaceutical carrier and/or excipient.

* * * * *

UNITED STATES PATENT AND TRADEMARK OFFICE
CERTIFICATE OF CORRECTION

PATENT NO. : 7,179,835 B2
APPLICATION NO. : 10/495586
DATED : February 20, 2007
INVENTOR(S) : Borthwick et al.

It is certified that error appears in the above-identified patent and that said Letters Patent is hereby corrected as shown below:

In the Claims:

Column 69 (Lines 39-44 of Claim 1) should read as follows:

Y represents -$C_{3-6}$cycloalkyl, phenyl, or an aromatic or non-aromatic 5-, 6- or 7- membered heterocyclic group consisting of at least one heteroatom selected from O, N or S and optionally substituted at C and/or N atoms by -$C_{1-3}$alkyl, $C_{1-3}$alkoxy, $C_{1-3}$alkylOH, halogen, -CN, -$CF_3$, -$NH_2$, -$CO_2H$ and -OH;

Column 70 (Lines 15-18 or Claim 2) should read as follows:

Y represents -$C_{3-6}$cycloalkyl, phenyl, or an aromatic or non-aromatic 5-, 6- or 7- membered heterocyclic group consisting of one or two O, N or S atoms and optionally substituted at C and/or N atoms by -$C_{1-3}$alkyl;

Column 70 (Lines 59-63 of Claim 6) should read as follows:

Y represents phenyl, or an aromatic or non-aromatic 5-, 6- or 7- membered heterocyclic group consisting of one or two heteroatoms selected from O, N or S atoms and optionally substituted at C and/or N atoms by -$C_{1-3}$alkyl.

UNITED STATES PATENT AND TRADEMARK OFFICE
CERTIFICATE OF CORRECTION

PATENT NO. : 7,179,835 B2
APPLICATION NO. : 10/495586
DATED : February 20, 2007
INVENTOR(S) : Borthwick et al.

It is certified that error appears in the above-identified patent and that said Letters Patent is hereby corrected as shown below:

Column 71 (Lines 4-8 of Claim 7) should read as follows:

Y represents phenyl, or an aromatic or non-aromatic 5-, 6- or 7- membered heterocyclic group consisting of one or two heteroatoms selected from O, N or S atoms and optionally substituted at C and/or N atoms by -$C_{1-3}$alkyl.

Signed and Sealed this

Third Day of July, 2007

JON W. DUDAS
*Director of the United States Patent and Trademark Office*